United States Patent
Gratzl et al.

(10) Patent No.: US 9,488,641 B2
(45) Date of Patent: Nov. 8, 2016

(54) MULTICELLULAR SYSTEM AND METHOD FOR MULTIPARAMETRIC ANALYSIS

(71) Applicant: Case Western Reserve University, Cleveland, OH (US)

(72) Inventors: Miklos Gratzl, Cleveland Heights, OH (US); Disha Sheth, Irvine, CA (US)

(73) Assignee: Case Western Reserve University, Cleveland, OH (US)

( * ) Notice: Subject to any disclaimer, the term of this patent is extended or adjusted under 35 U.S.C. 154(b) by 0 days.

(21) Appl. No.: 13/944,439

(22) Filed: Jul. 17, 2013

(65) Prior Publication Data

US 2014/0024068 A1    Jan. 23, 2014

Related U.S. Application Data

(60) Provisional application No. 61/673,032, filed on Jul. 18, 2012.

(51) Int. Cl.
*C12Q 1/02* (2006.01)
*G01N 33/50* (2006.01)

(52) U.S. Cl.
CPC .............................. *G01N 33/5008* (2013.01)

(58) Field of Classification Search
None
See application file for complete search history.

(56) References Cited

U.S. PATENT DOCUMENTS 7,709,246 B2 *    5/2010    Thielecke et al. ......... 435/287.1

OTHER PUBLICATIONS

Sheth, Thesis, May 2011.*
Sheth, Seminar Abstract, Mar. 2011.*
Sheth et al., Electroanalysis 20(6):627-634 (2008).*
Carlsson et al, Int. J. Cancer, 42:715-720 (1988).*
Klob et al, Lab Chip, 8:879-884 (2008).*
Sutherland, Science, 240:177-184 (1988).*
Hirschhaeuser et al., J. Biotechnol., 148:3-15 (2010).*

* cited by examiner

*Primary Examiner* — Thomas J Visone
(74) *Attorney, Agent, or Firm* — Tarolli, Sundheim, Covell & Tummino LLP

(57) ABSTRACT

A system for multiparametric analysis includes a substrate and a three-dimensional (3D) cell aggregate. The substrate has a major surface and includes at least one radial electrode array. The 3D cell aggregate is disposed on the major surface of the substrate. The 3D cell aggregate has a longitudinal surface at least a portion of which covers one or more of the electrodes of the radial electrode array.

13 Claims, 40 Drawing Sheets

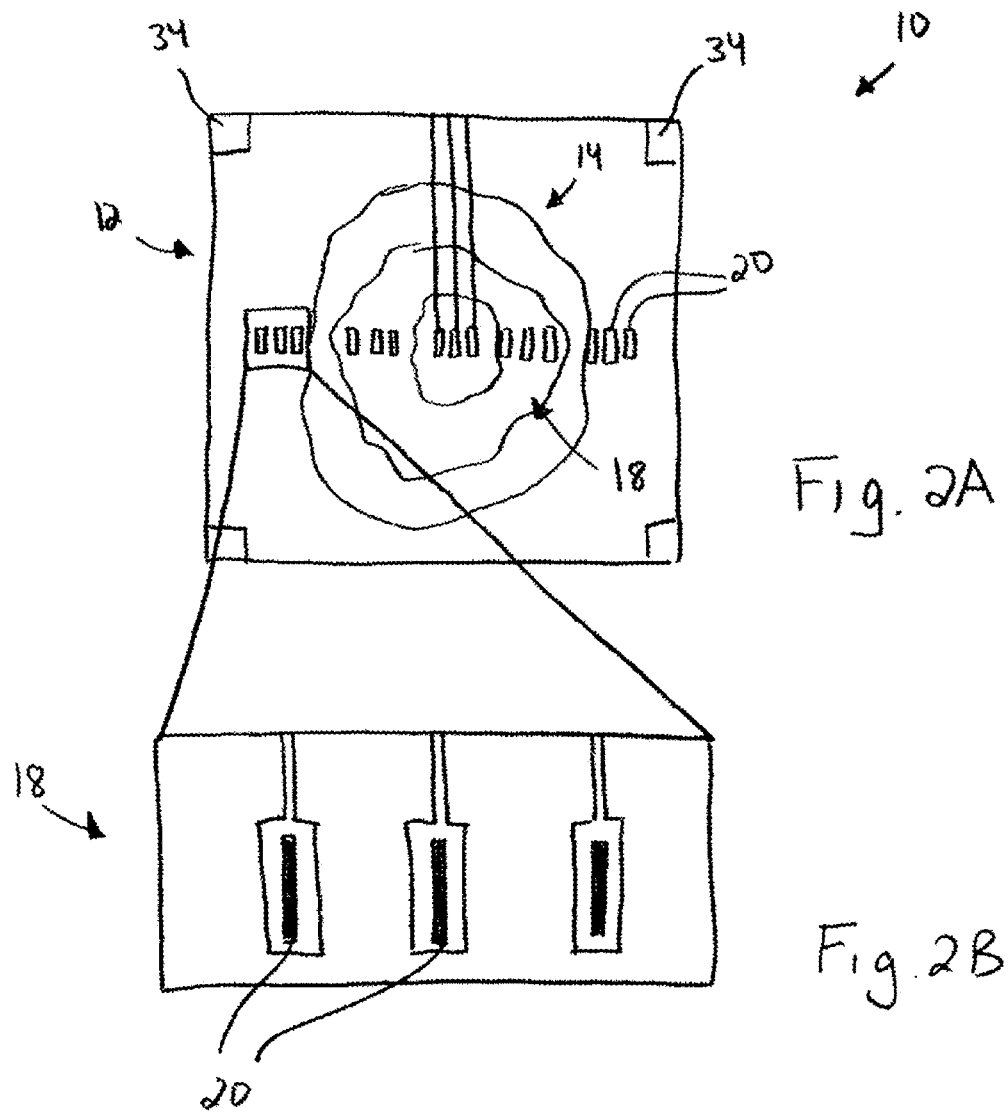
Fig. 2A
Fig. 2B
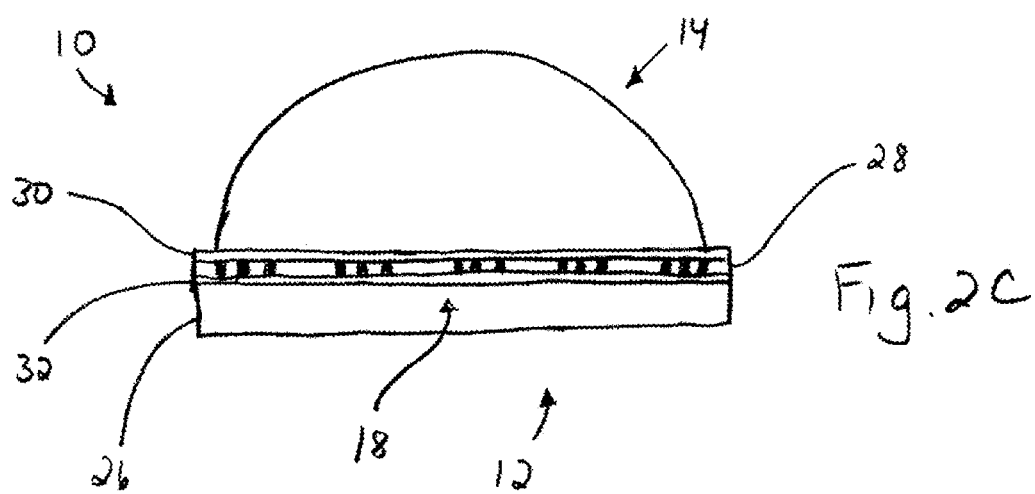
Fig. 2C

MULTICELLULAR SYSTEM AND METHOD FOR MULTIPARAMETRIC ANALYSIS

RELATED APPLICATION

This application claims the benefit of U.S. Provisional Patent Application Ser. No. 61/673,032, filed Jul. 18, 2012, the entirety of which is hereby incorporated by reference for all purposes.

TECHNICAL FIELD

This application relates to systems and methods for multiparametric analysis, and more particularly to a multicellular, multielectrode spheroid assembly for multiparametric analysis.

BACKGROUND

Heterogeneous oxygen distribution in tumor microenvironment can contribute to therapy failure. Anoxia and severe hypoxia in microregions of solid tumors due to increased distances between blood vessels results in decreased activity of cells or up-regulation of hypoxia linked cellular mechanisms, such as increased expression of glycolytic enzymes, glucose transporters, pH homeostasis enzymes, and angiogenic growth factors. All of these adaptations are in favor of survival and proliferation of hypoxic cells in adverse conditions making them resistant to therapy.

Methodologies for oxygen measurement in three-dimensional tissues developed so far, based on both optical and electrochemical principles, are restricted to measurements in single time point assuming steady state oxygen distributions. Both time- and depth-resolved continuous mapping of oxygen inside tumor tissue models has not been achieved.

SUMMARY

This present disclosure relates to systems and methods for multiparametric analysis. One aspect of the present disclosure relates to a system for multiparametric analysis that includes a substrate and a three-dimensional (3D) cell aggregate. The substrate has a major surface and includes at least one radial electrode array. The 3D cell aggregate is disposed on the major surface of the substrate. The 3D cell aggregate has a longitudinal surface at least a portion of covers one or more of the electrodes of the radial electrode array.

Another aspect of the present disclosure includes a method for testing the response of cells to exposure with at least one test agent. One step of the method includes providing a multiparametric analysis system comprising a substrate and a 3D cell aggregate. The substrate has a major surface and includes at least one radial electrode array. The 3D cell aggregate is disposed on the major surface of the substrate and has a longitudinal surface at least a portion of which covers one or more of the electrodes comprising the radial electrode array. Next, the at least one test agent is contacted with the 3D cell aggregate. One or more responses of the 3D cell aggregate to the at least one test agent is then measured.

Another aspect of the present disclosure includes a method for determining whether a patient will respond to a therapeutic strategy. One step of the method includes providing a multiparametric analysis system comprising a substrate and a 3D cell aggregate. The substrate has a major surface and includes at least one radial electrode array. The 3D cell aggregate is disposed on the major surface of the substrate and has a longitudinal surface at least a portion of which covers one or more of the electrodes comprising the radial electrode array. Next, at least one test agent is contacted with the 3D cell aggregate. One or more responses of the 3D cell aggregate to the at least one test agent is then measured. One or more of the measured responses to the at least one test agent is predictive of the patient response.

Another aspect of the present disclosure includes a method for designing an individual therapy for a patient. One step of the method includes providing a multiparametric analysis system comprising a substrate and a 3D cell aggregate. The substrate has a major surface and includes at least one radial electrode array. The 3D cell aggregate is disposed on the major surface of the substrate and has a longitudinal surface at least a portion of which covers one or more of the electrodes comprising the radial electrode array. Next, at least one test agent is contacted with the 3D cell aggregate. One or more responses of the 3D cell aggregate to the at least one test agent is then measured. A therapy is then selected based on the determined response(s).

BRIEF DESCRIPTION OF THE DRAWINGS

The foregoing and other features of the present disclosure will become apparent to those skilled in the art to which the present disclosure relates upon reading the following description with reference to the accompanying drawings, in which:

FIG. 2A is a top view showing an alternative configuration of the system in FIG. 1A;

FIG. 2B is a side view of the system in FIG. 2A;

FIG. 2C is a top view showing a magnified portion of the system in FIG. 2A;

FIG. 8A is a three-dimensional (3D) schematic illustrating one aspect of the present disclosure demonstrating the use of spherical symmetry in an idealized spheroid model. Radial concentration profile of oxygen can be obtained by opening a "window" along an equatorial plane (solid black) of a spheroid and introducing an array of radially arranged electrodes along that plane. FIG. 8B is a two-dimensional (2D) schematic (side view) showing the mapping of iso-concentration bands inside a spheroid using the radial electrode array. The measured concentrations by the electrodes are representative of the decrease in the oxygen flux through the spheroid because of oxygen uptake by the cells in each shell. FIG. 8C is a schematic of the actual platform with five Au microdiscs from E1 to E5 (side view, to scale). 50 µm diameter Au wires insulated with Parylene are aligned parallel to each other (center to center electrode distances in micrometers from E1→E5: 140, 100, 100, 90) and embedded in epoxy for mechanical support. ~10 µm cellulose acetate layer is deposited on top of the electrode array to prevent electrode fouling. FIG. 8D is a micrograph of the measurement platform (top view): an array of five Au microdisc electrodes. FIG. 8E is a MCF7-R cell model half spheroid (diameter ~1 mm, cell density ~0.3 million cells/µL) positioned on top of the measurement device. Electrode E1 is outside the spheroid, electrodes E2-E5 are hidden under the spheroid;

FIG. 14A shows the per volume rate of $O_2$ consumption is greater inside the high density spheroid because of ~4 times the number of cells inside this spheroid. FIG. 14B shows the per cell rate of $O_2$ consumption is greater inside the low density spheroid because of the presence of more oxygen inside this construct;

(FIG. 17A). Forward and reverse currents (grey lines) measured using SWV pulse protocol (FIG. 17B); current measured using LSV (black line) continuous scanning protocol (FIG. 17C). FIG. 17B shows the square wave voltammetry protocol. Potential was scanned from 0.2 V to −1.1 V (0.2 V to −0.4 V shown here) with 30 Hz frequency corresponding to 300 mV/s scan rate. Pulse amplitude of 50 mV and potential increment of 10 mV was used. The total time per scan was 4.33 s with a sample captured every 33 ms. Two pulses of the protocol have been enlarged (Inset) to show the time of sampling of current (*) during forward and reverse pulses. Difference between forward and reverse currents (a and b in FIG. 17A) measured for one of these pulses divided by total pulse amplitude (100 mV) gives the DSWV (FIG. 17D—grey line). Not drawn to scale. FIG. 17C shows the linear sweep voltammetry protocol. Scan potential was scanned from 0.2 V to −1.1 V (0.2 V to −0.4 V shown here) with scan rate of 100 mV/s. The total time per scan was 13 s with a sample captured every 10 ms. Samples were captured at 1 mV sampling interval, sampling frequency of 100 samples/s (inset). Two adjacent current measurements (c and d in FIG. 17A, *) were used to obtain differential current (FIG. 17D—black line). Not drawn to scale. DSWV (FIG. 17D—grey line) by taking a difference between forward (ia) and reverse (ib) currents normalized by voltage pulse amplitude of 100 mV. DLSV current per 1 mV (black line) obtained by numerical filtering of the continuous scan using first derivative Savitzky-Golay FIR filter of 25 points and quadratic polynomial smoothing;

DETAILED DESCRIPTION

Figure 1A:
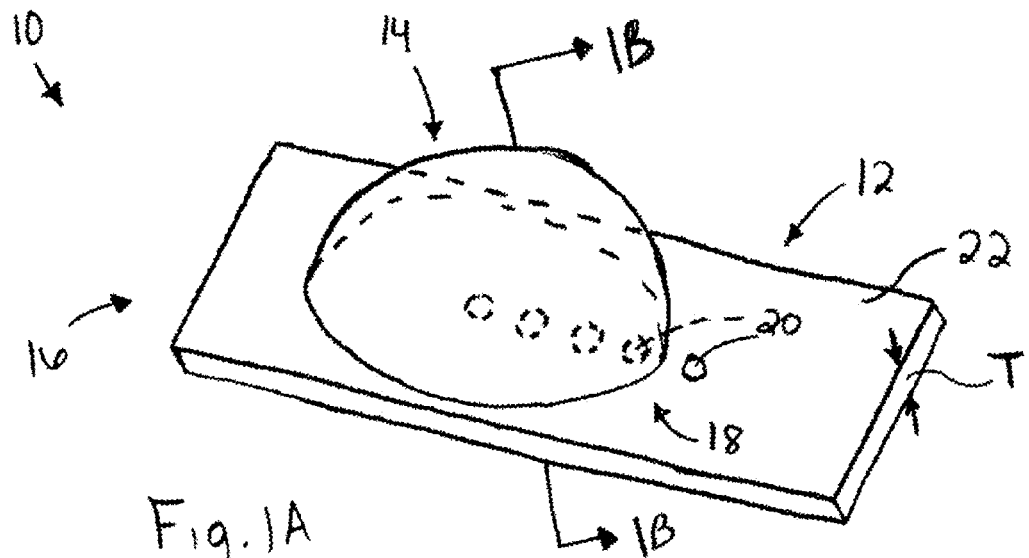
FIG. 1A is a perspective view of a multicellular, multiparametric analysis system constructed in accordance with one aspect of the present disclosure.

Methods involving conventional molecular biology techniques are described herein. Such techniques are generally known in the art and are described in detail in methodology treatises, such as *Current Protocols in Molecular Biology*, ed. Ausubel et al., Greene Publishing and Wiley-Interscience, New York, 1992 (with periodic updates). Unless otherwise defined, all technical terms used herein have the same meaning as commonly understood by one of ordinary skill in the art to which the present disclosure pertains. Commonly understood definitions of molecular biology terms can be found in, for example, Rieger et al., *Glossary of Genetics: Classical and Molecular*, 5th Ed., Springer-Verlag: New York, 1991, and Lewin, *Genes V*, Oxford University Press: New York, 1994. The definitions provided herein are to facilitate understanding of certain terms used frequently herein and are not meant to limit the scope of the present disclosure.

In the context of the application, the term "cell aggregate" can refer to a group of cells forming a three-dimensional (3D) space, generally resulting from forces applied along multiple axes.

As used herein, the term "tumor" can refer to a neoplasm (e.g., an abnormal growth of cells or tissue) and may be understood to include benign, e.g., non-cancerous growths and malignant (e.g., cancerous) growths including primary or metastatic cancerous growths. The term "neoplastic" can mean of or related to a neoplasm.

As used herein, the term "test agent" can refer to any compound, composition, or cell that can be tested as a potential therapeutic or diagnostic agent. In some instances, a test agent can promote cell death of proliferating or quiescent cells. In other instances, a test agent can inhibit mitosis. In yet other instances, a test agent can target one or more signaling pathways. In further instances, a test agent may contribute to the apoptosis of cancer cells either alone or in combination with other therapeutic agents or treatment protocols, such as radiation.

Non-limiting examples of test agents that can be used include small molecules, ligand-binding molecules, such as antibodies or antibody fragments, siRNAs, shRNAs, nucleic acid molecules (RNAs, DNAs, or DNA/RNA hybrids), polynucleotides, oligonucleotides, antisense oligonucleotides, aptamers, ribozymes, peptides, peptide mimetics, amino acids, carbohydrates, lipids, organic molecules, vitamins, hormones, natural products, and the like. In some instances, a test agent can include biological cells or parts of biological cells, such as microorganisms, immune cells or genetically-engineered cells. In other instances, a test agent can be a genetically-engineered virus, such bacteriophage or animal virus, such lentiviruses or genetically-engineered pseudoviruses. In further instances, an agent can be isolated or, in other instances, not isolated. As a non-limiting example, an agent can be a library of agents.

As used herein, the term "spheroid" can refer to an aggregate, cluster, or assembly of cells cultured to allow 3D growth. The spheroid may be highly organized with a well defined morphology, or it may be a mass of cells that have clustered or adhered together with little organization reflecting the tissue of origin. It may comprise a single cell type (homotypic) or more than one cell type (heterotypic). In some instances, the cells are primary cells isolated from tissue. In other instances, the cells may include a combination of primary isolates with an established cell line(s). Examples of cell types are described below.

As used herein, the term "subject" can refer to any animal, including, but not limited to, humans and non-human animals (e.g., rodents, arthropods, insects, fish (e.g., zebrafish)), non-human primates, ovines, bovines, ruminants, lagomorphs, porcines, caprines, equines, canines, felines, aves, etc. Typically, the terms "patient" and "subject" are used interchangeably herein in reference to a human subject.

Overview

One aspect of the present disclosure is based, at least in part, on the discovery of a multicellular system for multiparametric analysis and a related continuous analytical approach for mapping oxygen tension in a multicellular model. As discussed in more detail below, this discovery permits simultaneous and real-time analysis in multicellular models (e.g., tumor models) for assessing drug penetration, oxygenation status, and/or acidification in one or more particular cellular regions. In some instances, the present disclosure provides knowledge of oxygen distribution inside tumor biopsies and/or tumor models, along with therapeutic efficacy of drug molecules. In other instances, the present disclosure may be valuable for in vitro screening and identification of potential new drug molecules during the drug development process. Other applications of the present disclosure are discussed below.

In another aspect, a system was developed that incorporated a model 3D cell aggregate (e.g., a partial spheroid) and an array of gold microdisc electrodes using MEMS fabrication techniques. Oxygen concentration profiles inside the model spheroid were measured using the system. A monotonically decreasing relationship between the rate of cellular oxygen consumption and extracellular oxygen concentration was derived from the recorded data by discrete numerical analysis. Presently, there is no information available regarding the quantitative relationship between oxygen consumption-concentration for an entire cell. Unlike previous models that assume a constant rate of oxygen consumption, the present disclosure advantageously provides a continuous model of oxygen concentration that considers linearly decreasing consumption rates.

In another aspect of the present disclosure, oxygen consumption of single cells and small cell clusters was measured using a microring electrode platform. The microring electrode platform allowed for averaged recording of oxygen consumption from around single cell and small cell clusters with sensitivity of about 1% change in $O_2$ concentration with 95% confidence. Information about individual cells can be obtained using this platform, which complements the 3D oxygen mapping approach for spheroids. For example, single cell processes like multi-drug resistance, metabolism, respiration, etc., as well as cumulative tissue effects can be investigated using the microring electrode platform. Information obtained from both approaches can provide a comprehensive picture of cancer chemotherapy failure mechanisms.

Another aspect of the present disclosure is based on the mathematical concept of spatial averaging. Spiral electrodes with Fermat's geometry were developed to obtain spatial averaging of concentration inside heterogeneous microliter size drops. This design can be used, for example, to obtain average concentrations of substances inside the spheroid models of the present disclosure. Additional aspects of the present disclosure are discussed below.

Multiparametric Analysis System

One aspect of the present disclosure relates to a system 10 (FIGS. 1A-C) for multiparametric analysis that includes a substrate 12 and a 3D cell aggregate 14. The substrate 12 has a major surface 16 and includes at least one radial electrode array 18. The 3D cell aggregate 14 is disposed on the major surface 16 of the substrate 12. The 3D cell aggregate 14 has a longitudinal surface (not shown) at least a portion of which covers one or more of the electrodes 20 of the radial electrode array 18. As described in more detail below, the system 10 may find use in high-throughput drug screening applications, e.g., to speed up the process of screening and reduce the cost of animal experiments, for mechanistic exploration of cancer tumor physiology, and/or for personalized therapy for better patient care.

Substrates

Figure 1B:
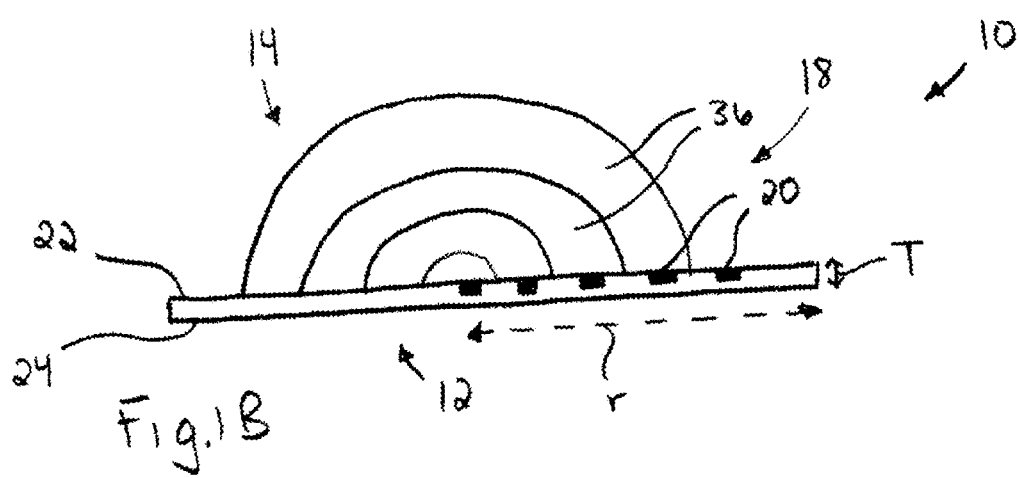
FIG. 1B is a cross-sectional view taken along Line 1B-1B in FIG. 1A.
Figure 1C:
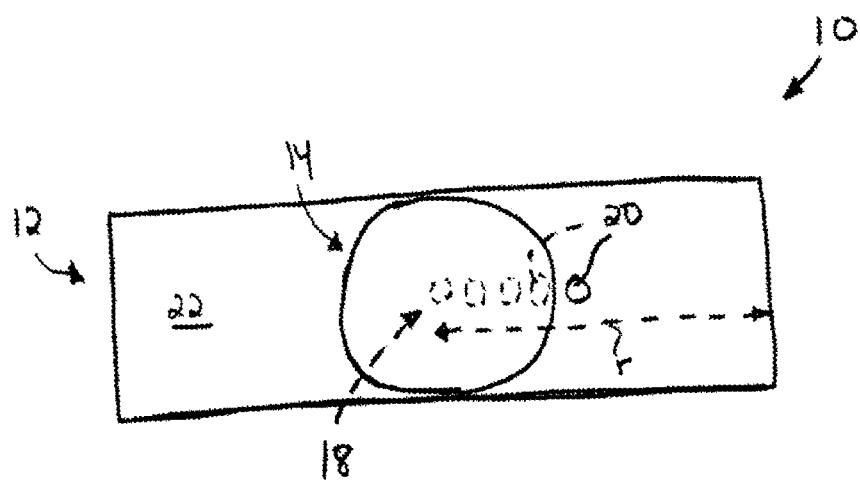
FIG. 1C is a top view of the system shown in FIG. 1A.

As shown in FIGS. 1A-C, one component of the system 10 includes a substrate 12. The substrate 12 includes oppositely disposed first and second major surfaces 22 and 24 that define a thickness T. The thickness T of the substrate 12 can vary depending upon the desired use of the system 10, as well as the technique(s) used to fabricate the substrate 12. In some instances, the substrate 12 can have a thickness T of about 200 microns to about 900 microns. In other instances, the substrate 12 can have a thickness T of about 500 microns to about 700 microns. Although the substrate 12 is shown in FIGS. 1A-C as having a rectangular shape, it will be appreciated that the substrate can have any desired shape (e.g., square, ovoid, circular, etc.) depending upon the intended use of the system 10, as well as other design considerations.

The substrate 12 can have a single layer or multilayer (FIGS. 2A-4B) configuration. In the multilayer configuration, the material(s) comprising each of the layers can be the same or different as compared to other layers of the substrate 12. Examples of materials used to form one or more layers of the substrate 12 can include glass, polymers (e.g., polycarbonates, polyimides, acrylics), epoxies, silicon, cellulose acetate, and the like. The choice of material(s) used to form the substrate 12 may depend upon the intended use of the system 10. For example, a clear or transparent substrate 12 (e.g., glass) may be selected where the system 10 is intended for use with one or more optical analysis tools.

Figure 6:
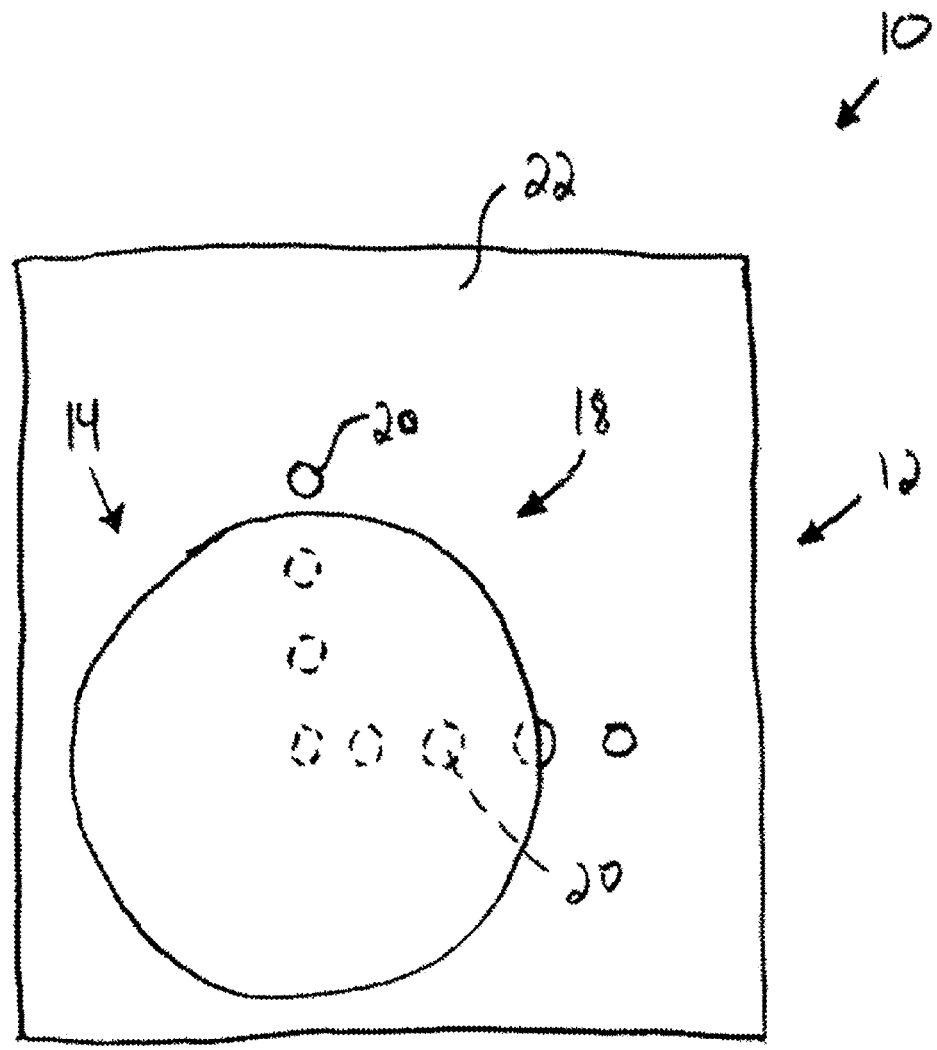
FIG. 6 is an alternative configuration of the system in FIG. 1A.

The substrate 12 includes at least one radial electrode array 18. The radial electrode array 18 can include two or more electrodes 20 that are radially spaced apart along a radius r of the substrate 12. The radial electrode array 18 can be embedded within the substrate 12 or disposed thereon (e.g., on the first major surface 22), and can extend the entire length of the radius r or only a portion thereof. The electrodes 20 comprising the radial electrode array 18 can be partially enveloped by an insulating material, such as Parylene. The electrodes 20 can be spaced apart by a radial distance, which may be determined based on the size of the cells comprising the 3D cell aggregate 14, the degree of resolution desired, the size of the electrodes, etc. In one example, the distance between electrodes 20 (e.g., center-to-center electrode distance) can be between about 50 microns to about 150 microns (e.g., about 90 microns to about 140 microns). The substrate 12 can include only one radial electrode array 18 or, alternatively, two or more radial electrode arrays (FIG. 6). Where two or more radial electrode arrays 18 are included, it will be appreciated that the arrays can be arranged on or within the substrate 12 in any desired configuration (e.g., spaced about 90° apart from one another) (FIG. 6).

Figure 5A:
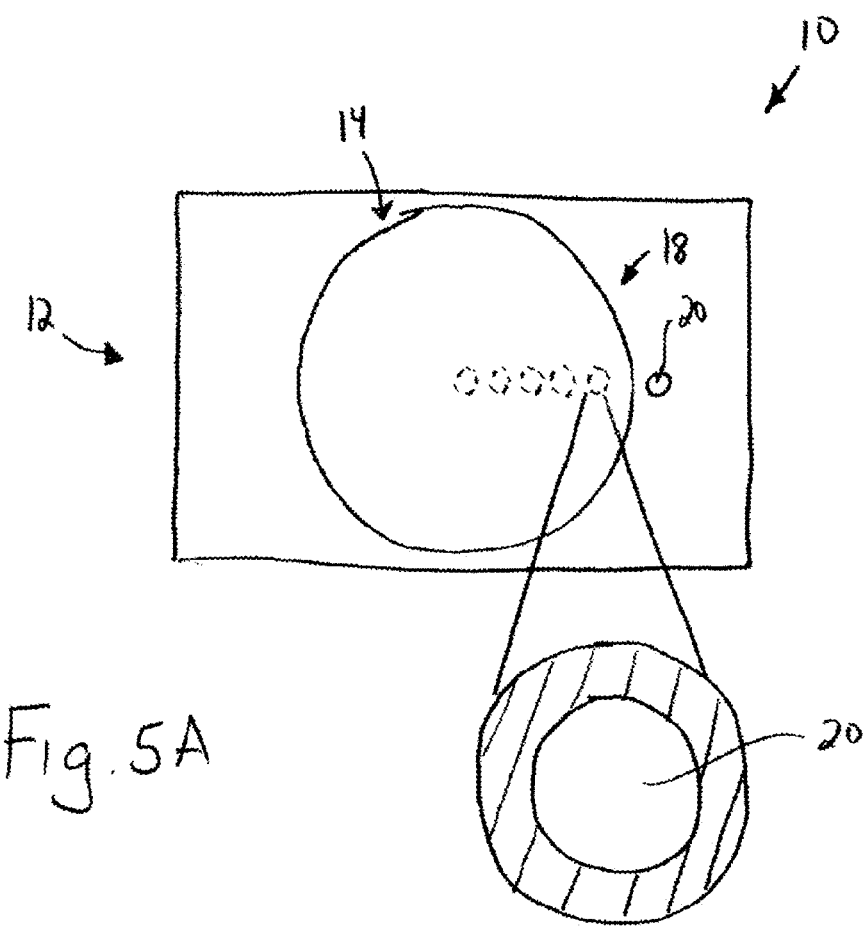
FIG. 5A is a top view showing an alternative configuration of the system in FIG. 1A.

The size, shape, and number of electrodes 20 comprising each radial electrode array 18 can be varied depending upon the intended use of the system 10. In some instances, each of the electrodes 20 can have a diameter of about 5 microns to about 50 microns. In one example, each of the electrodes 20 can be a microdisc electrode (FIG. 5A). In another example, a radial electrode array 18 can comprise five microdisc electrodes. The size, shape and number of electrodes 20 comprising a single radial electrode array 18 can be the same or different. Additionally, the size, shape, and number of electrodes 20 can be same or different between multiple radial electrode arrays 18.

Electrodes 20 comprising the radial electrode array 18 can be made from a variety of materials. The materials used for the electrodes 20 of a particular radial electrode array 18 will depend upon the intended use of the system 10. In some instances, gold can be used to form one or more electrodes 20 of a radial electrode array 18 where detection of oxygen is desired. In other instances, platinum (or a platinum alloy) can be used to form one or more electrodes 20 of a radial electrode array 18 where detection of hydrogen ions (i.e., pH) is desired. Other examples of materials that may be used to form the electrodes 20 of a radial electrode array 18 can include carbon fiber, platinum alloys (e.g., platinum-iridium, platinum-palladium, platinum-ruthenium, platinum-tungsten), titanium, copper, and other noble metals.

Figure 3A:
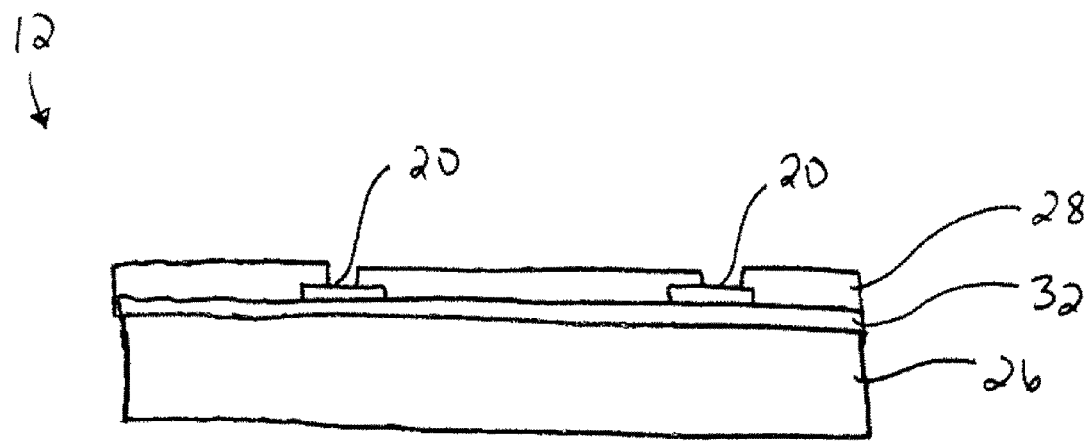
FIG. 3A is a side view showing an alternative configuration of a substrate comprising the system in FIG. 1A.
Figure 3B:
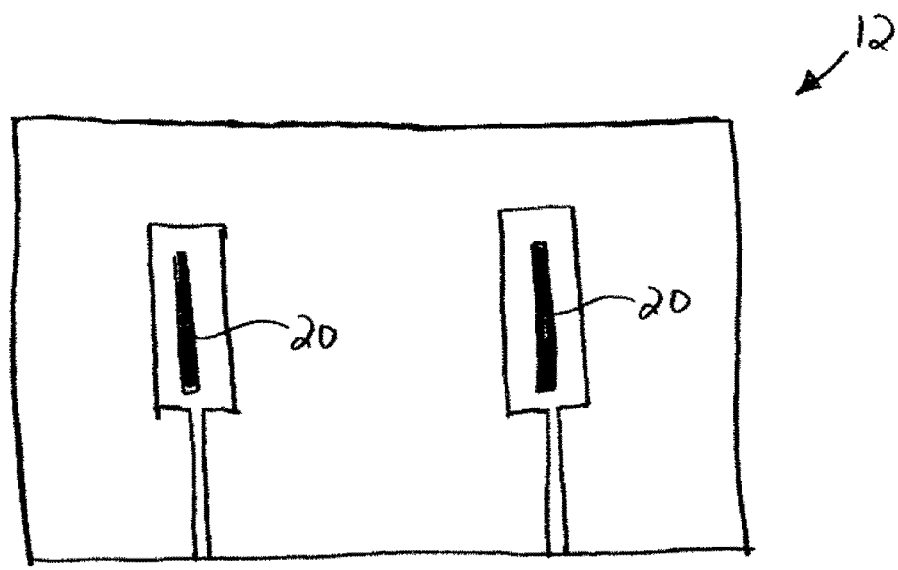
FIG. 3B is a top view of the substrate in FIG. 3A.
Figure 4A:
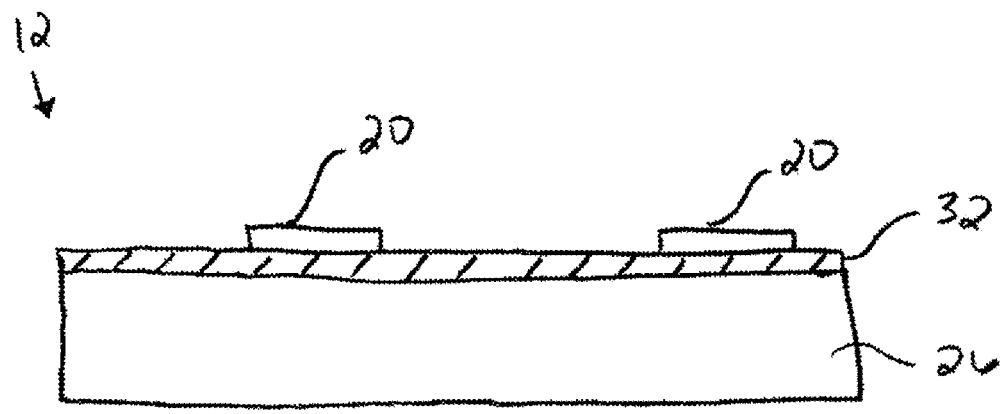
FIG. 4A is a side view showing an alternative configuration of the substrate in FIG. 3A.
Figure 4B:
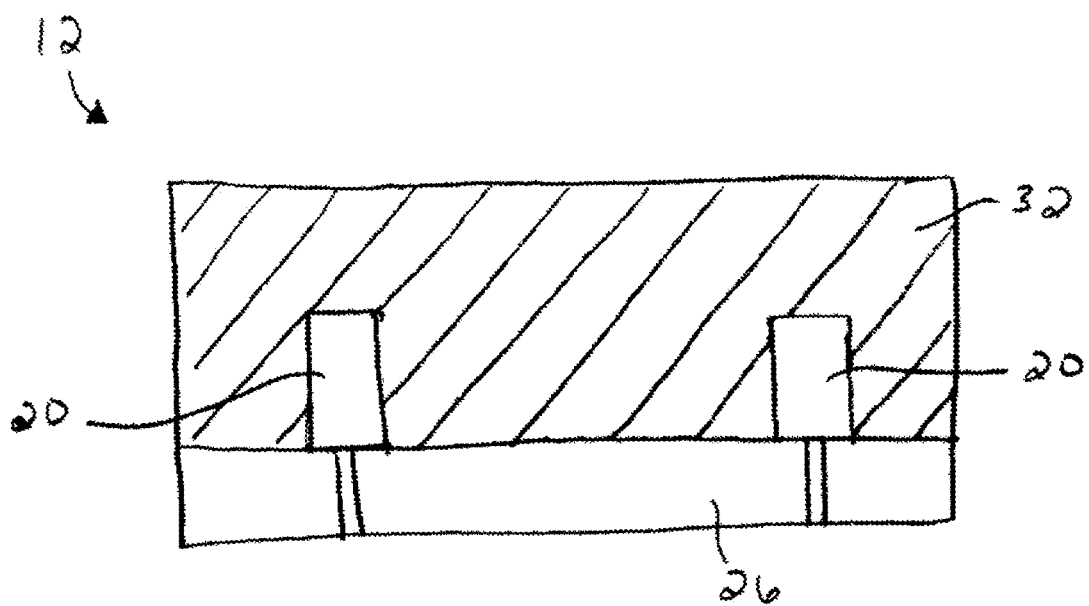
FIG. 4B is a top view of the substrate in FIG. 4A.

In one example, the substrate 12 can have a multilayer configuration comprising a first base layer 26, a second intermediate layer 28 disposed on at least a portion of the first base layer, and an optional spacer layer 30 disposed on the second intermediate layer to prevent or mitigate biofouling of the radial electrode array 18. Examples of substrates 12 with a multilayer configuration are shown in FIGS. 2A-4B. As shown in FIGS. 2A-C, for example, the base layer 26 can comprise silicon, the intermediate layer 28 can be a polyimide layer, and the spacer layer 30 can be a cellulose acetate layer. Also included in the substrate 12 shown in FIGS. 2A-C is a silicon dioxide layer 32, upon which the radial electrode array 18 can be disposed or embedded therein. FIGS. 3A-B show an alternative multilayer configuration of the substrate 12 comprising a base silicon layer 26, a silicon dioxide layer 32 thereon, and a polyimide layer 28 disposed on top of the silicon dioxide layer. Another multilayer configuration of the substrate 12 is shown in FIGS. 4A-B and includes a base silicon layer 26 with a silicon dioxide layer 32 disposed thereon. In both of the configurations shown in FIGS. 3A-B and 4A-B, the radial electrode array 18 can be disposed on the silicon dioxide layer 32.

Figure 5B:
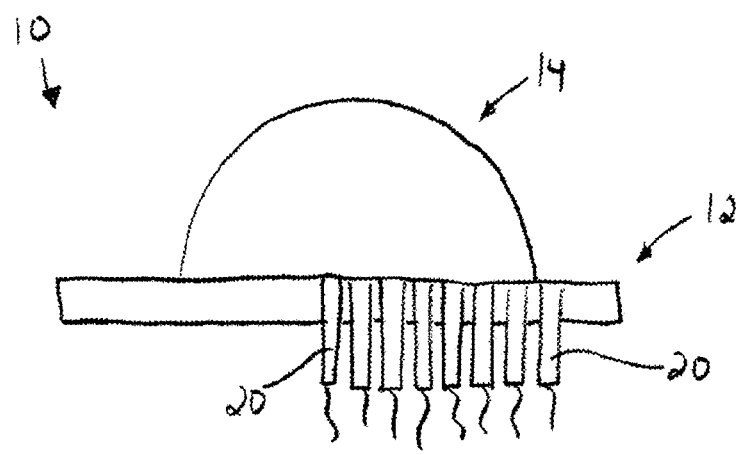
FIG. 5B is a side view of the system in FIG. 5A.
Figure 7:
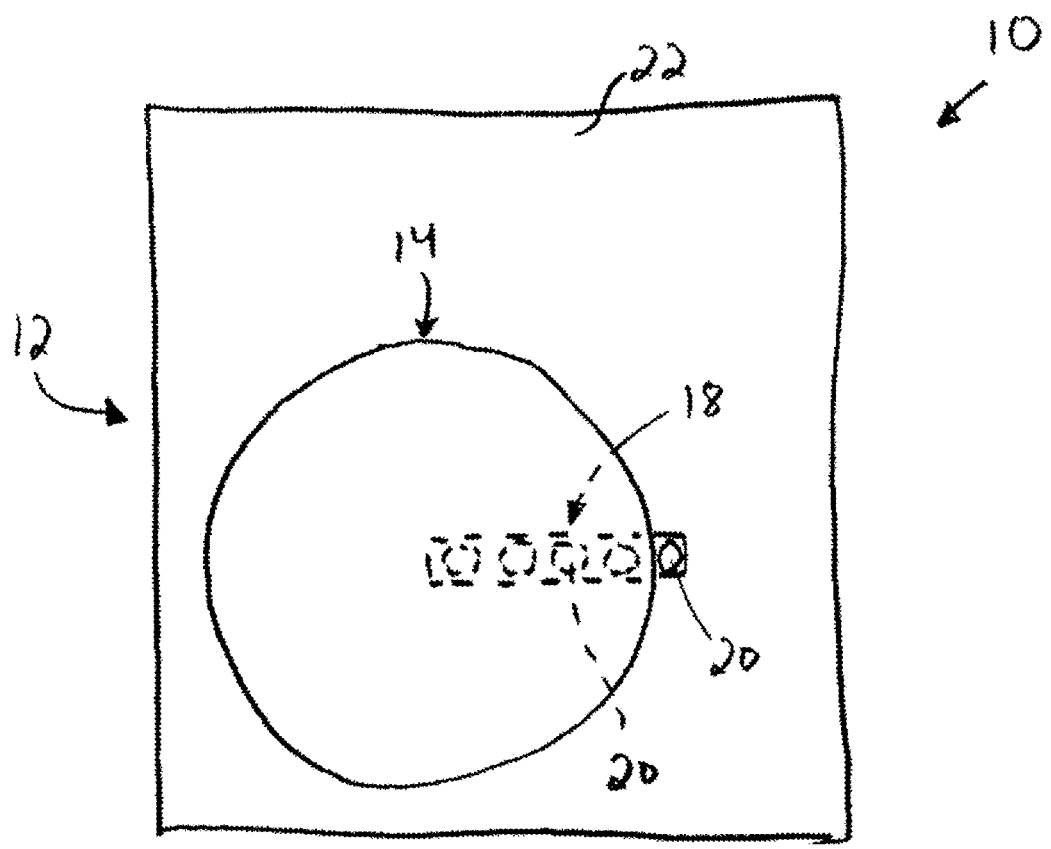
FIG. 7 is an alternative configuration of the system in FIG. 1A.

The radial electrode array 18 can be disposed on the substrate 12 in a variety of configurations. In some instances, the radial electrode array 18 can be disposed atop the first major surface 22 of the substrate 12 and securely attached thereto (e.g., using an adhesive or other similar means). In other instances, the radial electrode array 18 can be embedded (e.g., by laser etching) within the first major surface 22 of the substrate 12. As shown in FIG. 7, for example, the radial electrode array 18 can comprise a plurality of electrodes 20 radially stacked within a laser drilled slot (not shown in detail). In further instances, the radial electrode array 18 can be disposed atop an intermediate layer 28 of the substrate 12 and then partially covered or enveloped within an overlaid layer. In still other instances, all or only a portion of each of the electrodes 20 comprising the radial electrode array 18 can extend through an opening (e.g., a laser drilled hole) (not shown in detail) that extends axially through the substrate 12 (FIG. 5B).

It will be appreciated that the substrate 12 can include one or more guides 34 (FIG. 2A) to assist in using the system 10. As shown in FIGS. 2A-B, for example, the guide 34 can comprise a dye or other contrast agent disposed at each corner of the substrate 12. Alternatively, one or more indents (not shown) can be included in the substrate 12. The guides 34 can facilitate placement and positioning of the system 10 during various analytical procedures, such as microscopy.

Substrate and Radial Electrode Array Fabrication

In another aspect, substrates 12 of the system 10 can be fabricated with existing micro-electro mechanical systems (MEMS) technology for single and multi-parameter measurement array designs. As described below, at least two different MEMS approaches can be implemented to fabricate substrates 10 and radial electrode arrays 18 of the present disclosure.

In some instances, electrodes 20 can be fabricated on the polished side of a silicon or Pyrex wafer (prime grade—100) (about 100 mm diameter) with an insulating silicon dioxide film (about 1.5 m-thick). Silicon dioxide film can also be grown in-house by thermal oxidation at about 1100° C. in an oxidizing environment of $O_2$ and $H_2$. The electrodes 20, interconnects (not shown), and contact pads (not shown) can be fabricated using gold metallization. A Shipley 1813 photoresist can be spin coated and patterned as a sacrificial molding layer for the electrodes. The electrodes 20 can be formed by magnetron sputtering of about 10 nm-thin titanium for adhesion promotion, followed by a gold film (about 200 nm-thick).

The sacrificial layer of photoresist can be dissolved by soaking the wafer in acetone, leaving behind only the gold electrodes anchored firmly to the underlying silicon dioxide layer. After gold liftoff, negative tone polynorbornene (PNB) or positive tone Photoneece® PWDC-1000 polyimide, which is photo-definable can be deposited on the wafer. Photodefinable polyimide can be processed in much the same manner as conventional photoresists, which involves spin coating the polyimide onto the wafer, followed by UV exposure through a lithography mask, polyimide development, and thermal curing. An insulating polyimide layer (about 3-5 µm-thick) can be deposited on the whole wafer except the active electrode area. These electrodes 20 can be recessed (e.g., by 3-5 µm) from the polyimide surface where the 3D cell aggregate 14 will be positioned to minimize biofouling. Finally, the hydrophobic polyimide can be exposed to a fixed duration of $O_2$ plasma etch to make it more hydrophilic and to promote adhesion between the 3D cell aggregate 14 and the polyimide for proper positioning at the sensing site. Other non-toxic insulating materials, such as silicon carbide can also be used in place of polymeric materials. Gold microelectrodes can be used for measurement of oxygen and anthracyclines, which are commonly used as a chemotherapeutic drug.

A major advantage of the foregoing fabrication process is the capability of a high throughput assembly line where hundreds of systems 10 can be fabricated on a single wafer. Also, minor changes in the substrate dimensions and materials (e.g., platinum instead of gold) can be implemented quickly without a need to change the fabrication process flow. Therefore, in some instances, the foregoing method of fabrication may be ideal for bulk production of the system 10.

In another aspect, gold wires can be insulated using Parylene. A mold can be fabricated by laser machining holes of desired sizes in an acrylic substrate (about 0.5 mm thick). For instance, through holes of about 70-80 µm with about 50 µm between adjacent holes can be obtained by laser machining. Gold wires (of about 50 µm diameter) insulated with Parylene (about 10 µm) can be passed through these holes and can be fixed in place by epoxy resin or cynoacrylate. Other noble metal wires of desired diameter pre-coated with PTFE or polyimide insulation can also be used.

A major advantage of systems 10 prepared according to the foregoing method is that the surface of the electrodes 20 can be regenerated by physically polishing the electrodes. This can be done by using a fine emery paper or a 0.3 µm carbide grit, which is commonly used for polishing conventional microdisc electrodes embedded in glass capillaries. Thus, such electrodes 20 can be reused for a long period of time.

3D Cell Aggregates

In another aspect, the system 10 includes a 3D cell aggregate 14 disposed on a major surface 16 (e.g., the first major surface 22) of the substrate 12. In some instances, the 3D cell aggregate 14 can comprise a partial spheroid having, e.g., a hemi-spherical configuration. It will be appreciated that other configurations of the 3D cell aggregate 14 are possible, such as cube or cuboid. The 3D cell aggregate 14 has a longitudinal surface, at least a portion of which covers one or more of the electrodes 20 of the radial electrode array 18. In some instances, all of the electrodes 20 comprising the radial electrode array 18 can be covered by the 3D cell aggregate 14. In other instances, the 3D cell aggregate 14 can be disposed about the radial electrode array 18 such that the position of each electrode 20 corresponds to a separate iso-concentric band 36 (FIG. 1B) of the 3D cell aggregate.

Multicellular 3D cell aggregates 14 can comprise any one or combination of embryonic or adult cells capable of forming a spheroid. In some instances, a 3D cell aggregate 14 can comprise a single cell type (homotypic). As used herein, the term "homotypic" can refer to cells of a single type. For example, commercially available cell lines are generally homotypic. In other instances, a 3D cell aggregate 14 can comprise a mixture of two or more cell types (heterotypic). As used herein, the term "heterotypic" can refer to cells of more than one cell type. For example, primary isolate tissue comprising different cell types will be heterotypic.

The internal environment of a 3D cell aggregate 14 (e.g., a spheroid) is dictated by the metabolism and adaptive responses of cells with a well-defined morphological and physiological geometry. Most homotypic spheroids develop concentric layers of heterogeneous cell populations, with cells at the periphery and layers of quiescent cells close to a necrotic core. The heterogeneous arrangement of cells in a spheroid can mimic initial avascular stages of early tumours. Although homotypic spheroids are able to closely mimic the in vivo morphology, some of the biological complexity is lost. Thus, by including more than one cell type in a spheroid, tumor cell interactions with other cell types reflecting natural cell interaction in vivo can be established to better represent the in vivo environment.

3D cell aggregates 14 of the present disclosure can be characterized in that they exhibit characteristics that substantially mimic those of the tissue of origin, such as in terms of antigen profile and/or genetic profile, tumor biologic characteristics, tumor architecture, cell proliferation rate(s), tumor microenvironments, therapeutic resistance and composition of cell types, etc. Thus, 3D cell aggregates 14 can exhibit a substantially similar or identical behavior to that of natural cell systems, e.g., with respect to organization, growth, viability, cell survival, cell death, metabolic and mitochondrial status, oxidative stress and radiation response as well as drug response. Since the 3D cell aggregates 14 can be substantially identical to in vivo cell systems, the system of the present disclosure can be used for diagnostic and/or therapeutic purposes, pharmacokinetic profiling, pharmacodynamic profiling, efficacy studies, cytotoxicity studies, penetration studies of compounds, therapeutic resistance studies, antibody testing, personalized or tailored therapies, RNA/DNA drug testing, small molecule identification and/or testing, biomarker identification, tumor profiling, hyperthermia studies, radioresistance studies, and the like.

In another aspect, the tissue which may be used for 3D cell aggregate 14 preparation may be a normal or healthy biological tissue, or may be a biological tissue afflicted with a disease or illness, such as a tumor tissue or fluid derived from a tumor. In some instances, the tissue is a mammalian tissue. Also encompassed are metastatic cells. The tissue may be obtained from a human, such as a patient during a clinical surgery. Alternatively, the tissue may be obtained from a biopsy. The tissue may also be obtained from animals, such as mice, rats, rabbits, and the like. Besides cells originating from tumor tissue, other cells with various indications, such as smooth muscle cells, adipocytes, neural cells, stem cells, islet cells, foam cells, fibroblasts, hepatocytes and bone marrow cells, cardiomyocytes, and enterocytes are also encompassed within the present disclosure.

Other Devices

In another aspect, an alternative configuration of the system 10 can comprise a substrate 12 (e.g., silicon) having at least one ring-shaped electrode (e.g., platinum) (not shown) disposed thereon, and one or more cells (e.g., a small population) disposed on the substrate within the ring-shaped electrode. In some instances, the ring-shaped electrode can be flush with the substrate 12 so as to avoid physical obstruction of analyte diffusion. Precise cell patterning is made possible by positioning cell(s) inside the ring-shaped electrode by hydrodynamic manipulation. In one example, an array of ring-shaped electrodes and respective cell sites can be fabricated such that parallel experiments can be performed on one system to obtain multiple data sets for biostatistical analysis in the same amount of time that would be required to get one data set. For instance, an array of ring-shaped electrodes can be used for measuring oxygen uptake from a single cell. Such a configuration can permit averaged recording of oxygen consumption from around a single cell or small cluster of cells with increased sensitivity. It will be appreciated that the system incorporating a ring-shaped electrode can additionally or optionally be used for transport studies of analytes other than oxygen for single cell investigation. Additionally, it will be appreciated that spatially averaging electrodes can be performed to assess 3D averaged bulk concentrations (as described in Example 5 below).

Methods

Another aspect of the present disclosure includes a method for testing the response of cells to exposure with at least one test agent. The method can find use in a variety of different applications, including high-throughput drug screening applications, mechanistic exploration of cancer tumor physiology, and/or for personalized therapy for better patient care. The method can find use in other diagnostic and/or therapeutic purposes, such as pharmacokinetic profiling, pharmacodynamic profiling, efficacy studies, cytotoxicity studies, penetration studies of compounds, therapeutic resistance studies, antibody testing, personalized or tailored therapies, RNA/DNA drug testing, small molecule identification and/or testing, biomarker identification, tumor profiling, hyperthermia studies, radioresistance studies, and the like.

One step of the method can include providing a multiparametric analysis system 10. The multiparametric analysis system 10 can be identically or similarly constructed as the system shown in FIGS. 1A-C, as well as any of the other system configurations described above. In some instances, the system 10 can be incorporated into a testing assembly (not shown) comprising a fluid container (e.g., a Petri dish) (not shown) and an electrode (e.g., a Clark-type electrode) (not shown). The fluid container can further include an appropriate cell medium for sustaining the 3D cell aggregate 14. One skilled in the art will appreciate that the constituents of the cell medium can be varied depending upon the type of cell(s) comprising the 3D cell aggregate 14. Examples of appropriate cell media are known in the art. The system 10 can be placed in the fluid container such that the entire 3D cell aggregate 14 is immersed in the cell medium. At least a portion of the electrode (e.g., a Clark-type electrode) can then be placed into contact with the cell medium.

Figure 35:
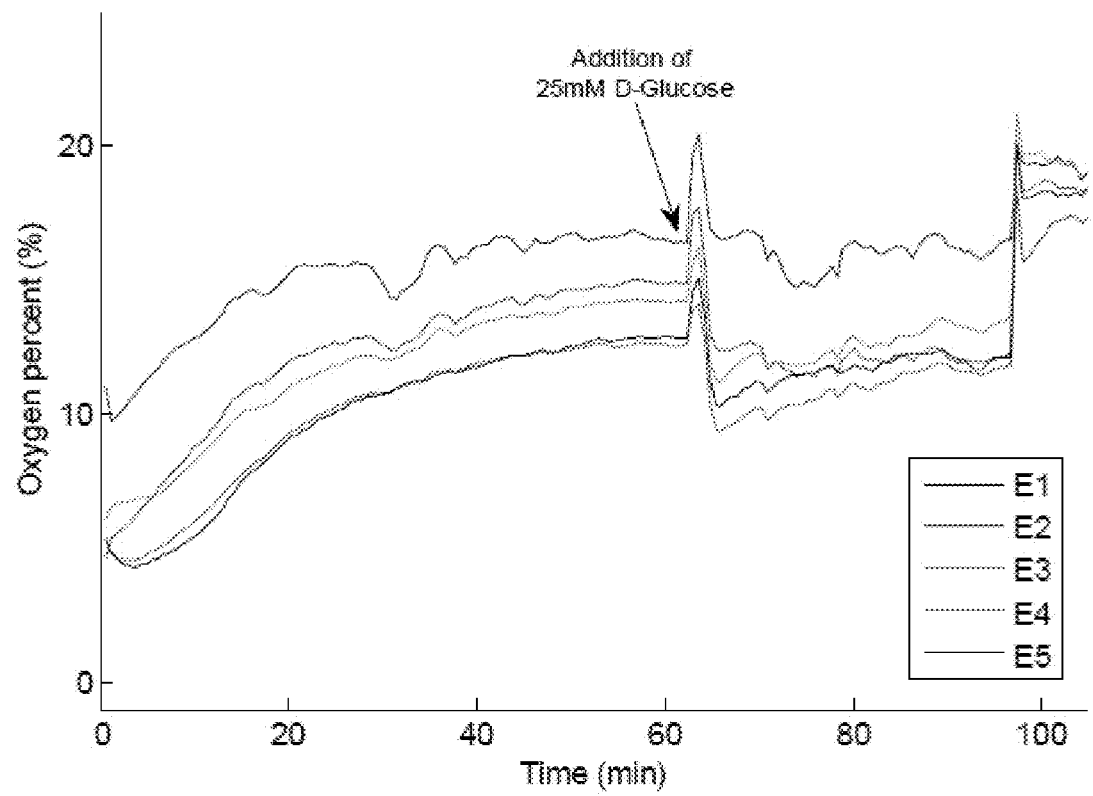
FIG. 35 is a graph showing addition of glucose to the PBS resulted in decrease in the measured oxygen concentration almost instantaneously.

The configuration of the testing assembly can be varied depending upon the particular response being measured by the method. One example of such a testing assembly is shown in FIG. 35. The configuration shown in FIG. 35 may be appropriate in instances where measurement of a diffusing analyte, such as oxygen is desired. In this instance, it is important to maintain a constant oxygen concentration during testing. To maintain an air-tight system, a sealing member, such as bag or other enclosing mechanism can be placed about the system (and the fluid container) to ensure maintenance of a constant oxygen concentration. Where other responses are being measured, such as pH and drug concentration, there may not be a need for such an enclosing mechanism.

Once the testing assembly is prepared and ready for use, a desired amount of at least one test agent can be contacted with the system 10 (i.e., the 3D cell aggregate 14). After contacting one or more test agents with the system 10, one or more responses of the 3D cell aggregate 14 can be measured. In some instances, the level of one or more diffusing analytes (e.g., a gas, such as oxygen) can be measured. Diffusing analytes can include any analyte capable of being detected by electrochemical and/or optical assay(s). In other instances, the level of one or more biomarkers associated with cellular metabolism can be measured. Biomarkers are generally characteristics that can be objectively measured and evaluated as indicators of normal biologic processes, pathogenic processes, or pharmacologic responses to a therapeutic intervention. Within the present disclosure, any biomarker(s) known to a person skilled in the art as suitable for the method can be detected. Non-limiting examples of biomarkers can include proteins, as well as molecular or genomic biomarker(s) that are prognostic, therapeutic or predictive in nature. In one example, the biomarker can be a hypoxia-related biomarker, such as hypoxia-inducible factor 1, alpha subunit. In another example, a biomarker (e.g., protease activity) can be indicative of cell viability.

In one aspect, measurement of diffusing analytes and/or biomarkers can be performed using direct or indirect techniques. By way of example, indirect measurement can include the use of rate of substrate depletion to monitor enzyme levels, whereas direct measurement can involve measurement of enzyme levels per se.

In another aspect, an electrochemical measurement protocol can be implemented to measure the response(s). For example, a measurement protocol using a numerical differentiation method of continuous scanned LSV to obtain redox current peaks can be implemented (as described in Example 3 below). Such an approach has several advantages, including: continuous LSV provides optimal interrogation of the electrochemical system; inherent subtraction of capacitive background current; and comparable sensitivity to a differential pulsing method.

In a further aspect, a continuous model (e.g., as described in Example 2) can be used to determine the concentration of one or more diffusing analytes and/or biomarkers inside a 3D cell aggregate 14 of the system 10. In one example, a continuous model can be used to determine oxygen concentration inside a 3D cell aggregate 14. In previous efforts to obtain a continuous model of oxygen concentration inside spheroid tumor models, the rate of oxygen consumption had been assumed to be constant for all the depths of the tissue regardless of the surrounding oxygen concentrations. In some instances, the method advantageously includes a continuous model for oxygen concentration for a 3D cell aggregate 14 that uses a linearly approximated relationship between the rate of oxygen consumption and concentration in hypoxic regions. Thus, in some instances, the method can include the use of software (e.g., based on the model described in Example 2) to predict the distribution of oxygen inside a 3D cell aggregate 14 knowing the activity of the cells in terms of linear rate constant of consumption for oxygen. Alternatively, the method can include the use of such software to estimate the rate constant of oxygen consumption from the measured oxygen data inside a 3D cell aggregate 14.

The method enables simultaneous and real-time measurement of at least one diffusing analyte (e.g., hydrogen ions and oxygen) and at least one biomarker, which permits true multiparametric analysis. In some instances, a test agent can first be contacted with the 3D cell aggregate 14. Oxygen profiles can then be continuously measured inside a 3D cell aggregate 14, while detection of cell viability is concurrently performed in one or more regions of the 3D cell aggregate for correlation with the oxygen measurements. Subsequent analysis of the correlation(s) between the oxygen profiles and cell viability may be informative of test agent efficacy. For example, obtaining the correlation between oxygen and test agent concentration along with quantification of cell death at different depths of the 3D cell aggregate 14 may provide valuable information into the effect of oxygen concentration on agent efficacy inside the 3D cell aggregate.

In another example, the method can be used to elucidate oxygen-dependent pathways in cancer cells. For instance, differentiation in embryonic spheroids can cancer stem cell spheroids is known to depend on oxygen concentration. Thus, by continuously measuring oxygen profiles in a 3D cell aggregate 14 comprised of cancer stem cells, oxygen-dependent differentiation pathways for cancer cells can be studied.

In still further instances, the measured response(s) can be used to identify new therapeutic agents, such as small molecules or pharmaceutical compounds. Where, for example, the measured responses indicate good cell viability at one or more of 3D cell aggregate 14 regions having low oxygen status for a particular test agent, the agent may be a promising candidate for further investigation as a therapeutic agent (e.g., using an in vivo model).

In another aspect, the measured response(s) can be used to predict whether a patient will respond to a therapeutic strategy. In a patient suffering from cancer, for example, neoplastic cells can be harvested from the patient and then used to form the 3D cell aggregate 14 of the system 10. A number of test agents (e.g., chemotherapeutic agents) can then be contacted with the system 10, followed by measurement of one or more responses of the 3D cell aggregate 14. For example, where the measured responses indicate good cell viability at one or more of 3D cell aggregate regions with low oxygen status, a predication can be made that the particular test agent will have a positive therapeutic effect when administered to the patient. Consequently, an individual therapy for the patient can be designed or selected based on the measured response(s).

Advantageously, the system 10 of the present disclosure can find numerous applications in the cancer drug development and screening industry. For example, the thin film MEMS version of the system 10 can be fabricated at low cost and high throughput for use in the drug screening industry. Additionally, the present disclosure can bridge the gap between current in vitro drug screening modalities and pre-clinical animal testing by providing an in vitro multicellular 3D screening platform, which may accelerate the rate at which new drugs become available for different cancers. The results can also be used with primary cell constructs for personalized therapy design. Further, basic studies on drug transport and accompanying changes in oxygenation, pH, and other parameters can be enhanced with the present disclosure.

The following examples are for the purpose of illustration only and are not intended to limit the scope of the claims, which are appended hereto.

Example 1

Measuring Oxygenation Status in Multicellular Tumor Spheroid Models with a Microelectrode Array Experimental
Cell Culture MCF7 doxorubicin resistant (MCF7-R) cell line was acquired from The University of Texas, M. D. Anderson Cancer Center, Texas, USA. MCF7 cells were maintained and propagated in DMEM containing 10% FBS and penicillin-streptomycin in tissue culture dishes (Fisher Scientific). Cells were incubated at 37° C. in 5% $CO_2$ environment.

3D Multicellular Model Agar Half Spheroids

Confluent plates of MCF7-R cells ere trypsinized and collected in a sterile 1 mL vial. The cell density and the total number of cells in the vial were estimated by cell counting using a hematocytometer. The cells were spun down in a centrifuge and the supernant medium removed. A known volume of 1% agarose type VII-A (low gelling temperature) was added to the cells and mixed well to attain the desired cell density, 0.3 million cells/μL in this case, for model agar spheroid. The vial with the cell-agar mixture was constantly kept in water bath at 37° C. to prevent the agar from gelling. Tiny hemispherical droplets (800-1000 μm diameter) of this mixture were deposited onto a Teflon® sheet using 0.5-2.5 μL pipette (Eppendorf, Hauppauge, N.Y.) to obtain hemispherical multicellular model agar spheroids. The Teflon® sheet with the model agar half spheroids was incubated in culture medium used for MCF7-R cell culture at 37° C. in 5% $CO_2$. Henceforth, model agar half spheroids will be referred to simply as half spheroids.

Apparatus
Gold Microdisc Electrode Array

A radial gold (Au) electrode array with five microdisc electrodes for oxygen measurement inside half spheroid was fabricated. Au wires, 2 inch in length and 50 μm in diameter were insulated with 30 μm thick Parylene using a Parylene vapor depositor. The insulated wires were aligned to run parallel to each other under a stereo microscope. The aligned wire arrangement was then set in non-conducting epoxy resin to obtain the electrode array of Au microdisc electrodes, E1 to E5 (FIGS. 8A-E). The other ends of the Au wires were connected to macro wires via conducting epoxy (Circuitworks, CW 2400). The whole assembly was then embedded in a glass slide using non-conducting epoxy resin for stability. A reservoir for electrolyte around the electrode array was built by fixing the glass assembly inside the Petri dish using silicone elastomer. For isolation of electrical circuitry from aqueous test solutions, the wires were routed through a leak proof hole at the bottom of the Petri dish to the potentiostat.

Instrumentation

A CHI 1030 8-channel potentiostat (CH Instruments Inc., Austin, Tex.) was used to perform all electrochemical experiments. The experimental setup was placed inside a custom built Faraday cage. A Scion camera was mounted on top of the Faraday cage for visual observation of the electrode array. The array of five Au microdiscs (working electrodes) was used for interrogating oxygen concentration inside the spheroid. An Ag/AgCl with 4M KCl filling solution (BAS Inc., West Lafayette, Ind.) and a stainless steel wire was used as reference and counter electrodes, respectively. The reference and counter electrodes were common to all the Au electrodes. 7.4 pH phosphate buffered saline (PBS) without glucose was used as electrolyte unless otherwise mentioned.

Chemicals and Cell Culture Reagents

Dulbecco's modified Eagle's medium (DMEM) was purchased from Mediatech Inc. (Manassas, Va.), fetal bovine serum (FBS) and trypsin from Hyclone (Logan, Utah) and penicillin-streptomycin from MP Biomedicals (Solon, Ohio). Analytical grade 1×PBS buffer, sodium azide (NaN3), 2,4 dinitrophenol (DNP) and agarose type-VIIA used for cell experiments were bought from Fisher Scientific (Pittsburgh, Pa.) or Aldrich (St. Louis, Mo.). Quartz distilled water (18 MΩ·cm) was used to prepare all solutions.

Experimental Protocol and Relevant Procedure

The Au microdisc electrodes were polished using a fine emery paper to expose fresh electrode surface before each experiment. The polished electrodes were rinsed with DI water and allowed to dry in air (~1 hour) after which a thin (~10 μm) layer (spacer) of cellulose acetate was deposited. The electrodes were pre-conditioned electrochemically prior to starting the half spheroid experiment by continuous cyclic voltammograms (CV) until a stable measurement was reached (at least 50 CVs). The electrodes were calibrated for oxygen reduction current in PBS at different oxygen concentrations prior to the half spheroid experiment (henceforth, referred to as pre-calibration). A half spheroid was positioned on top of the electrode array and the oxygen concentrations inside the spheroid interrogated by linear scan voltammetry (LSV). Oxygen reduction currents under the half spheroid were recorded for half an hour after which the viability of cells inside the half spheroid was checked by pharmacological modulation of cellular oxygen consumption by administering metabolic poisons—$NaN_3$ and DNP. At the end of the experiment the spheroid was removed and current corresponding to ambient oxygen concentration was recorded. The spheroid experiment was followed by a post experiment calibration (henceforth, referred to as post-calibration) of the electrodes to check for electrode drift. The LSV data recorded during these experiments was post processed to extract oxygen concentration values under the spheroid.

Cellulose Acetate Protective Layer

Figure 8:
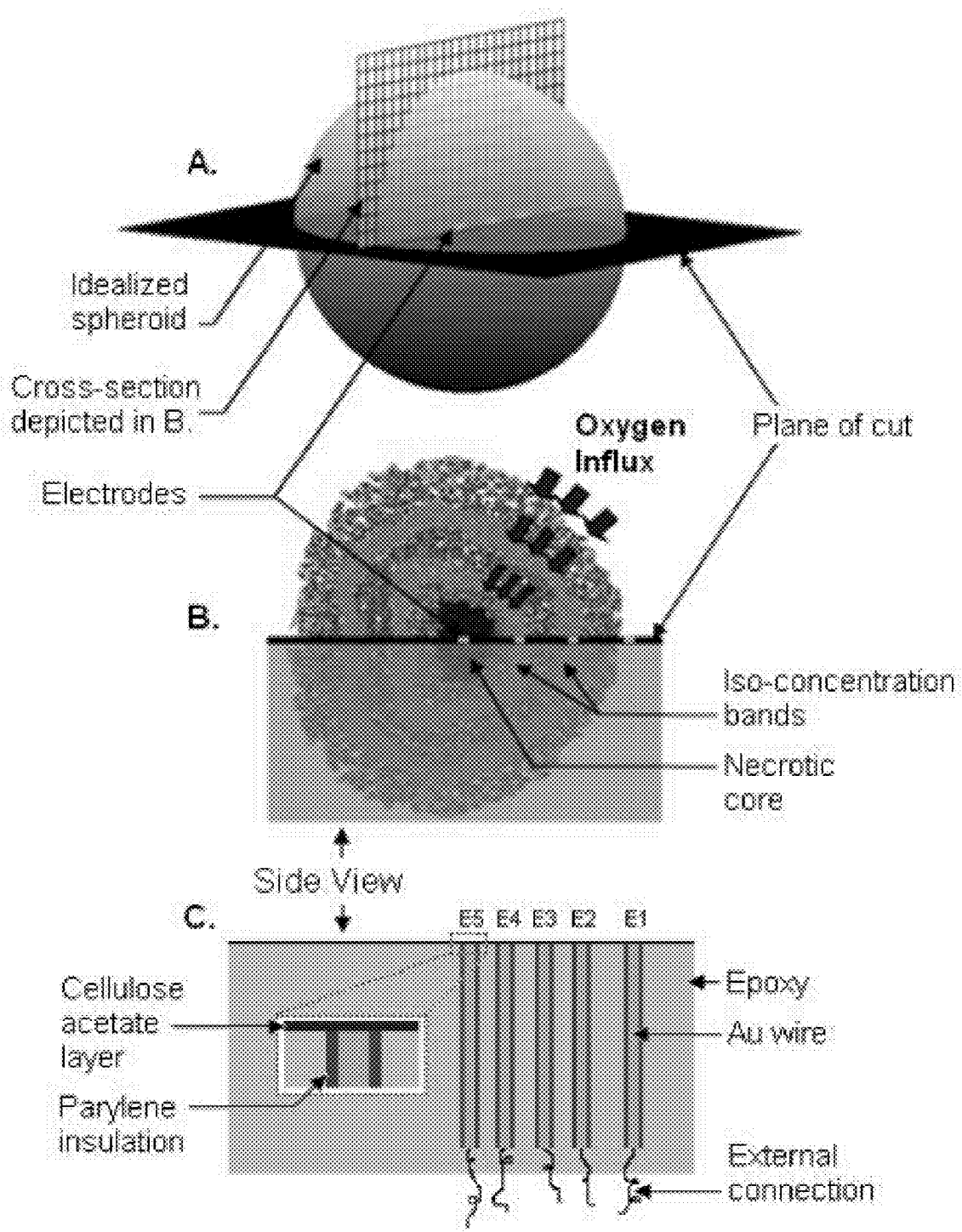
FIGS. 8A-E illustrate a measurement approach according to one aspect of the present disclosure.
Figure 8:
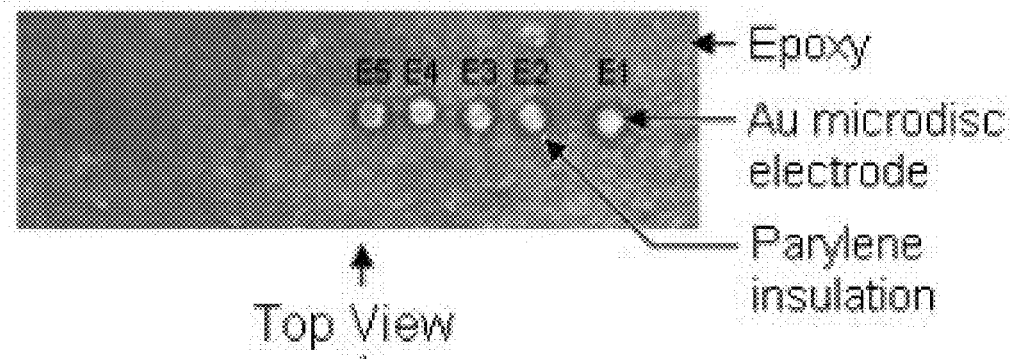
Figure 8:
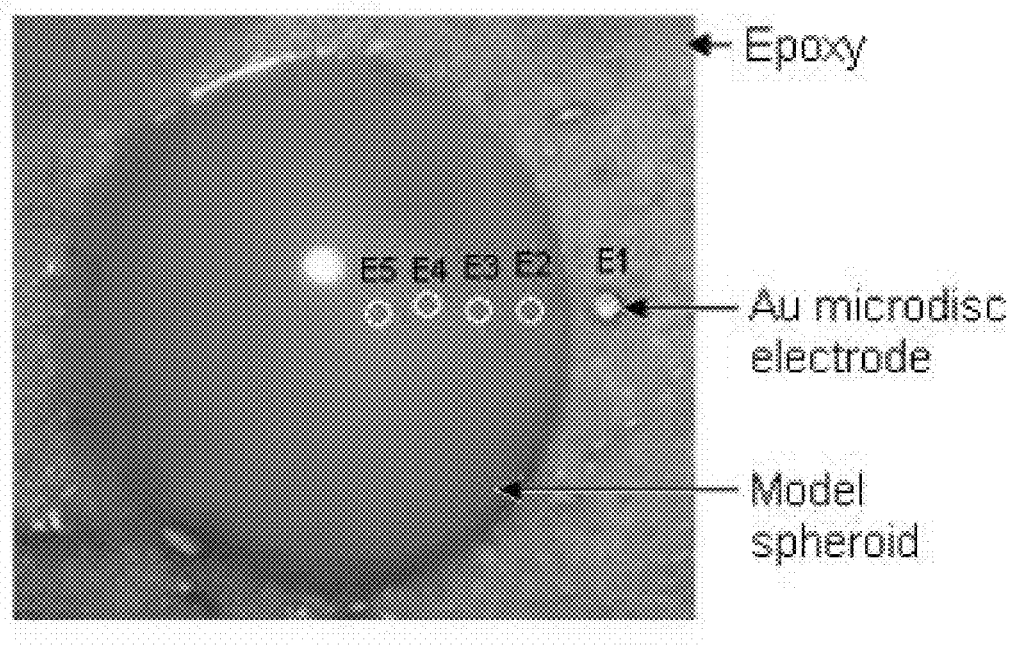

1 μL drop of 1% cellulose acetate hydrogel in 1:1 mixture of acetone and cyclohexanone was deposited on the electrode array and allowed to dry for an hour creating 8-10 μm thin hydrogel layer on the electrodes. This can be seen in the side view schematic (FIG. 8C). The electrode assembly coated with the dry hydrogel layer was rinsed with DI water and then hydrated in PBS for an hour before each experiment.

Preparation of Test Solutions for Calibration $N_2$ gas was bubbled in air-equilibrated PBS for a minimum of 30 minutes to purge oxygen from buffer. After 30 minutes of bubbling oxygen concentration was considered to be nominally zero. From this point on, PBS with nominally zero oxygen concentration will be referred to as oxygen-depleted buffer. Oxygen level in the test solution was varied by adding oxygen-depleted buffer or air equilibrated buffer, respectively to decreased $O_2$ level from 21% to ~5% and back up to ~20%. After each addition the test solution was homogenized by mixing the solution using a pipette for ~10 s. Corresponding oxygen concentration of the test solution was measured by a Clark-type oxygen electrode (Microelectrode Inc., Bedford, N.H.). Addition of PBS and homogenization was done in 2 minutes between sets of consecutive LSVs (3 LSVs per set).

Positioning of the Half Spheroid on the Au Electrode Array

The Teflon® sheet on which half spheroids are was is removed from the incubating medium. A half spheroid was carefully transferred onto the electrode array using a curved edge of a pair of tweezers such that the radial electrode array was aligned along a spheroid radius (FIG. 8E). The positioning was done under a 2× stereo microscope to ensure that the spheroid is resting on its flat (bottom) edge. After the agar spheroid was positioned at the desired location a drop of low gelling agarose made in PBS maintained in liquid form at 37° C. was dispensed onto the spheroid from the top to secure its position and prevent it from moving with convective flow. PBS was added to the measurement device reservoir immediately after the spheroid position was secured. The time taken to position the spheroid from the time the half spheroid Petri-dish was removed from the incubator to the time when oxygen measurement is started is less than 3 minutes. During this time the cells in the spheroid (except the outer most shell) were not directly exposed to air.

Addition of Pharmacological Drugs and Glucose for Oxygen Consumption Modulation

Desired volumes of the $NaN_3$, DNP and glucose solutions were gently added to the test solution using a disposable transfer pipettes. The solution was then homogenized by gentle circular movements induced by the same pipette for ~10 s.

Removal of the Spheroid

The spheroid was removed from top of the electrode array by using convective flow. A thin tip disposable pipette was used to precisely direct a stream of buffer towards the spheroid with high enough flow velocity to detach it from the base.

Measurement Protocol

Inbuilt cyclic voltammetry (CV) and linear scan voltammetry (LSV) techniques in CHI1030 were used for electrochemical cleaning and electrochemical interrogation of oxygen, respectively. LSV was used as the measurement technique for all the experiments. All LSVs were performed from 0.4 V to –1.2 V at 100 mV/s scan rate and 100 Hz sampling rate. Electrode calibration was done by consecutive LSVs performed every 2 minutes. LSVs under half spheroid were recorded every 7 seconds. A CHI1030 macro program was written to automatically start measurements after the allotted quiet time for all the experiments.

Data Processing

All the LSV data recorded during the experiments was post processed using Matlab 7.9.0. Numerical differentiation using first derivative Savitzky-Golay FIR quadratic smoothing filter with 25 points differentiation window was used to obtain oxygen reduction peak currents from LSVs and consecutively oxygen concentrations under the spheroid. The details of the measurement protocol, its optimization and data processing are described in depth below.

The oxygen concentration peak differential currents calculated from calibration experiments were used to obtain linear pre- and post-calibrations. Pre-calibration was used to obtain oxygen concentration under the spheroid for the initial part of the experiment with only PBS and for $NaN_3$ addition. $NaN_3$ does not alter the differential current peak height for oxygen. Post-calibration was used to obtain oxygen concentrations from the differential current peaks from the time of DNP addition. The phenol group of DNP was electrochemically active and is reduced at potentials more negative than oxygen reduction potential. The activity of DNP slightly alters the position of the oxygen reduction peak on the voltage axis and also the height of the peak.

Statistical Analysis

Standard deviation of the peak currents for each pre-calibration data set was calculated considering the linear regression of calibration as true value. 95% confidence interval around the linear calibration was estimated using Students t-test. Finally, we checked if the post-calibration data resided in the estimated confidence interval to be able to tell with 95% certainty if the two calibrations were similar or not.

Measurement Approach

The spherical symmetry of the multicellular tumor spheroid (MCTS) models was used in this sensing approach. Owing to this spherically symmetric concentration profiles, one can map oxygen concentrations inside the entire spheroid by electrochemically measuring concentrations along a single radius as shown in FIG. 8A.

To get access to the radial concentrations, an equatorial plane of the spheroid needs to be exposed. This is accomplished by making 3D hemispherical cellular constructs—half spheroids (see methods for details). The equatorial plane provides a "window" into the interior of the spheroid. The equatorial plane of the half spheroid is put face down, flush with the impermeable substrate where the Au microdisc electrode array is fabricated. The half spheroid is positioned on top of the electrode array for oxygen measurement. The measured value by a given oxygen microelectrode is representative of an entire "shell" of cells at the depth of that particular sensor.

Estimation of Absolute Flux and Oxygen Consumption

Oxygen concentration inside a spheroid reaches quasi steady state oxygen consumption within minutes of starting the experiment prior to the glucose deprivation phase because of the small radius of the spheroid, R≈500 μm, and relatively fast coefficient of diffusion, D≈2000 μm2/s in PBS (t<R2/D≈2 minutes). Therefore, cellular oxygen consumption inside spheroids can be quantified considering the quasi steady state oxygen concentrations measured using the Au electrode array prior to the addition of pharmacological modulators. Considering the spherical symmetry of the spheroid we can define the steady state diffusion-consumption problem by the following differential equation (2.1).

$$D\left(\frac{\partial^2 C}{\partial r^2} + \frac{2}{r}\frac{\partial C}{\partial r}\right) = q(r) \quad (2.1)$$

where:
C=concentration of oxygen;
r=distance from the center of the spheroid;
D=diffusion coefficient; and
q=rate of cellular consumption.

We divide the complete steady state oxygen concentration problem into two compartments, PBS surrounding the spheroid (r>R) and the spheroid itself (0≤r≤R) because of different consumption constraints in each region. The consumption, q, in PBS outside the spheroid is zero because of the absence of cells in this region. Therefore, the concentration of oxygen in PBS is estimated from the hyperbolic solution of the steady state spherical diffusion problem given in equation (2.1). Considering the steady state concentration at E1 and the bulk oxygen concentration of 20% in equilibrium with the ambient atmosphere at 1 atmospheric pressure and 25° C., the concentration profile in PBS is given as:

$$C_m(r) = C_s - \frac{r_{E2}(C_\infty - C_{E1})}{r} \quad (2.2)$$

Figure 9:
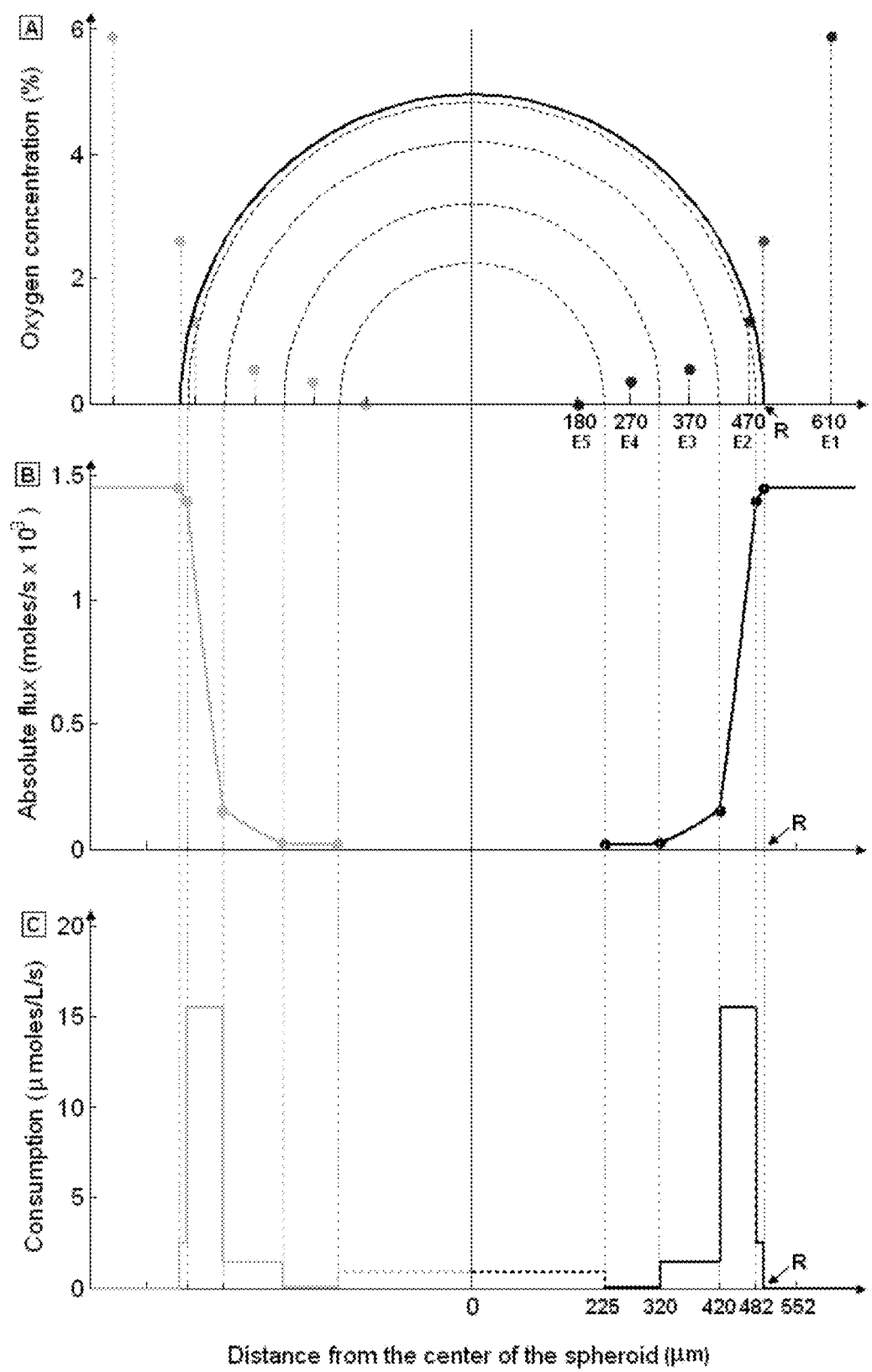
FIGS. 9A-C shows quasi steady state oxygen concentrations measured along a radius of a half spheroid with the measurement approach and the corresponding estimated fluxes and cellular rate of oxygen uptake inside the half spheroid shells. Measured concentration (•) at the surface of Au microdisc electrodes E1 to E5. (•) represents the concentration estimated at the surface of the half spheroid (R=495 µm) using hyperbolic steady state concentration profile obtained using concentration measured at E1 outside the spheroid and the concentration at a distance far from the spheroid (~20%). Each electrode defines an equiconcentration shell with boundaries depicted by (---). The fluxes (FIG. 9B) at each shell boundary, midpoint between two adjacent electrodes, are estimated by considering quasi steady state concentration gradients between them. Idealized half spheroid shell boundaries (---) where the fluxes are estimated for the half spheroid (FIG. 8E) are shown. Absolute oxygen flux (moles/s) entering each shell of the model spheroid (•) estimated from the concentration gradients is shown. The absolute oxygen flux for r>R is constant because of the absence of any consuming cells. Large drop in oxygen flux is estimated for the second shell from outside. Oxygen flux in subsequent shells (3 & 4) decreases until the flux becomes zero when all the oxygen molecules entering the spheroid are consumed. Oxygen consumption rate (µ moles/L/s) estimated for each of the shells of the half spheroid is shown. The consumption rate outside the spheroid (r>R) is zero because of the absence of cells. The consumption estimated from the difference between the incoming and outgoing oxygen fluxes for each shell is assumed to be constant for that shell.

Using equation (2.2) we can calculate the concentration of oxygen, CR, just outside the edge of the spheroid, $R_+$ (FIG. 9A). The absolute flux, total amount of oxygen molecules moving towards the spheroid in PBS and that entering the spheroid per second, is constant because of zero consumption in this region. Therefore, the absolute flux is quantified by equation (2.3).

$$F_m = D_m A_R \frac{dC_m}{dr} = D_m A_R \frac{r_{E1}(C_x - C_{E1})}{r^2} \quad (2.3)$$

where:
$C_m$=oxygen consumption in PBS;
$C_\infty$=bulk oxygen concentration;
$C_{Ei}$=oxygen concentration measured at electrode Ei, i=1 to 5;
$r_{Ei}$=radial distance of Ei from the center of the spheroid, i=1 to 5;
$D_m$=diffusion coefficient of oxygen in PBS;
$A_r$=surface area of the spheroid.

The differential equation (2.1) cannot be analytically solved for the spheroid compartment because we do not know the rate of cellular oxygen consumption. Therefore, the absolute flux moving inside the spheroid from one shell to the other is estimated by using discrete numerical difference method using the quantified oxygen concentration at R and the measured oxygen concentrations at E2 to E5. From the definition of diffusive flux density given by (2.4) we can estimate the absolute flux crossing the boundaries of the subsequent shells per second by (2.5):

$$J = D_s \frac{\Delta C_s}{\Delta r} = \frac{F}{A} \quad (2.4)$$

$$F_i = D_s A_i \frac{\Delta C_s}{\Delta r}\bigg|_{i+1}^{i} \quad i = 1, 2, 3, 4, 5 \quad (2.5)$$

where:
J=flux density;
$D_s$=diffusion coefficient inside the spheroid;
$\Delta C_s/\Delta r$=concentration gradient along the spheroid radius;
$F_i$=absolute flux crossing the shell boundary between shells i and i-1;
$A_i$=surface area of the shell boundary between shells i and i-1;
$C_{s1}=C_R$; and
$C_{si}=C_{Ei}$, i=2 to 5.

The value of Ds is assumed to be 70% of the diffusion coefficient in PBS which is 2000 μm²/s (Macdougall and McCabe 1967). This is because the volume occupied by the cells inside half spheroids made with 0.3 million cells/μL cell density is equivalent to 30% of the total volume of the half spheroid, cell volume fraction, (cell diameter is assumed to be 10 μm). The remaining 70% of the spheroid volume is made of agar and the diffusion coefficient of oxygen in agar is very similar to that in PBS.

The loss of oxygen molecules per second inside each shell is obtained by taking a difference between the two consecutive fluxes, the incoming flux into a shell and the outgoing flux from that shell. The loss of oxygen is nothing but the total amount of oxygen consumed per second by the cells in that shell. The total consumption for each shell normalized by the shell volume gives the per volume oxygen consumption. Henceforth, this will be referred to as per volume $O_2$ consumption.

$$q_i = \frac{\Delta F}{\Delta A}\bigg|_{i+1}^{i} \quad i = 1, 2, 3, 4 \quad (2.6)$$

Results

Radial array of five gold microdisc electrodes, each 50 μm in diameter and insulated with Parylene, was fabricated as described above (FIGS. 8C-D).

Calibration of the Au Microdisc Electrode Array

Figure 10:
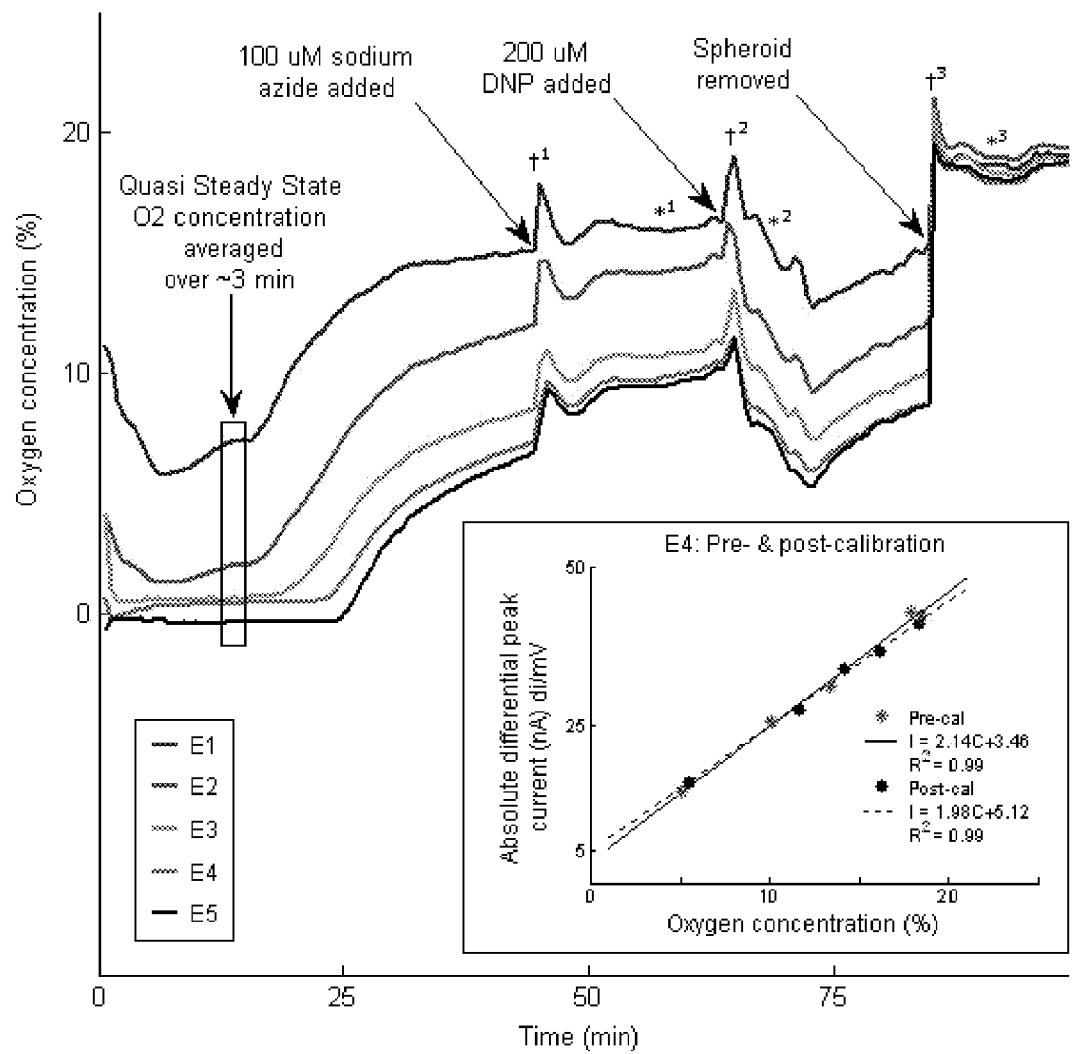
FIG. 10 is a graph showing oxygen concentrations (%) measured continuously at electrodes E1-E5 over a period of ~100 minutes under a model spheroid (cell density ~0.3 million cells/µL, diameter ~1 mm, shown in FIGS. 8A-E). Increase in the measured oxygen concentrations (*1) at the Au microdisc electrodes is seen after the addition of sodium azide (100 µM final concentration). Rapid decrease in the oxygen concentrations (*2) is measured with the subsequent addition of 2,4-dinitrophenol (DNP 200 µM final concentration). The removal of the spheroid returned the measured oxygen concentrations to ambient oxygen concentrations ~20% (*3). Short oxygen concentration peaks seen immediately after the addition of sodium azide (†1), DNP (\2) and removal of the spheroid (\3) is attributed to the convective flow created during each of these procedures. (Inset: calibration of differential peak current (nA/mV) versus oxygen concentration (%) for electrode E4). (*) represents the differential current peak values obtained for pre-calibration and (•) represents the values for post-calibration. Linear regression fit for both pre-calibration (solid line) and post-calibration (dashed line) are shown.

The LSV protocol for oxygen measurement was used to simultaneously obtain down-up calibrations (pre- and post-experiment) of oxygen reduction electrode peak current vs. oxygen concentration for all the five Au microdisc electrodes. Oxygen reduction peak differential currents obtained using the numerical differentiation protocol (above) were plotted against the measured oxygen concentrations from Clark-type oxygen electrode to construct linear calibrations. A linear regression fit was obtained for each electrode. A representative calibration (pre- and post-) curve for E4 is shown in FIG. 10. The sensitivities, regression coefficients and residual errors for all the electrodes are given in the Appendix I.

Oxygen Concentration Under a Half Spheroid

A half spheroid with 30% cell volume fraction was positioned on top of the radial array of calibrated Au electrodes (FIG. 8E) and oxygen concentration at different depths inside the half spheroid was measured. A decrease in the measured oxygen concentrations under the spheroid was seen with decreasing radius (closer to the center of the spheroid). The time sequence oxygen concentrations obtained during a representative experiment is shown in FIG. 10.

Oxygen concentrations measured under the model spheroid reached quasi-steady state (QSS-1) oxygen concentrations after an initial (~5 minutes) rapid decrease of oxygen concentration. After a short period of QSS-1 a rapid increase of oxygen concentrations under the model spheroid began, starting from electrode E1 followed sequentially by the rest of the electrodes resulting in a second quasi steady state (QSS-2) oxygen concentrations. The electrode closer to the boundary of the spheroid started increasing before the ones located deeper inside the spheroid.

Pharmacological and Physical Manipulation of the Spheroid

To check for the viability of MCF7-R cells inside the half spheroids the response of the cells oxygen consumption to the effect of metabolic poisons was recorded using the Au microelectrode array. Oxygen concentrations measured by all the Au electrodes increased after the addition of 100 μM sodium azide (FIG. 10: *1) and decreased rapidly after the addition of 200 μM DNP (FIG. 10: *2). At the end of the experiment the spheroid was removed. An increase in the stable oxygen concentration values to ambient oxygen concentration (~20% $O_2$) were recorded after the spheroid was removed from top of the electrodes. The approximate oxygen concentrations reached after the addition of $NaN_3$ and after removal of the half spheroid are given in Appendix I.

Estimated Flux and Oxygen Consumption During QSS-1

Figure 11:
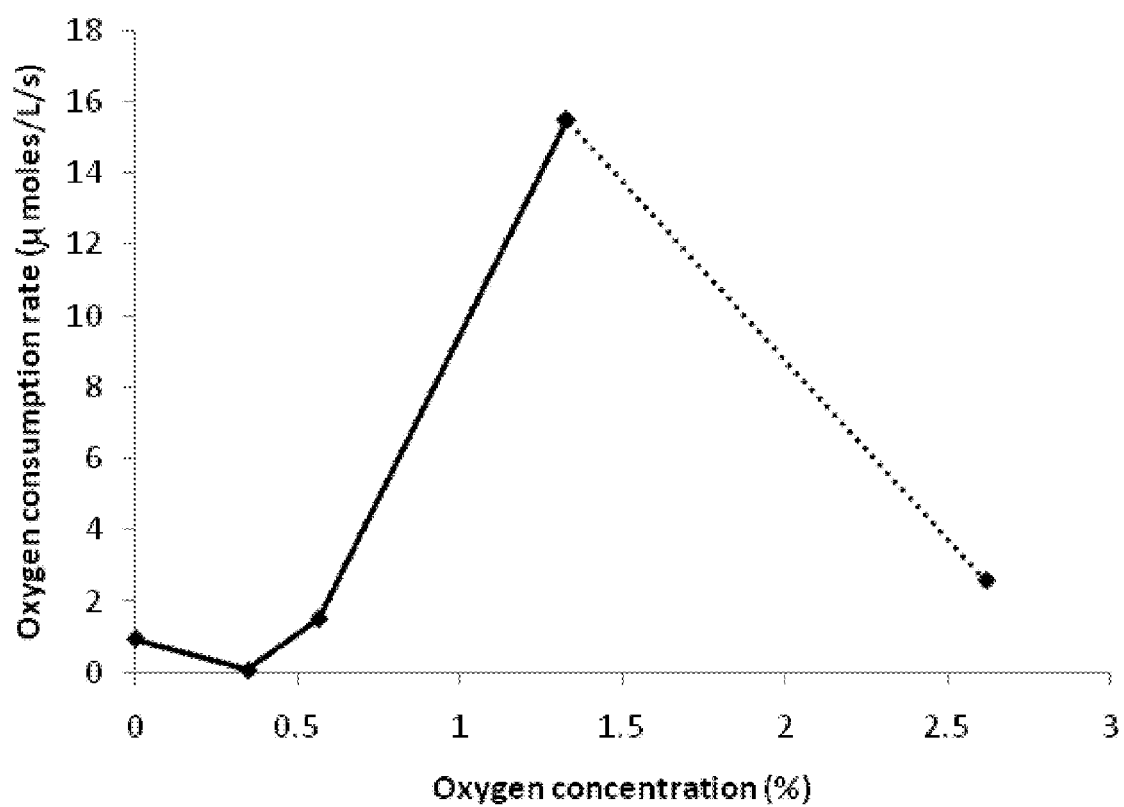
FIG. 11 is a graph showing oxygen consumption rate (µ moles/L/s) as a function of decreasing oxygen concentration inside the half spheroid (FIG. 8E)

Absolute oxygen flux (moles/s) and oxygen consumption in the model spheroid shells (μ moles/pL/s) entering the spheroid were estimated from the measured concentrations at the Au electrode surface (FIG. 9A). The amount of oxygen moving towards the model agar spheroid in the buffer which does not house any live cells and that entering the spheroid (r>R) was constant (~1500 moles/s for the representative experiment). The corresponding oxygen consumption q in this region was zero because of absence of cells. The flux moving through the spheroid shells was estimated numerically by calculating the concentration gradient at the boundary of each shell decreases as we move towards the center of the half spheroid (FIG. 9B). Per volume oxygen consumption obtained inside each shell also decreased towards the center of the half spheroid (FIG. 9C). Per volume rate of cellular oxygen consumption was found to be monotonically decreasing with the shell oxygen concentration (FIG. 11).

Discussion

Oxygen Calibration

Linear calibrations of oxygen reduction peak current vs. oxygen concentration are obtained showcasing the capability of the numerical differential of LSV method. The residual error for all the electrodes in terms of oxygen concentration is less 0.7%. The slight decrease in the sensitivities of post-calibration from the pre-calibration for all the electrodes is the effect of these electrodes coming in contact with cells. The cell clad half spheroid sitting on top of these electrodes causes minor electrode fouling. However, the current values estimated from the post-calibration for the $O_2$ concentration range of 0 to 21% were found to lie within the 95% confidence interval of the pre-calibration values for all the electrodes.

Spheroid Experiment

Diffusion limitation of oxygen along with its rapid consumption by the MCF7-R cells inside the spheroid results in less than ambient oxygen concentration inside and in the vicinity of the spheroid (FIG. 10). Small size and radial symmetry of the spheroid, finite consumption and diffusion rates along with continuous replenishment of oxygen in the bulk PBS results in the development of steady-state oxygen concentrations in short time. Because of the similarity in the geometry of the spheroid and a spherical microelectrode, the steady state oxygen concentration profile developed outside the spheroid with no consuming cells should be similar to the hyperbolic profile developed outside the electrode. The difference in the two consuming bodies is that the concentration at the surface of the electrode is fixed at zero, assuming kinetically fast reduction of oxygen, but the concentration at the spheroid surface is non-zero. This is because $O_2$ consumption for the spheroid is finite and is not restricted to the outer surface but is prevalent throughout the non-necrotic region of the spheroid. Oxygen concentrations are measured using the developed device platform (FIG. 10). The initial decrease in the oxygen concentration at the beginning of the experiment is attributed to a combination of two factors: 1.) initial oxygen transient before a quasi steady-state is reached, 2.) renewal of the electrode surface after a short period of quiescence during which no potential is applied on the surface. QSS-1 concentrations measured in shells defined by electrodes E1-E5 decrease as we go deeper into the spheroid. This manifests from a composite effect of decreased supply of oxygen due to diffusion limitation and consumption of oxygen in the spheroid shells. However, the development of a quasi-steady-state indicates that the rate of oxygen consumption in each shell is equal to the rate of supply by diffusion. This also elucidates a decrease in the cellular rate of oxygen consumption as we move towards the center of the spheroid which is explained in detail later.

The oxygen concentration a few hundred micrometers outside the spheroid (at E1) is found to be ~6% for our experiments with 30% cell volume fraction spheroid (n=2). This results from the hyperbolic decrease of concentration governed by the intensity of oxygen consumption by the spheroid as a whole unit. The change in the steady state per volume rate of oxygen consumption inside the spheroid is reflected upon the resulting concentration measured at E1. This is proved by experiments with lower density of cells embedded inside the half spheroid. With 15% cell volume fraction spheroid oxygen concentration at E1 increased to ~10% (n=3, Appendix III). Because of the lack of cells in the shell formed between the boundary of the spheroid and E1 ($R \leq r \leq R_{E1}$) the hyperbolic concentration profile is valid in this region. Extrapolating the purely diffusive hyperbolic profile, a concentration of ~3% is obtained at the surface of the spheroid (FIGS. 9A-C (•)).

The concentrations at E2-E5 are the result of both diffusion of oxygen across the shell and consumption in the shell. Measured concentration at E5 is approximately zero signifying a zero concentration core of the spheroid. Anoxic region created ~100 μm inside the half spheroid with only 30% cell volume fraction with 20% ambient $pO_2$ is the proof of diffusion limitation of oxygen. Bigger molecules such as glucose and drugs which even lower diffusion coefficient therefore, would be resigned to the same fate with even severe concentration heterogeneity. The findings in this work therefore, support the theory of multicellular drug) resistance, a cumulative mechanism resulting from the physical structure of the tumor tissue. Similar to the concentration at E1 outside the spheroid, the concentration of oxygen inside a spheroid also depends on the density of the cells (Appendix III).

Oxygen Consumption Modulation Due to Activation of Glucose Deprivation Transcriptional Pathways The rapid increase of oxygen concentration observed between 15-30 minutes into the experiment is attributed to glucose deprivation inside the spheroid. The half spheroids are incubated in cell culture medium containing 25 mM glucose prior to the experiment causing the cells in the half spheroid to be equilibrated with 25 mM glucose. During the measurement the spheroid is kept in pH 7.4 PBS without glucose. Thus, the glucose inside the cells and in the extracellular agar is either consumed or it diffuses out into the surrounding PBS resulting in fast glucose deprivation. Lack of glucose is associated with the AMP-activated protein kinase (AMPK) metabolic regulatory pathway. Insufficient glucose leads to slowing of ATP formation resulting in accumulation of AMP which leads to AMPK activation. AMPK turn of different transcriptional pathways for cells to correct the low ATP situation. It slows down the activity of cells by inhibiting cell cycle progression and starts the deployment of glucose transporters and glycolytic enzymes. For our experiment it is most likely that the increase in oxygen concentration inside the spheroid is caused by secession of cell activity. The switching in glucose metabolism requires the cell to make the required enzyme and transporter molecules which takes longer than 30 minutes, which is more than the time of oxygen concentration increases. The increase in the oxygen concentration starts at E1 because of the faster rate of consumption (more oxygen available) and faster rate of diffusion) resulted in an almost instantaneous decrease of measured oxygen concentrations for all the electrodes, which confirmed our conclusion.

Modulation of oxygen consumption by metabolic poisons such as $NaN_3$ and DNP confirm the viability of the MCF7-R cells embedded in the half spheroid. Addition of 100 μM $NaN_3$ (final concentration) causes the oxygen consumption by the cells to slow down by inhibiting cytochrome C oxidase in the electron transport chain (ETC) resulting in increased oxygen in the vicinity of the cells. This increase is measured by the electrodes (FIG. 10: *1). Subsequent addition of 200 µM DNP (final concentration) results in rapid increase of oxygen consumption due to the uncoupling of ETC and ATPase by negating the proton gradient. The increase in oxygen consumption by the MCF7-R cells translates into decreased oxygen in the vicinity of the cells which is measured by the electrodes (FIG. 10: *2). The changes seen in oxygen concentration with both these drugs also confirm no or minimum fouling of the electrodes. Removal of the half spheroid from top of the electrode array resulted in the measured oxygen at all the electrodes to increase and return to ~20%, the concentration of air equilibrated surrounding PBS.

Oxygen Flux and Consumption

The absolute flux entering the spheroid from the surrounding PBS and traversing the subsequent spheroid shells gives an estimate of the rate of oxygen consumption inside each shell. The cellular consumption of oxygen in the region r>R is zero because of the absence of live cells in this region. Therefore, the total flux moving across this region in steady state is constant (FIG. 2.3B). Considering the hyperbolically decreasing concentration profile for spherical geometry and the bulk concentration of 20% at a distance far from the spheroid, the amount of oxygen entering the spheroid, constant in time, is calculated to be 1500 moles/s for 30% cell volume fraction spheroid. The absolute flux moving inside the spheroid, from one shell to the next, decreases successively because of the consumption by the MCF7-R cells (B). The maximum drop in the estimated flux is seen the 2nd shell of the spheroid just inside the boundary of the spheroid representing maximum consumption in that shell. The subsequent shells going inside towards the center of the spheroid receive the remaining oxygen via diffusion resulting in much lower oxygen concentrations in those shells. Slower rates of consumption seen in these shells (C) indicate the dependence of the rate of consumption on the extracellular oxygen concentration. Per volume consumption obtained in the first thin shell is lower than that in the second shell. This is thought be the result of the thinness of the first shell which is ~25 µm, smaller than the diameter of the electrode. The consumption in the core of the spheroid (r≤225 µm) is estimated to be non-zero from flux calculations (C (---)), which is attributed to measurement error and also instrumentation error because of the lack of measurement electrodes in this region.

The monotonically decreasing relationship of the oxygen consumption with the measured extracellular oxygen concentration in the range of ~0 to 1.25% (FIG. 11) suggests that the mechanism of oxygen consumption is dependent on the oxygen concentration. However, the relationship between the rate of oxygen consumption and oxygen concentration for a cell as an entire unit is not known. Michaelis-Menten kinetics for individual enzymes utilizing oxygen as substrate or co-substrates has been investigated in a fractional approach. Therefore, we expect the oxygen consumption-concentration relationship to be non-linear, a combination of Michaelis-Menten enzyme kinetics for all oxygen consuming enzyme mechanisms in the cell. For example, the $K_m$ values for cytochrome c oxidase and propyl hydroxylase, only two oxygen consuming mechanisms, are found to be 0.9 µM and 250 µM, respectively, which are two orders of magnitude apart. Therefore, the consumption-concentration relationship is expected to be non-linear. Currently, because of the preliminary nature of the measurement data sets and lack of sufficient repeats of these experiments we cannot approximate the form of this relationship with certainty. Experiments with higher spatial resolution need to be done to further investigate the relationship between oxygen consumption and concentration for the entire cell.

Example 2

Modeling of Oxygen Concentration as a Function of the Rate of Consumption Inside Multicellular Tumor Spheroid Experimental
Cell Line, Instrument and Half Spheroid Oxygen Concentration Experiment MCF7 doxorubicin resistant (MCF7-R) cells line were maintained and propagated in DMEM containing 10% FBS and penicillin-streptomycin in tissue culture dishes (Fisher Scientific). Cells were incubated at 37° C. in 5% $CO_2$. Model agar half spheroids were made by mixing MCF7-R cells in 1% agar at 37° C. and casting 1 mm hemispheres on Teflon® sheet (as described in Example 1).

Gold multielectrode array platform with 5 microdisc electrodes was used to measure oxygen concentration under the half spheroids. Ag/AgCl reference, stainless steel counter and pH 7.4 PBS electrolyte were used. A CHI 1030 8-channel potentiostat (CH Instruments Inc., Austin, Tex.) placed inside a Faraday cage was used for oxygen measurements. Absolute oxygen flux moving across the spheroid shells and variable rate of oxygen consumption in these shells were calculated using a numerical difference technique (see Example 1).

Data Processing

Matlab 7.9.0 was used for data analysis and model simulations.

Theory

The spherical shape of the spheroids results in radially symmetric concentration distribution of oxygen in and around the spheroids. Therefore, comprehensive information about the concentration distribution can be obtained by solving for oxygen concentration along a single radius (Example 1).

The rate of change of radial oxygen concentration depends on the rate of diffusion of oxygen and rate of loss of oxygen by cellular consumption. Therefore, the overall problem of oxygen concentration can be defined by differential equation (3.1).

$$\frac{\partial C}{\partial t} = D\left(\frac{\partial^2 C}{\partial r^2} + \frac{2}{r}\frac{\partial C}{\partial r}\right) - q(r) \quad (3.1)$$

where:
C=oxygen concentration;
t=time;
r=radius;
D=diffusion coefficient; and
q(r)=rate of oxygen loss by consumption along the radius.

Because of the radially symmetric concentration distributions and constant replenishment of oxygen in the surrounding medium a steady state concentration profile is reached within 3 minutes (time to steady-state, $t=R^2/D_s$, where R is the radius of the spheroid, 500 µm, and $D_s=0.7*D_m$ is the coefficient of diffusion inside the spheroid, 1400 µm²/s) of starting the experiment. Thus, the rate of diffusion becomes equal to the rate of loss of oxygen by consumption.

In the medium surrounding the spheroid, the rate of loss of oxygen is zero because of the absence of cells; q(r)=0 for r>R. Therefore, the differential equation for oxygen concentration in the medium (Cm) is simplified to:

$$\frac{\partial^2 C_s}{\partial r^2} + \frac{2}{r}\frac{\partial C_s}{\partial r} = \frac{K' C_s}{D_s} \quad (3.4)$$

Due to the presence of live cells inside the spheroid, oxygen is continuously lost by consumption. Thus, oxygen that enters the spheroid from the medium diffuses radially into the spheroid and is consumed at the rate of q(r) moles/L/s in the spheroidal shells. The differential equation, therefore, becomes:

$$C_m = C_\infty + \frac{A}{r} \quad (3.5)$$

$$C_s = \frac{2B}{r}\sinh(\sqrt{K}\,r) \quad (3.6)$$

$$K = K'/D_s$$

From our discrete analysis in Example 1 we found a linear relationship between the rate of oxygen consumption and oxygen concentration in the range of 0-1.5% oxygen concentration, q(r)=K→Cs, where K' is the rate constant of consumption (s$^{-1}$). Note that $C_s$ is a function of r. Therefore, the steady state radial concentration profile inside a hypoxic spheroid is determined by:

$$\frac{\partial^2 C_s}{\partial r^2} + \frac{2}{r}\frac{\partial C_s}{\partial r} = \frac{K' C_s}{D_s} \quad (3.4)$$

The solution to the above equations can be obtained using the boundary conditions of zero net flux crossing the central axis (r=0) of the spheroid owing to the radial symmetry and continuous concentration ($C_m=C_s$) and flux ($D_m dC_m/dr = D_s dC_s/dr$) at the boundary of the spheroid (r=R).

$$C_m = C_\infty + \frac{A}{r} \quad (3.5)$$

$$C_s = \frac{2B}{r}\sinh(\sqrt{K}\,r) \quad (3.6)$$

$$K = K'/D_s$$

Here $C_\infty$ is the bulk oxygen concentration at infinite distance from the spheroid which is equivalent to 20% pO$_2$ at 1 atmospheric pressure and 25° C. temperature, and A and B are constants which depend on the rate constant of consumption for the spheroid.

$$A = 2B\mathrm{Sinh}(\sqrt{K}\,R) - C_\infty R$$

$$B = \frac{-D_m C_\infty R}{2\mathrm{Sinh}(\sqrt{K}\,R)(D_s - D_m) - 2D_s R\sqrt{K}\,\mathrm{Cosh}(\sqrt{K}\,R)}$$

$D_m$ and $D_s$ are the diffusion coefficients of oxygen in the medium and inside the spheroid, respectively.

Results

Estimation of the Rate Constant of Consumption

Figure 12:
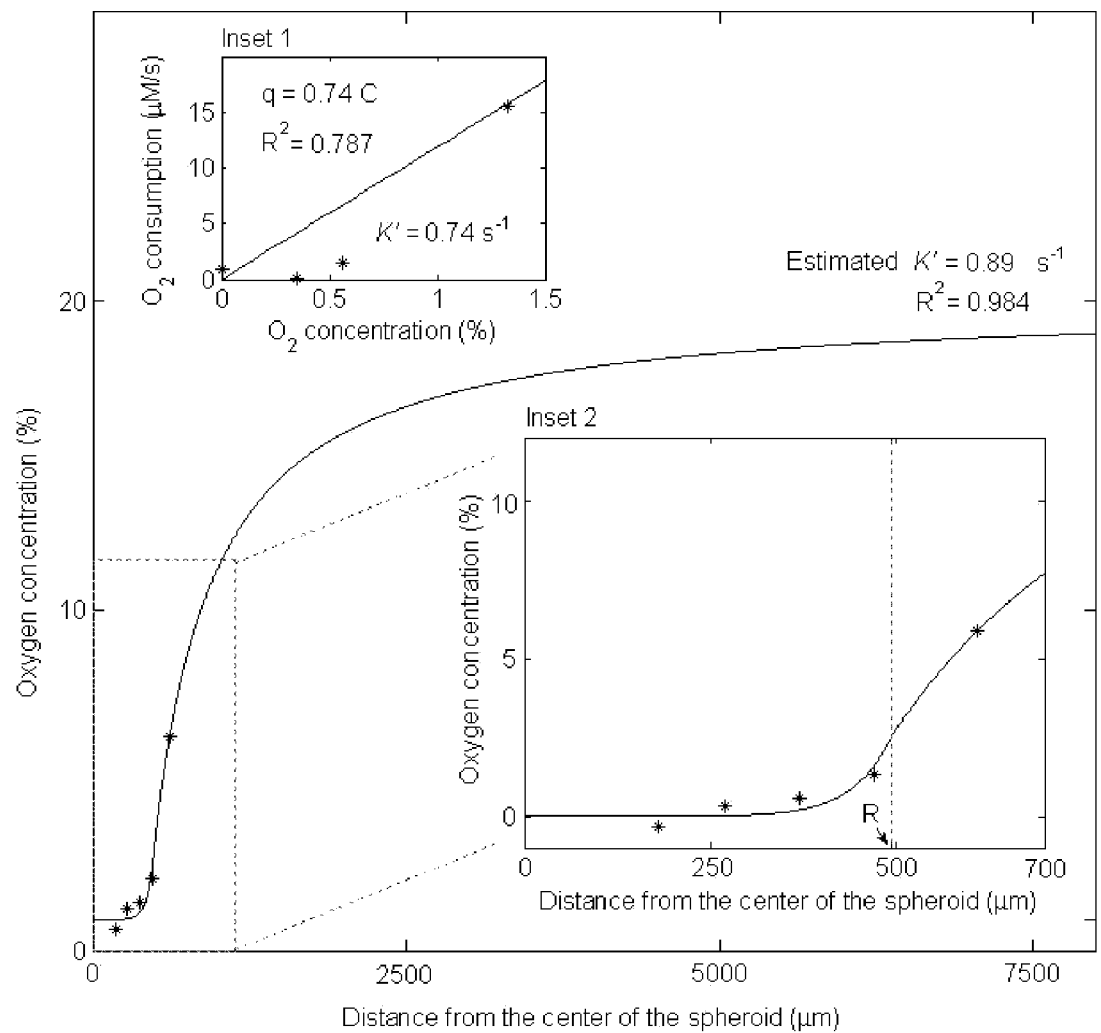
FIG. 12 is a graph showing the oxygen concentration profile for a high density agar half spheroid (3 million cells/µL). Oxygen concentration measured using the Au microelectrode array platform (*) and that predicted using the developed model (—). The parameter $K'=0.95^{s-1}$ was estimated with regression coefficient of 0.984. (Inset 1: linear relationship between oxygen consumption (µM/s) vs. oxygen concentration (%)). The slope of the linear regression, $K'=0.74^{s-1}$, was used as the initial value for model for parameter estimation. (Inset 2: close up view of the data (*) and predicted curve (—))
Figure 13:
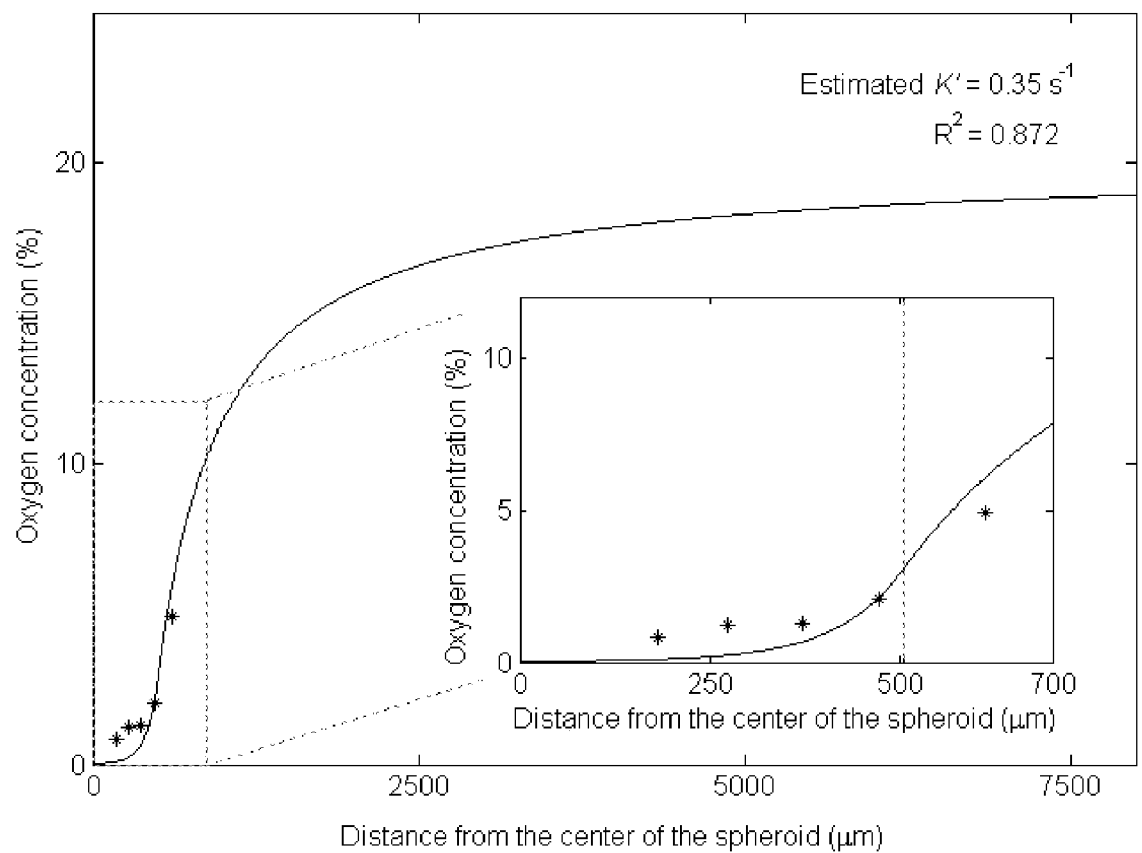
FIG. 13 is a graph showing the oxygen concentration profile for a lower density agar half spheroid (0.75 million cells/µL). Oxygen concentration measured using the Au microelectrode array platform (*) and predicted using the developed model (—). The parameter $K'=0.35^{s-1}$ was estimated with regression coefficient of 0.872. (Inset: close up view of the data (*) and predicted curve (—))

The developed model, equations (3.5) & (3.6), for oxygen concentration in and around spheroids is a one parameter model. For linear relationship between oxygen consumption and concentration, we can estimate the rate constant of consumption, K', using this model. K' is estimated to be 0.89 s$^{-1}$ for the concentration data obtained for a half spheroid of approximately 500 μm radius with 30% cell volume fraction (0.3 million cells/μL) with the regression coefficient of 0.984 (FIG. 12). The rate constant of consumption was estimated to be 0.74$^{s-1}$ from the discrete numerical difference analysis of concentration data (Example 1), which is used here as the initial value for parameter estimation (FIG. 12: inset 1). Regression coefficient of 0.982 for the predicted oxygen concentration from the model was obtained with K'=0.74 s$^{-1}$ Fitting the oxygen concentration model developed here to the measured data for a half spheroid with 7.5% cell volume fraction and radius around 500 μm, we estimated the rate constant of consumption to be 0.35$^{s-1}$. This is a little less than half of that of 30% cell volume fraction half agar spheroid (FIG. 13). The regression coefficient for this fit is 0.872.

Figure 14:
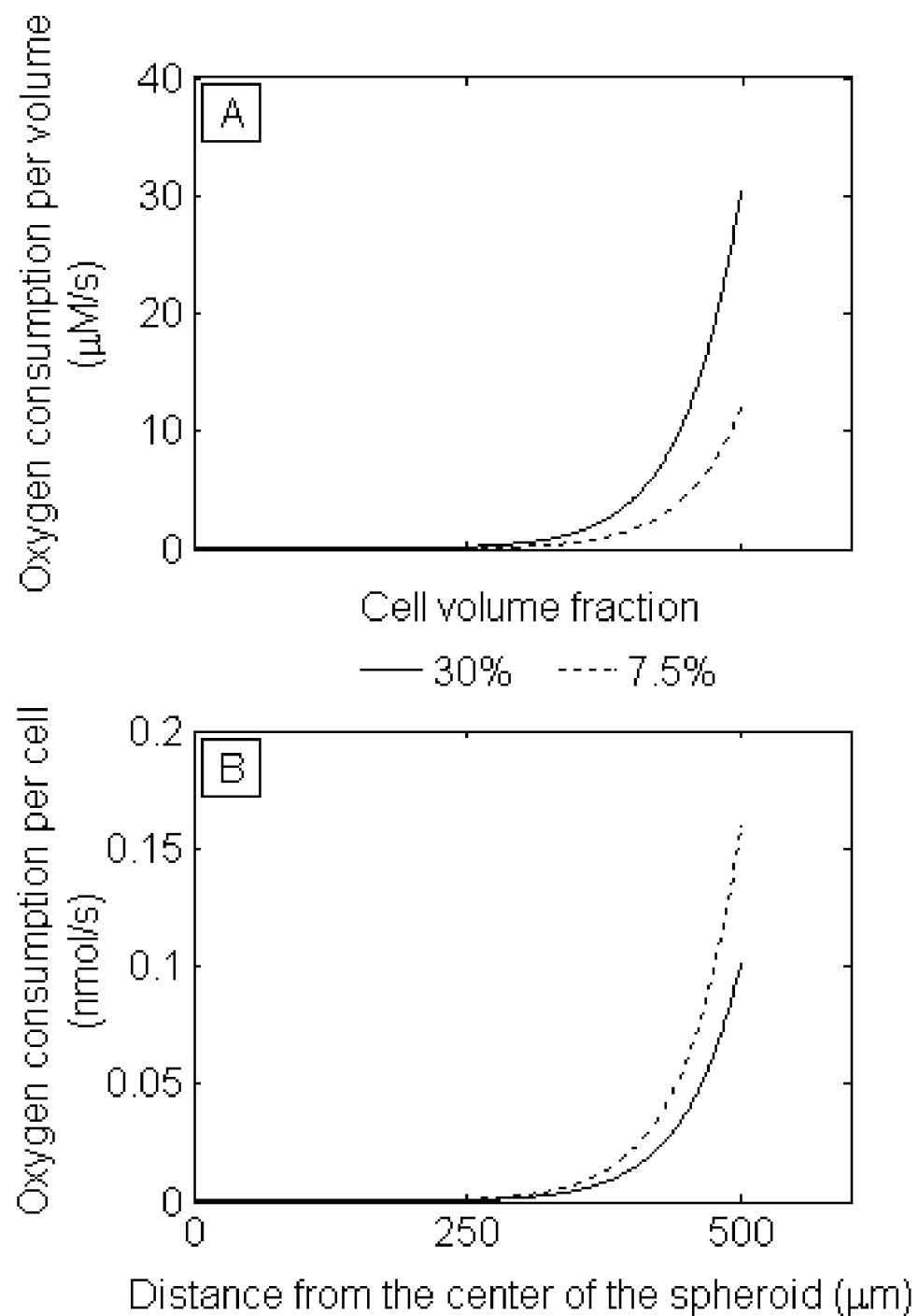
FIGS. 14A-B are a series of graphs showing the rate of oxygen consumption in high (0.3 million cells/µL, solid line) and low (0.075 million cells/µL, dashed line) density agar half spheroids.

From the fitted oxygen concentration we estimated the rate of consumption of cells along the radius of both 30% and 7.5% cell volume fraction spheroids (FIGS. 14A-B). Because of the linear relationship between consumption and concentration, per volume rate of consumption inside the spheroid also decreases radially. Per volume rate of consumption for 30% cell volume fraction spheroid is higher in magnitude than the 7.5% cell volume fraction spheroid (FIG. 14A) as expected. However, the per cell rate of consumption for 30% cell volume fraction spheroid is lower than that of 7.5% cell volume fraction half spheroid (FIG. 14B). More total number of cells inside a higher density spheroid consumes more oxygen cumulatively making the resulting oxygen concentration inside the spheroid lower than that inside the lower density spheroid. Consequently, there is more oxygen available for cells inside the lower density spheroid than in the higher density spheroid which explains the higher per cell rate of oxygen consumption. This result confirms the dependence of cellular oxygen consumption on oxygen concentration.

However, the oxygen consumption mechanism should be similar in the cells of a cultured cell line regardless of the density of cells inside the spheroid, the size of the spheroid or bulk O$_2$ concentration. Therefore, we should be able to obtain a unique rate constant parameter per cell, α, for each cell type. This is calculated by dividing the rate constant of consumption (K') for each spheroid by the density of cells in the spheroid. α is the volume rate constant with units of volume per second which denotes the consumption of O$_2$ inside the total volume fraction of a spheroid allotted to a single cell. The values of α calculated from high and low density spheroids were found to be 3.00 and 4.67 μL/s, respectively.

Figure 15:
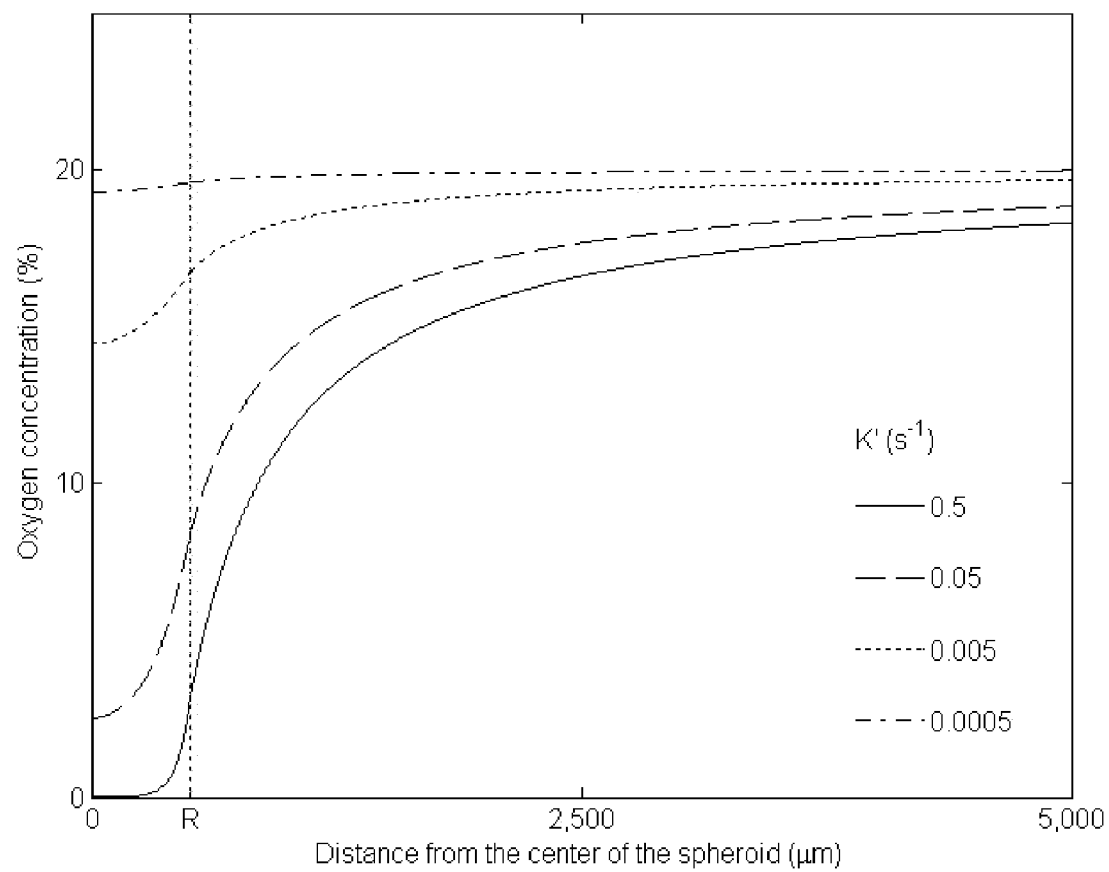
FIG. 15 is a graph showing simulated oxygen concentration profiles inside a spheroid of radius 500 µM with cell density of 3 million cells/µL with variable K' values. Concentration at the center of the spheroid is zero for maximum consumption ($K'=0.5^{s-1}$). Concentration increases as K' decreases; center concentration at r=0 approaches ambient oxygen concentration (20%) with K'=0.0005.
Figure 16:
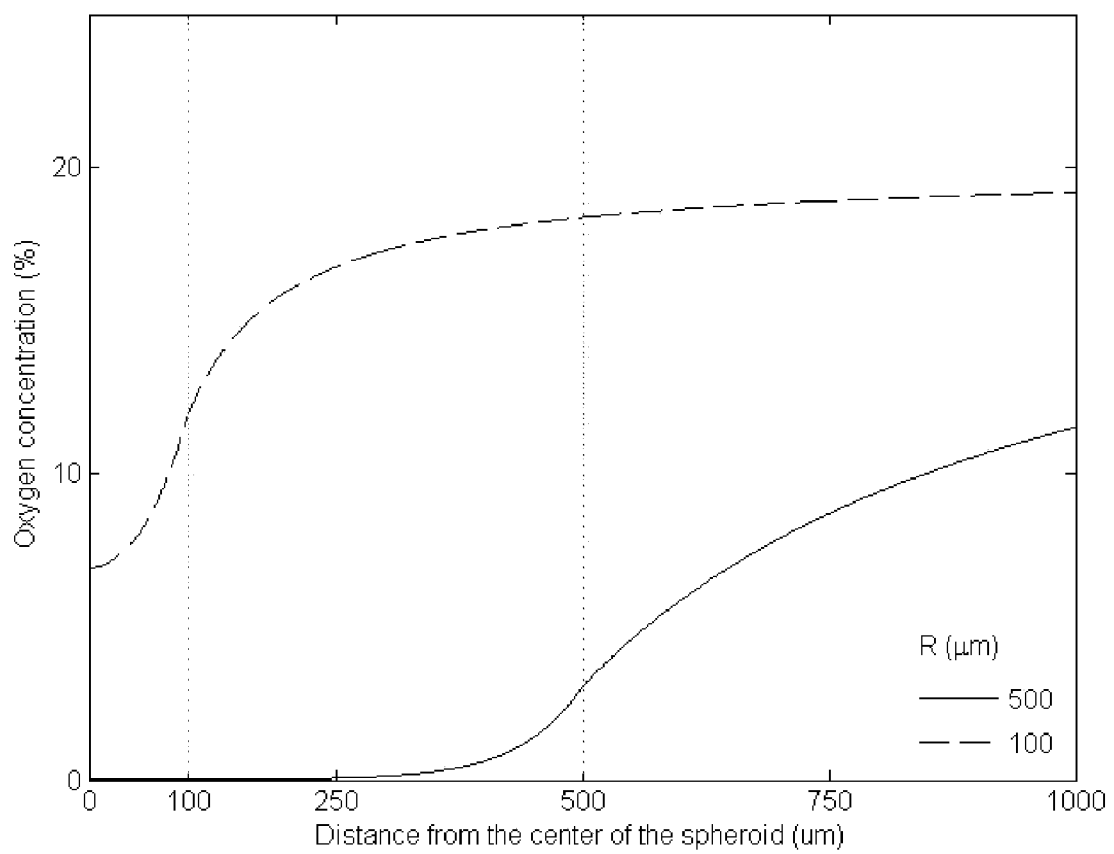
FIG. 16 is a graph showing simulated oxygen concentration profiles inside spheroids of different sizes with cell density of 3 million cells/µL with $K'=0.5^{s-1}$. Concentration at the center of the spheroid is zero for a spheroid of 500 µm radius, concentration for a smaller spheroid, R=100 µm, with same consumption will increase and the center concentration is 7%.

Simulation of Oxygen Concentration Inside the Spheroid with Variable Rate Constant of Consumption and Variable Size of Spheroid Oxygen concentration profiles inside a spheroid with given values of rate constant of consumption and size are simulated using the developed model. Oxygen concentration inside the spheroid approaches the ambient oxygen concentration (20%) as the rate constant of consumption is decreased from 0.5$^{s-1}$ to a value four orders of magnitude smaller (FIG. 15). Smaller rate constant of consumption manifests smaller rate of consumption which translates in more oxygen concentration in and around the spheroid. Oxygen concentration at the center of a smaller spheroid is found to be higher than the same for a larger spheroid with the same rate constant of consumption (FIG. 16).

Example 3

Differential Pulse Voltammetry Vs. Continuous Scanning

Experimental

Apparatus

A CHI 1030 8-channel potentiostat (CH Instruments Inc., Austin, TZ) was used to perform all electrochemical experiments. The experimental setup was placed inside a custom built Faraday cage for electromagnetic isolation. Au microdisc electrode fabricated by insulating a 50 µm Au wire with Parylene and then fixing it in non-conducting epoxy (Example 1) was used for oxygen reduction analysis on gold. A 10 µm layer of cellulose acetate was deposited on the Au electrode which was hydrated for at least an hour in PBS prior to calibration experiments. A carbon fiber electrode was used as the working electrode. An Ag/AgCl with 4M KCl filling solution (BAS Inc., West Lafayette, Ind.) and a stainless steel wire were used as reference and counter electrodes, respectively, to complete the electrochemical cell.

Measurement Parameters

Figure 17:
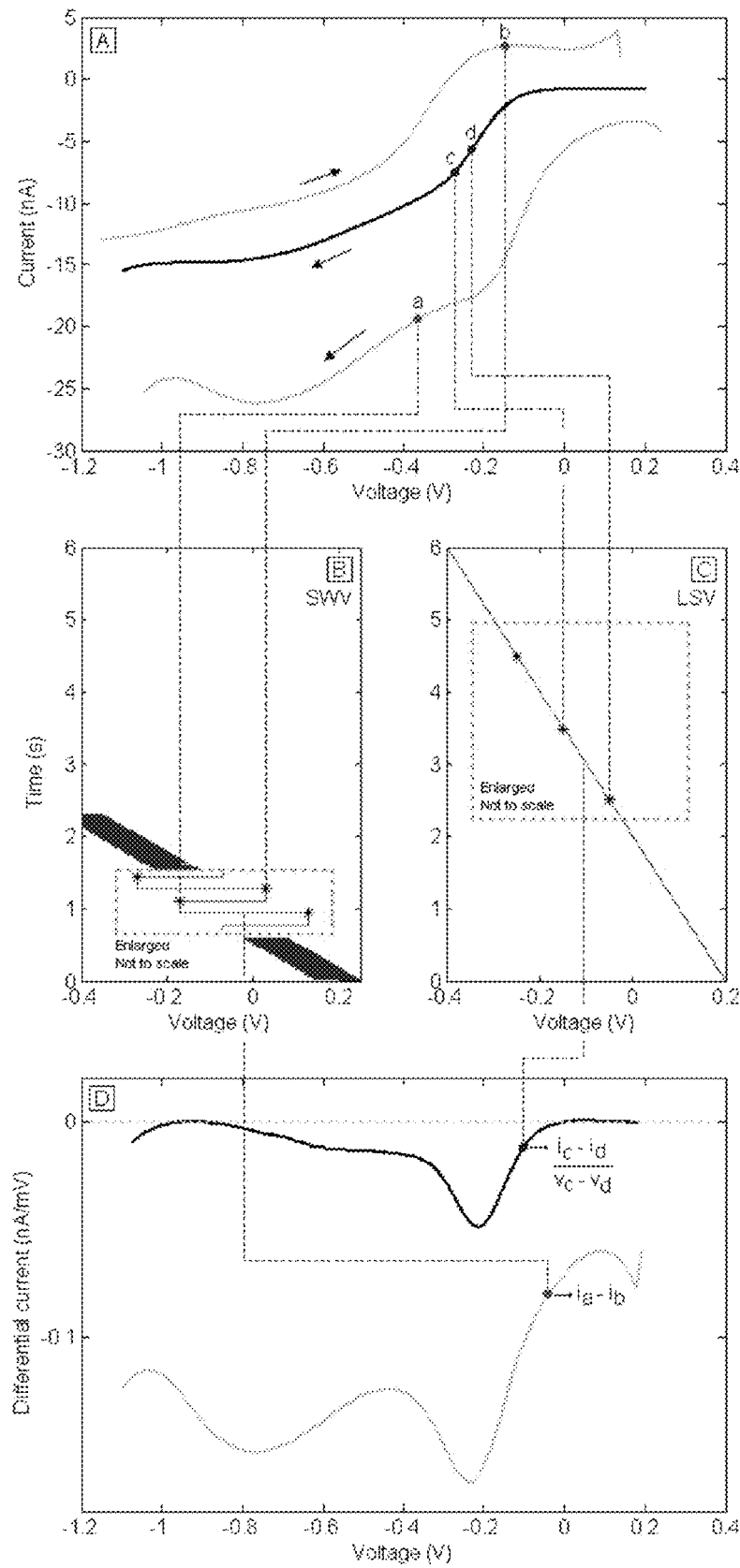
FIGS. 17A-D show differential current measurement protocols. Current—i measured in 20% $pO_2$ PBS at 1 atmosphere and 25° C.

Potential was scanned from 0.2 V to −1.1 V for Au microdisc electrode. Pulse amplitude of 50 mV and step increment of 10 mV with 30 Hz pulse frequency for oxygen measurements for SWV. The total time per scan is 4.33 s (FIG. 17B). Scan rate of 100 mV/s and sampling frequency of 100 Hz was used for LSV. The total time per scan is 13 s (FIG. 17C).

For carbon fiber electrode the potential was scanned from 0.4 V to −1.5 V. Pulse amplitude of 10 mV and step increment of 5 mV was used with 15 Hz pulse frequency for SWV. Scan rate of 100 mV/s and sampling frequency of 100 Hz was used for LSV.

Reagents

Analytical grade 1×PBS powder used for all the experiments was purchased from Fisher Scientific (Pittsburgh, Pa.). Quartz distilled water (18 MΩ·cm) was used to prepare all solutions.

Preparation of Test Solutions for Oxygen Calibration

Nitrogen gas was bubbled in air-equilibrated PBS for a minimum of 30 minutes to purge oxygen from the buffer. After 30 minutes of bubbling the oxygen concentration was considered to be nominally zero. From this point on, PBS with nominally zero oxygen concentration will be referred to as oxygen-depleted buffer. Oxygen level in the test solution was varied by adding oxygen-depleted buffer or air equilibrated PBS into the Petri dish, initially containing a known volume of air-equilibrated PBS. After each addition the test solution was homogenized by mixing the solution using a pipette for ~10 s. Corresponding oxygen concentration of the test solution was measured by a Clark-type oxygen electrode. Addition of PBS and homogenization was done in 2 minutes between subsequent SWV or LSV runs.

Data Processing

Obtaining Differential Currents

All the LSV data recorded during the experiments were processed post experiment using Matlab 7.9.0. 1st derivative Savitzky-Golay FIR quadratic smoothing filter with 25 point differentiation window was used for numerical differentiation of the LSV (DLSV) to obtain oxygen reduction peak currents from LSVs.

The current differences obtained from SWV were divided by the total pulse amplitudes (forward+reverse pulse amplitudes) to obtain SWV differential (DSWV) current.

Exposure to Cells—Biofouling Test

MCF7-R half spheroids (Example 1) were placed on the electrodes with cellulose acetate for 3 hours during which oxygen reduction current under the spheroid was constantly recorded using the gold electrode. Pre- and post-cell exposure calibrations were compared for both DSWV and DLSV to check for robustness of the measurement scheme.

Manual Baseline Subtraction for SWV

Inflection points at the base of the peaks were estimated by visual inspection. A quadratic baseline was fitted to these estimated peak bases on either side of the peak using Matlab polyfit function. The baseline current obtained at the potential of maximum absolute peak current was subtracted from maximum peak current to obtain the background subtracted SWV.

Statistical Analysis

Standard deviation of the peak currents for each pre-cell exposure calibration data set was calculated considering the linear regression of calibration as true value. 95% confidence interval around the linear calibration was estimated using Students t-test. Finally, we checked if the post-cell exposure calibration data resided in the estimated confidence interval to be able to tell with 95% certainty if the two calibrations were similar or not.

Results

Oxygen reduction current at the surface of Au microdisc electrode is recorded using both SWV and LSV techniques (FIGS. 17A-D). Forward and reverse current measured using SWV and the continuous scanning current measured using LSV protocols (FIGS. 17B-C) are used to obtain DSWV and DLSV, respectively (FIG. 17D). To align the SWV forward (negative) pulse current correctly to the pulse potentials the current is shifted to the left by 50 mV. Similarly, the SWV reverse (positive) pulse current is shifted to the right by 50 mV. SWV forward and reverse currents obtained at any potential (FIG. 17A: grey lines) is different in magnitude from the underlying LSV (FIG. 17A: black line) because of the greater capacitive currents added to the non-subtracted currents due to pulsing. This is the reason for the LSV current to lie between the SWV forward and reverse currents. DSWV obtained (FIG. 17D: grey line) has a non-zero and non-constant background current which is not the case for DLSV which represents the true differential current (FIG. 17D black line). The larger background in the DSWV is attributed to the large SWV pulse amplitudes causing unequal magnitudes of large capacitive background currents in forward and reverse pulses which leave a residual background even after subtraction. This is contrary to that seen in DLSV. The continuous scanning produces constant capacitive background currents for adjacent data points which are correctly subtracted during the numerical differentiation. The peak heights for DSWV are larger than that of DLSV. However, the real peak heights after manual background subtraction for DSWV are comparable to DLSV. This can be seen from the oxygen calibration sensitivities obtained using both techniques (FIGS. 18A-D).

Figure 18:
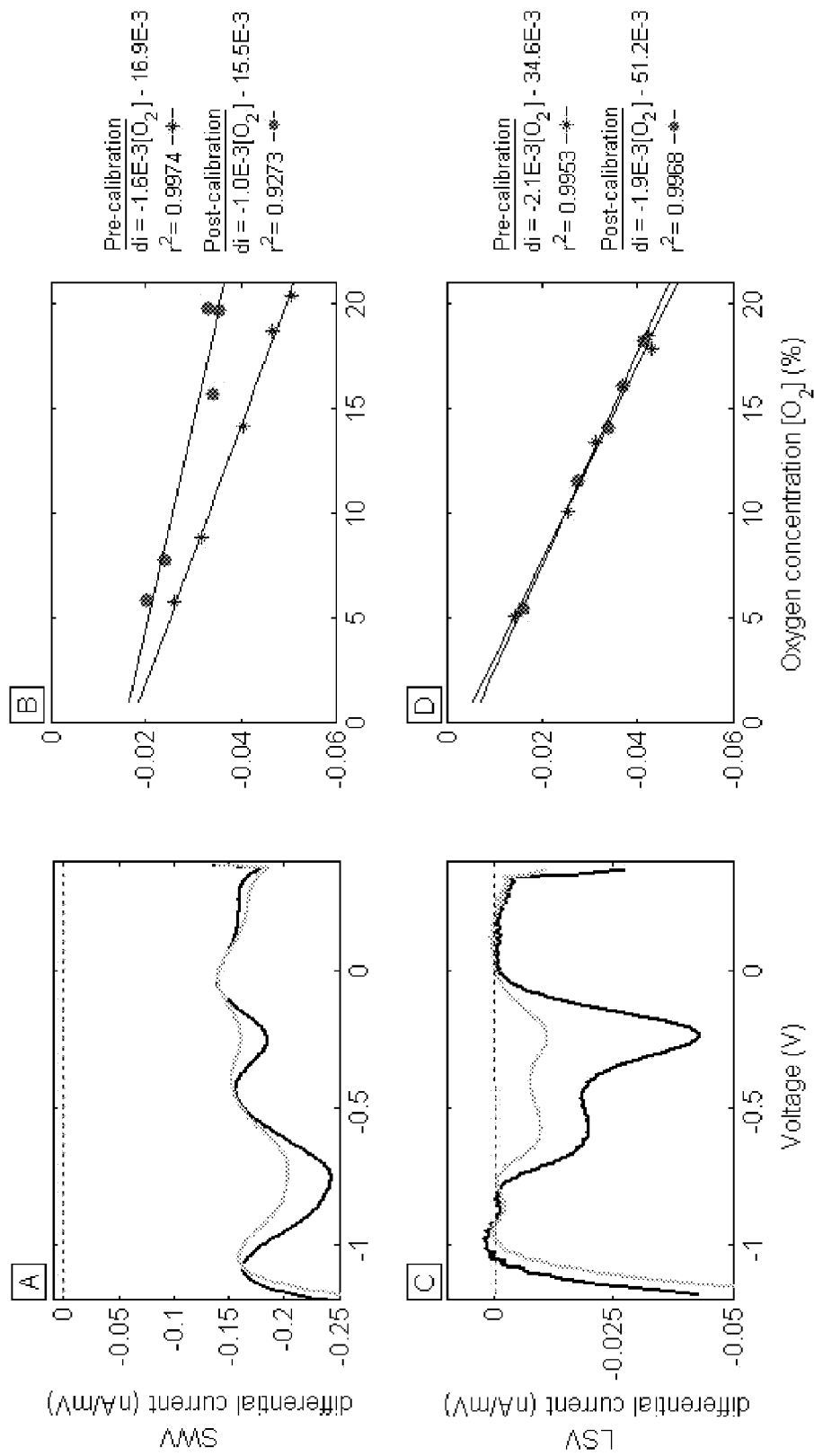
FIGS. 18A-D show a comparison between DSWV and DLSV for oxygen reduction measurement at gold electrode surface. DSWV obtained with 20% (black line) and 3% (grey line) oxygen concentrations (FIG. 18A). Calibrations of oxygen reduction differential current after manual background subtraction versus oxygen concentration obtained in PBS (FIG. 18B). (*) Pre- and (•) post-cell exposure calibrations for differential current versus oxygen concentrations. A half spheroid of MCF7-R cells was placed on the electrode for approximately 3 hours with a 10 µm cellulose acetate film as spacer on top of the electrode before obtaining the post-calibration. Linear regression coefficients of 0.9974 and 0.9273, respectively, were obtained. Note the decrease in the sensitivity of the post-calibration. DLSV obtained at 20% (black line) and 3% (grey line) oxygen concentrations (FIG. 18C). Pre- and post-cell exposure calibration of differential current versus oxygen concentrations were obtained with linear regression coefficients of 0.9953 and 0.9968, respectively (FIG. 18D). Blue dashed line (---) shows the zero current level. DLSV is more reproducible and has better sensitivity than DSWV in spite of the large absolute current.

Another confusion arising from DSWV is the estimation of the location of peak bases to extrapolate the baseline for manual background subtraction. Two 'distinct' peaks arise after the difference and thus, there is a possibility of calibrating each peak separately for oxygen concentration as seen in FIG. 18A where oxygen reduction current as a function of two different oxygen concentrations, ~20% and ~3%, is recorded. The heights of peak-1 (at −250 mV) and peak-2 (at −750 mV) decreases from ~0.185 and 0.243 nA/mV, respectively, at 20% oxygen to ~0.161 and 0.204 nA/mV absolute differential current, respectively, at 3% oxygen. Peak heights for peak-1 are used for obtaining oxygen calibration (FIG. 18B) after manual background subtraction. The DLSV at the same two oxygen concentrations show only one peak (at −230 mV) with a shoulder 'peak' (FIG. 18C). The peak height decreases from ~4.3 pA/mV to ~1.1 pA/mV for 20% and 3% oxygen concentrations, respectively. It is only clear from DLSV (FIG. 18C) that both the peaks are related to oxygen (the underlying electrochemistry is not investigated here) and therefore, the extrapolation for the baseline should span from beginning of the first peak to the end of the second peak. Erroneous estimation of peak(s) baseline also introduces variable background currents in the analytical measurements and is another potential cause for error as can be seen from the oxygen calibration in FIGS. 18A-D. The change in the post-cell exposure calibration is because of the biofouling of the electrodes which affects the both the peak height and the background current of DSWV. Calibration of differential current peak heights versus oxygen concentrations obtained prior to the cell experiment using DLSV has sensitivity of ~2.1 pA/mV for 1% change in oxygen concentration (D), which is much comparable to the sensitivity of DSWV calibration of ~2 pA/mV per 1% oxygen concentration change (C). But the pre- and post-cell exposure calibrations obtained using DLSV are found to be similar with 95% confidence unlike that for SWV.

Figure 19:
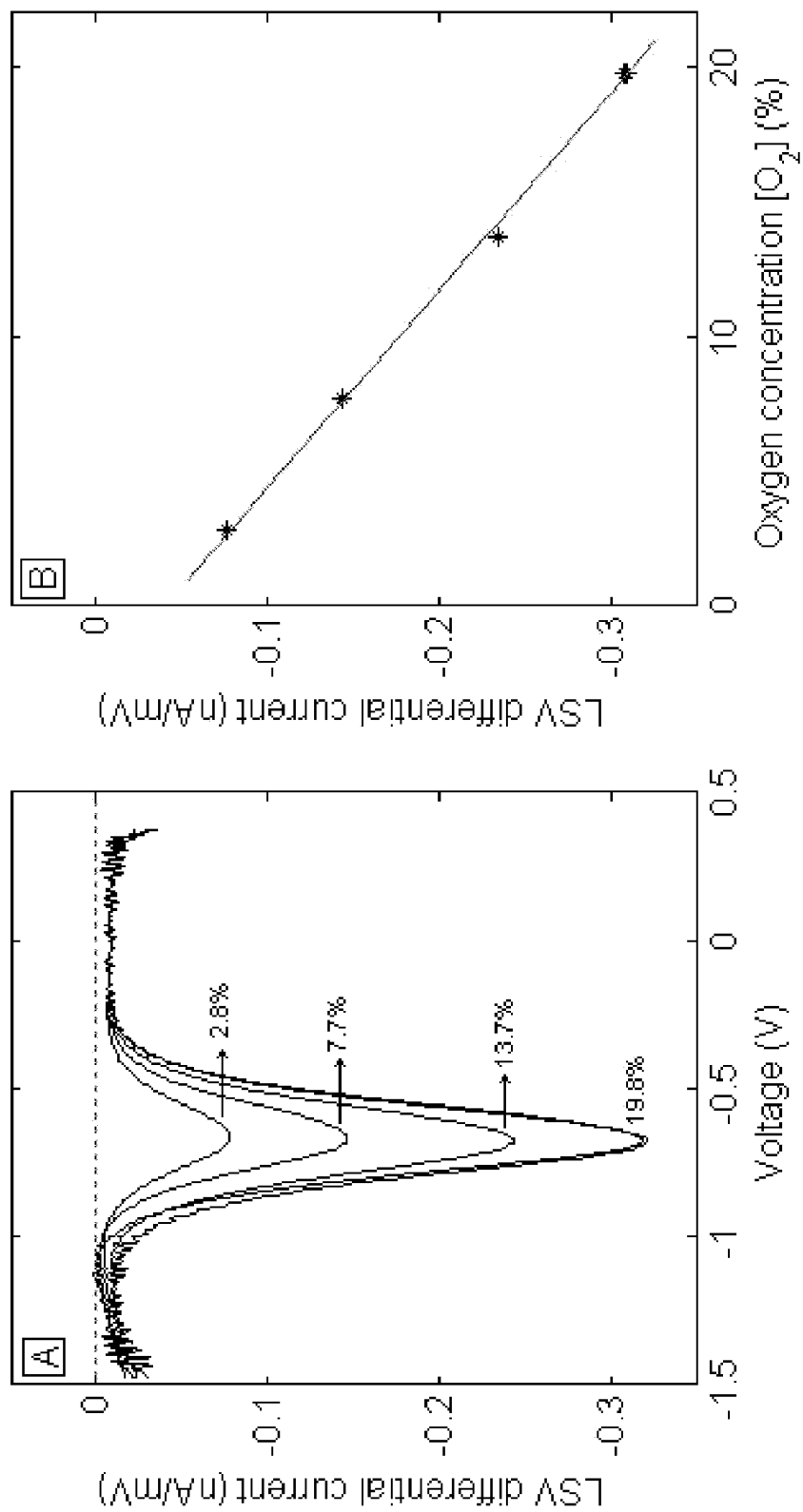
FIGS. 19A-B show calibration of oxygen reduction differential current obtained at the surface of a carbon fiber electrode versus oxygen concentration. DLSV current after numerical differentiation at different levels of oxygen concentration (%) (FIG. 19A). Note the negligible background currents obtained after numerical differentiation. Calibration of peak heights (nA/mV) versus oxygen concentrations (%) was obtained with a regression coefficient of 0.9983 (FIG. 19B)

Oxygen concentrations were obtained using a carbon fiber microelectrode with both DSWV and DLSV. Smaller voltage step increments (5 mV) and amplitudes (10 mV) were used for SWV for this experiment (methods). Negligible background was obtained for DLSVs (FIGS. 19A-B); however, the DSWV peaks were sitting on a variable, potential dependent background current. The peak heights for differential currents for both the methods were calibrated against oxygen concentrations. Linear oxygen calibration with sensitivity of 13.7 pA/mV absolute differential current per 1% change of oxygen concentration was obtained for DLSV (FIGS. 19A-B: inset). The same for SWV measurement was 20 pA/mV per 1% change in oxygen concentrations (not shown). Despite the smaller voltage step increment and amplitude, the background current is not completely eliminated from DSWV. The sensitivities of both the techniques are comparable.

Example 4

Figure 20:
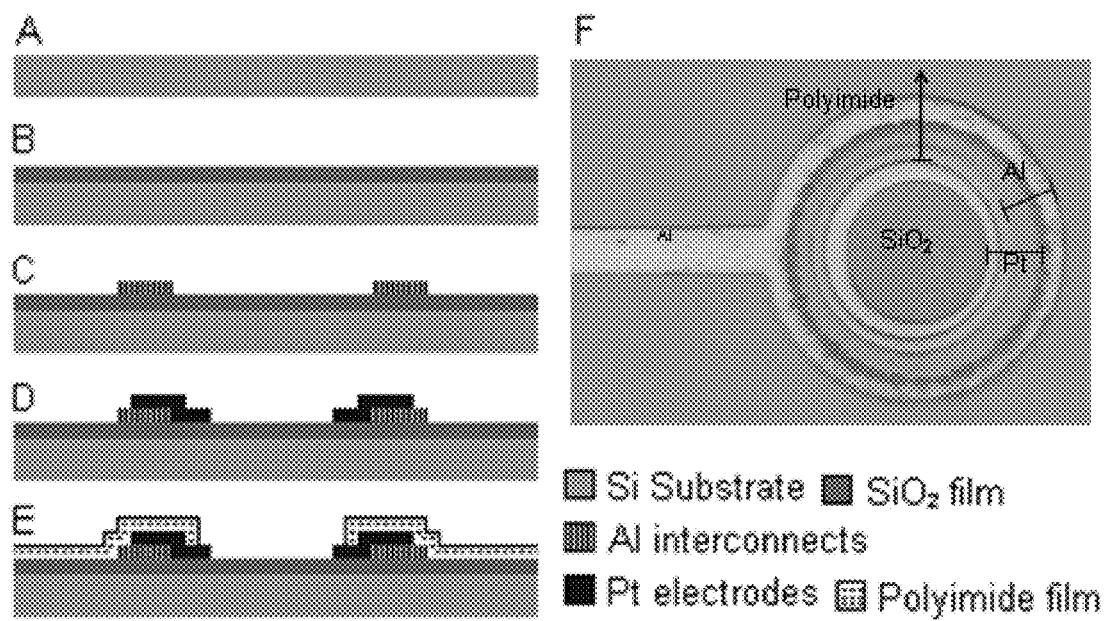
FIGS. 20A-F are a schematic illustration showing fabrication steps for Pt microring electrode and its corresponding cell site. Microfabricated sensing unit consisting of a Pt microring electrode and a cell attachment site inside the ring (FIG. 20F)

MEMS Device to Monitor Biological Oxygen Uptake at Arrays of Single Cells and Small Cell Clusters Experimental
Design Oxygen gets reduced at the surface of Pt at sufficiently negative potentials. To measure oxygen concentration at cells, we have fabricated Pt microelectrodes, each designed as a ring of 30 μm inner diameter with an exposed Pt surface of width 2 μm all around the ring for sensing. The remaining Pt surface of the microring and the $SiO_2$ surface outside the microring was covered with polyimide that is hydrophobic and thus, electrically insulating. The circular $SiO_2$ area inside the microring where cells prefer to attach because of its hydrophilicity was not covered by polyimide. From this point on, the exposed hydrophilic $SiO_2$ surface inside the microring will be called cell attachment site. Each Pt microring electrode surrounding its cell attachment site is defined as a single sensing unit (FIG. 20F). Each device had 5 sensing units to perform simultaneous experiments as well as control(s). The sensing units were positioned 500 m from each other to prevent the individual experiments from interfering with each other.

Microfabrication

The Pt microring electrodes were fabricated using the microfabrication steps shown in FIGS. 20A-F. 100 mm-diameter, single side polished, prime grade (100) Si wafer was used as substrate and all pertinent processing was performed on the polished side of the wafer using the processing tools in the Microfabrication Laboratory at CWRU.

The wafer was RCA cleaned in order to remove ionic and organic contaminants, followed by growth of 1.5 μm-thick, $SiO_2$ film by thermal oxidation on the surface of the Si wafer. The oxidizing environment consisted of the proper mix of $O_2$ and $H_2$, and was performed at atmospheric pressure at a temperature of 1100° C. After oxidation, a 5000 Å thick aluminum film was sputter deposited on the $SiO_2$ surface. This film was patterned into metal interconnects using conventional photoresist-based photolithography followed by Al etching in a commercially available aqueous Al etchant. After etching, the photoresist was removed using a metal-safe photoresist stripper—Nano-Strip™ (Cyantek Corporation, Fremont, Calif.).

Pt microrings were patterned using a lift-off process; first, Shipley 1813 photoresist was spin coated on the wafer to a thickness of 1.3 μm, and subsequently patterned into molds for the Pt microrings. After photolithography, a thin (100 Å) Ti layer was sputter deposited for adhesion promotion prior to depositing a 2000 Å thick Pt film also by sputter deposition. The Ti and Pt depositions were performed sequentially in the same chamber and under the same vacuum conditions in order to prohibit the formation of an interface oxide between the Ti and Pt layers. The Pt-coated photoresist was soaked in acetone to lift-off the unwanted Pt, leaving behind Pt microring electrodes. The Pt microrings were patterned to have sufficient overlap with the Al interconnects to make good electrical connection.

Finally, a layer of polyimide was deposited on the wafer at places other than the designated cell attachment sites. The wafer was first coated with VM 652 adhesion promoter (HD Microsystems, Parlin, N.J.) and baked for 15 min at 90° C. Then a thin layer of HD Microsystem PI 2616 polyimide was spin coated to obtain a film thickness of 1.7 μm before curing and 1.5 μm after curing. Curing was performed in an atmospheric furnace at 400° C. in nitrogen for 120 min, with temperature ramps from 150 to 400° C. at 3° C./min prior to curing and from 400 to 500° C. at 3° C./min after curing. After curing, the polyimide films were patterned using $O_2$ plasma etching. Si wafer was spin coated with a 10 μm-thick film of AZ 9260 photoresist, after which the photoresist was patterned using photolithography. The polyimide film was then etched in an $O_2$ plasma using a Tegal 803 $SiO_2$ plasma etch tool specially configured for $O_2$-based plasmas. The plasma consisted of the following gaseous mixture: 41% $O_2$, 8% $C_2F_6$ and 51% He. The forward power was 189 W and the chamber pressure was 2.8 Torr. Under these conditions, a polyimide etch rate of about 3700 Å/min was obtained. Most of the photoresist was etched during the polyimide etch process; the remaining photoresist was simply removed by rinsing in acetone. The polyimide coating was patterned such that the Al metallization was completely overcoated except at the contact pads; the Pt microring electrodes and associated regions of the $SiO_2$ underlayer-cell attachment sites in the center of the microring electrodes were also kept exposed. At this point, the wafer was inspected and diced into 1 cm×1 cm chips each with 5 Pt mciroring electrodes.

Instrumentation

A CHI 1030 8-channel potentiostat (CH Instruments Inc., Austin, TZ) was used to perform all electrochemical experiments: Cyclic Voltammetry (CV) and Pulse Amperometry (PA). The experimental setup was placed inside a custom built Faraday cage which was equipped with an XYZ stage for manipulation of the devices and a custom built thermostat to maintain the temperature inside the Faraday cage at 25° C. A Scion camera was mounted on top of the Faraday cage to visual observation of the sensing unit of interest. The microfabricated Pt microring electrode was used as the working electrode of the electrochemical cell. An Ag/AgCl reference and a Pt counter electrode were used to complete the cell.

Reagents

PBS buffer and ouabain used for cell experiments were of analytical grade from Fisher (Pittsburgh, Pa., USA) and Aldrich (St. Louis, Mo., USA), respectively. Quartz distilled water (18 MΩcm) was used to prepare all solutions.

Cell Culture

Live mouse macrophage cells (BAC1.2F5) were used for cell experiments. Culture and disposal procedures of these cells are described by E1-Moatassim and Dubyak (el-Moatassim and Dubyak 1992) in detail.

Procedures

Preparation of Test Solutions for Calibration $N_2$ was bubbled in air-equilibrated PBS for a minimum of 30 minutes to purge oxygen from the buffer. After 30 minutes of bubbling the oxygen concentration was considered to be nominally zero. From this point on, PBS with nominally zero oxygen concentration will be referred to as oxygen-depleted buffer. Oxygen level in the test solution was varied by adding oxygen-depleted buffer or air equilibrated PBS in proper volumes into a beaker, initially containing a known volume of air-equilibrated PBS. After each addition the test solution was convectively mixed with a magnetic stirring bar for ~10 seconds. This was done while current was continuously recorded by the MEMS device. Oxygen concentration of the test solution was also measured by the Clark-type oxygen electrode for control.

Addition and Positioning of Cells

A 100 μL drop of cell medium with suspended cells (105 BAC 1.2F5 mouse macrophages/mL) was gently added to the buffer with a disposable plastic pipette on top of the chip ~5 mm from the targeted sensing unit. A simple hydrodynamic manipulation technique previously developed in our laboratory (Yoshida, Tohda et al. 2003) was then used to precisely position the selected cell(s) inside the targeted microring electrode.

Addition of Solutions in Experiments Other than for Calibration

~500 μL of the required solution was added to the buffer using a disposable plastic pipette. The buffer was then homogenized by gentle circular movements induced by the same pipette for ~10 seconds.

Results

Pt microring electrodes to directly measure oxygen concentration in the vicinity of cell constructs were developed using the process described in the Experimental section. FIG. 20F shows an image of a single sensing unit that consists of a Pt microring electrode surrounding a cell attachment site. Each attachment site consists of roughened hydrophilic $SiO_2$ surface to promote attachment of cells. The microring design is to measure averaged oxygen concentration to assess overall oxygen uptake by the studied cell constructs. This shape of the microelectrode increases capture efficiency relative to a microdisc of the same active area. This will improve the signal to noise ratio of the measurement as the background current of the microring remains the same as a disc. Closeness of the electrode to the cell(s) in this arrangement increases the captured frequency content of the metabolic processes by virtue of the short diffusion pathways. Because the ring electrode is almost perfectly flush (~2000 Å thin) to the $Si/SiO_2$ substrate, physical obstruction to diffusion of the analyte molecules caused by the electrode itself is minimal. Having an array of sensing units on one chip makes it possible to obtain data from identical parallels as well as control. This will provide biostatistics with the same amount of labor and within the same amount of time as when a single experiment would be conducted.

Figure 21:
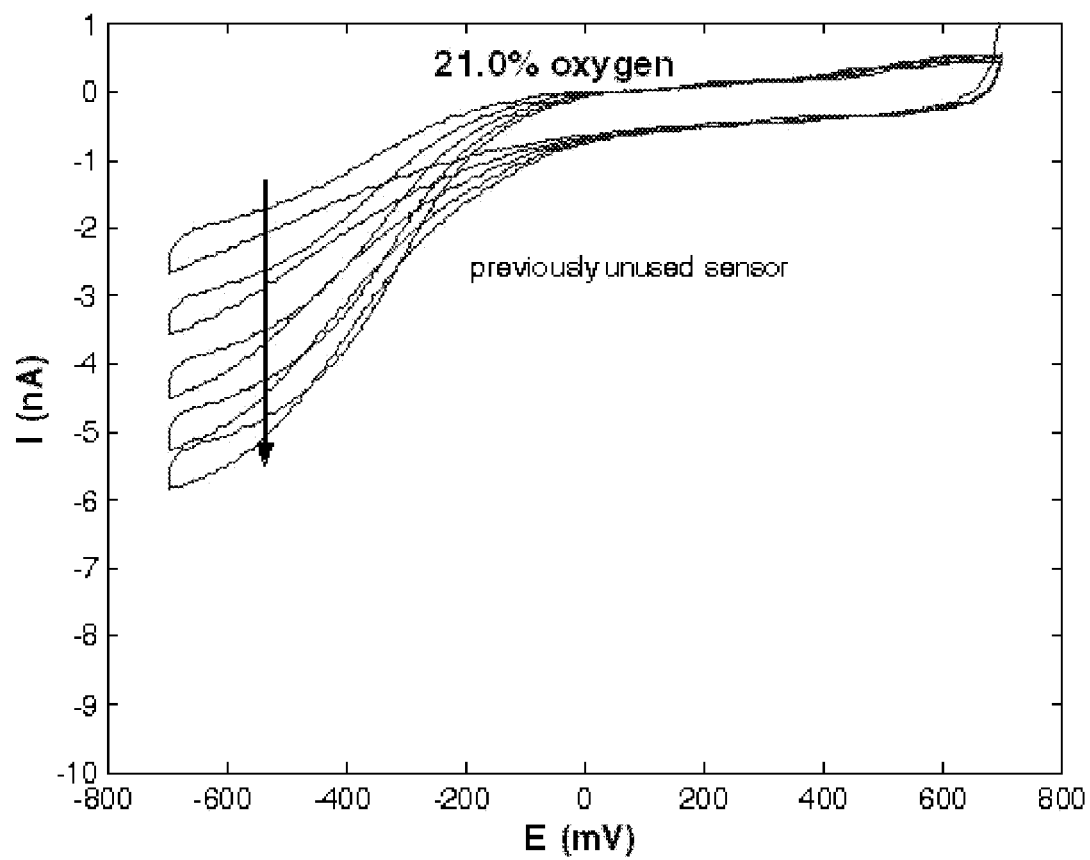
FIG. 21 is a graph showing preconditioning of a Pt microring electrode in air-equilibrated PBS. Five consecutive CVs were recorded by scanning potential between 0.7 V and −0.7 V at 0.1 V/s. The arrow points in the direction of time increase. The absolute sensor current increased during the negative scan in each subsequent CV, while the current remained constant during the positive scan.

The surface of the microfabricated Pt electrode was pretreated by repeated cycling of voltage from 0.7 to −0.7 V at 0.1 V/s for 20 cycles (see Experimental section above). FIG. 21 shows 5 consecutive cyclic voltammograms (CV) recorded during a pretreatment experiment. The absolute value of the cathodic current increased at each subsequent CV until a stable voltammetry behavior was obtained (not shown). The stabilized electrodes were characterized for oxygen reduction and based on its findings a pulse amperometry (PA) protocol was developed for monitoring oxygen uptake by cells. Finally, oxygen uptake by the BAC1.2F5 macrophage cells was monitored in normal and pharmacologically manipulated environments.

Characterization of the Pt Microring Electrodes for Oxygen Measurement

Figure 22:
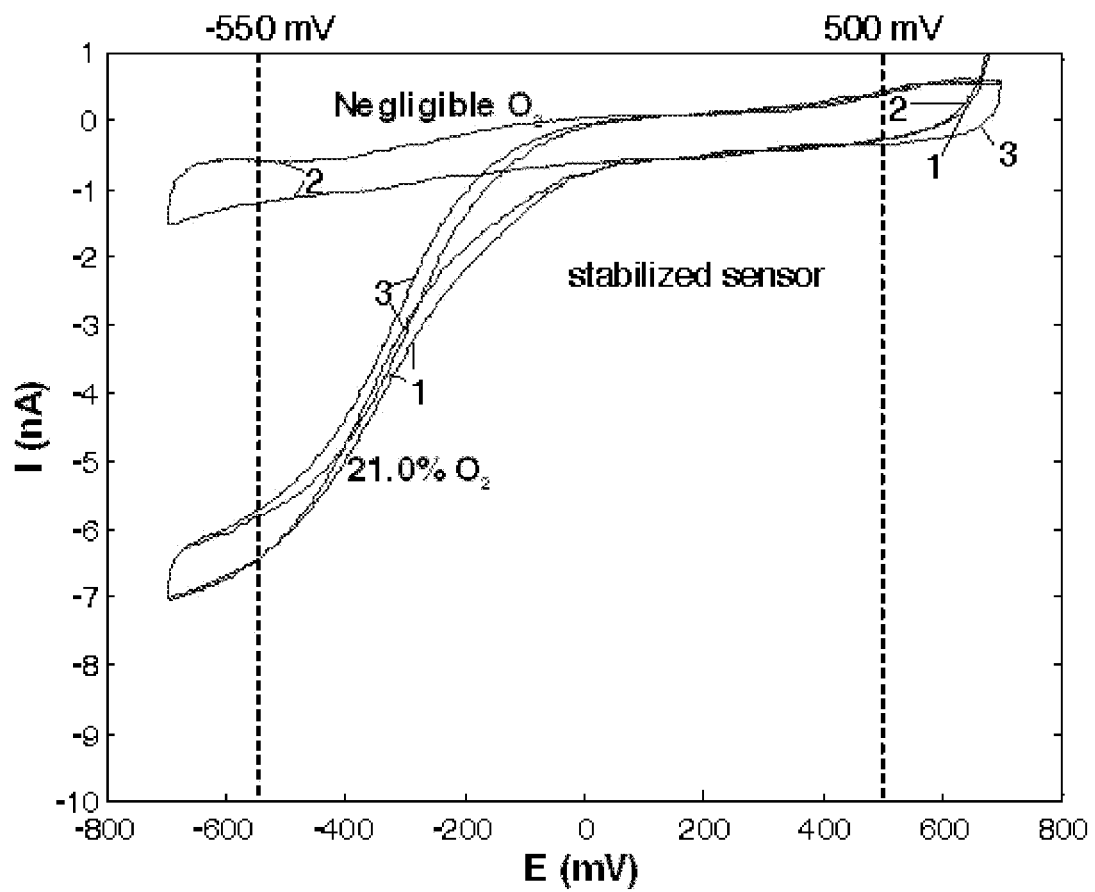
FIG. 22 is a graph showing sensitivity and reversibility of measurement of oxygen using a Pt microring electrode in PBS. Three consecutive CVs were recorded by scanning the potential between 0.7 V and −0.7 V at 0.1 V/s, run 1: air equilibrated PBS, run 2: oxygen-depleted buffer, run 3: air equilibrated PBS. Sensor current recorded at −0.55 V was approximately four times lower in run 2 when compared to run 1. In run 3, oxygen current was restored back to its previous value seen in run 1. The dotted vertical lines indicate two potentials: −0.5 V: oxygen insensitive potential, and −0.55 V oxygen sensitive potential.

To establish an electrochemical measurement protocol for monitoring oxygen with the stabilized Pt electrode we determined the sensitivity and the optimal potential range for oxygen reduction. Consecutive cyclic voltammetry experiments were performed in air-equilibrated PBS followed by cyclic voltammetry in oxygen-depleted buffer and again in air-equilibrated PBS (FIG. 22). The results indicate that reduction of oxygen at the pretreated Pt electrode is least dependent on voltage between −0.5 to −0.7 V versus Ag/AgCl. Within this range we have chosen −0.55 V for amperometric monitoring of oxygen in order to minimize potential interference by reduction of Pt at more negative potentials (results not shown). The absolute reduction current obtained in air-equilibrated PBS at −0.55 V was about four times greater than that obtained in oxygen-depleted PBS while the current obtained at +0.5 V at both the concentrations remained the same (FIG. 22). The polarity of the current recorded is not of significance in these experiments because current values at a single potential, −0.55 V, are compared. Based on this experiment, −0.55 V was used to amperometrically measure variations in oxygen concentration at the fabricated Pt microelectrodes.

Pulse Amperometry Protocol for Oxygen Monitoring

Continuous measurement will lead to sustained depletion of oxygen near the electrode. When cells are positioned near the electrodes this depletion of oxygen may perturb oxygen dependent cellular processes by decreasing the local availability of oxygen. To mitigate this undesirable effect, a pulse amperometry (PA) protocol was implemented. In this protocol the electrode potential is maintained at +0.5 V where no oxygen reduction occurs, before stepping to −0.55 V at which oxygen is reduced. The length of both pulses was chosen to be 250 ms. This restricts the time of depletion of oxygen to the cathodic pulses by allowing for replenishment of oxygen during the anodic pulses. This protocol ensures a sampling rate of 2 Hz that can assess metabolic processes occurring on the seconds time scale. Current proportional to local oxygen concentration is recorded and averaged at the end of each cathodic pulse for 50 ms. This recording period is long enough to obtain a representative value while also minimizing interference by 60 Hz noise.

Calibration of Pt Microelectrode

Figure 23:
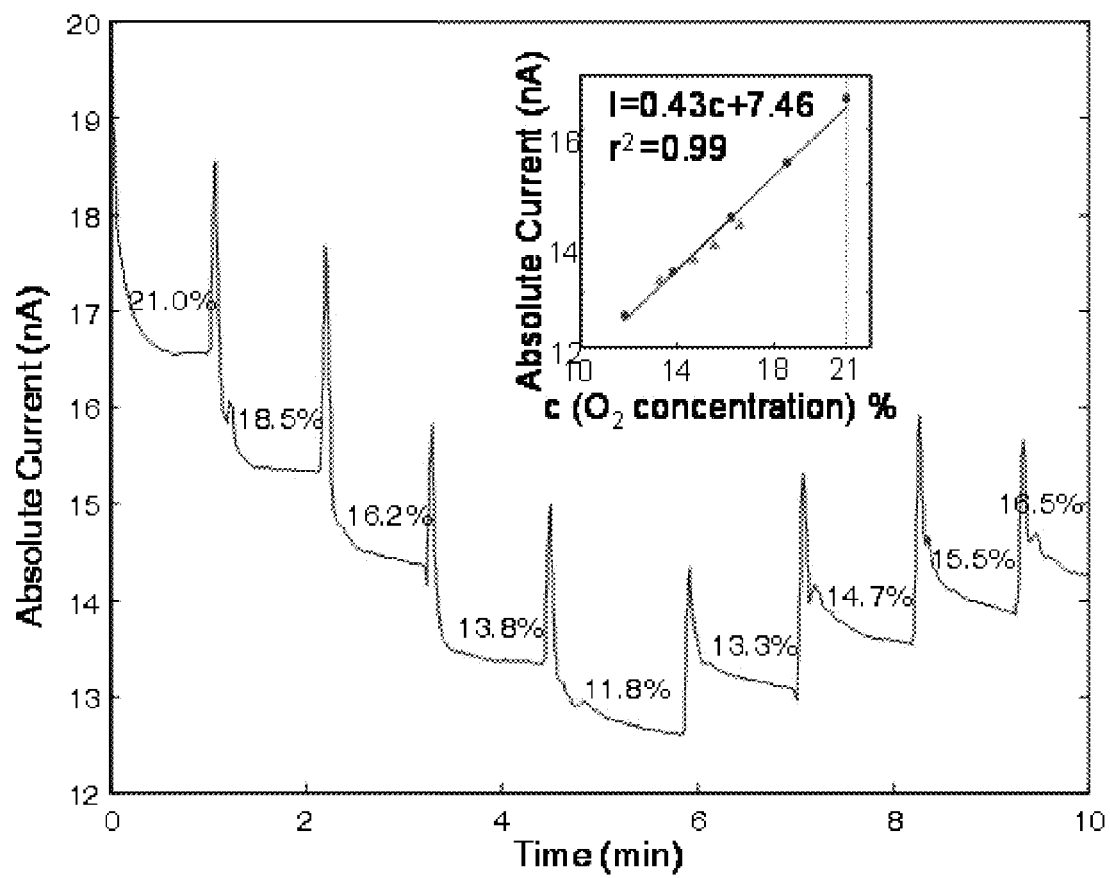
FIG. 23 is a graph showing continuous calibration of a Pt microring electrode for oxygen measurement. The oxygen concentration in the buffer was stepped down from 21% to ~12% and stepped back up to ~17% while continuously measuring oxygen current. (Inset: calibration of current (nA) versus oxygen concentration (%)). ✶ represents current when oxygen concentration was decreased and ▲ represents current when the oxygen concentration was increased.

The developed PA protocol was used to obtain continuous calibration of electrode current versus oxygen concentration in PBS. The oxygen level in the test solution was decreased stepwise from 21% to ~12% and then increased back up to ~17% (FIG. 23). This was done by adding oxygen-depleted buffer and air-equilibrated PBS, respectively, to the test solution followed by brief stirring as explained in the Experimental section. The transient peak (~20 seconds in duration) seen at the beginning of each step is due to flow caused by bulk addition of PBS and vigorous stirring of the solution. Once stirring is stopped, the current stabilizes at a level that corresponds to the new oxygen concentration of PBS. The drift seen in each of these steps is in the order of 0.3 nA or less.

To construct a calibration, a representative current value was determined in each step by averaging the data for 10 seconds before the next bolus addition. Using these values a linear regression fit was obtained with a regression coefficient, $r^2$ of 0.987 and a sensitivity in the order of 0.43 nA per 1% change in $O_2$ concentration (FIG. 23: inset). The residual error of the fit was ±0.14 nA corresponding to an uncertainty of around ±0.3% in oxygen concentration. The calibration obtained here using the PA sensing protocol is indicative of the sensitivity and reproducibility of the sensing scheme.

Monitoring Oxygen Uptake by BAC1.2F5 Macrophage Cells

Figure 24:
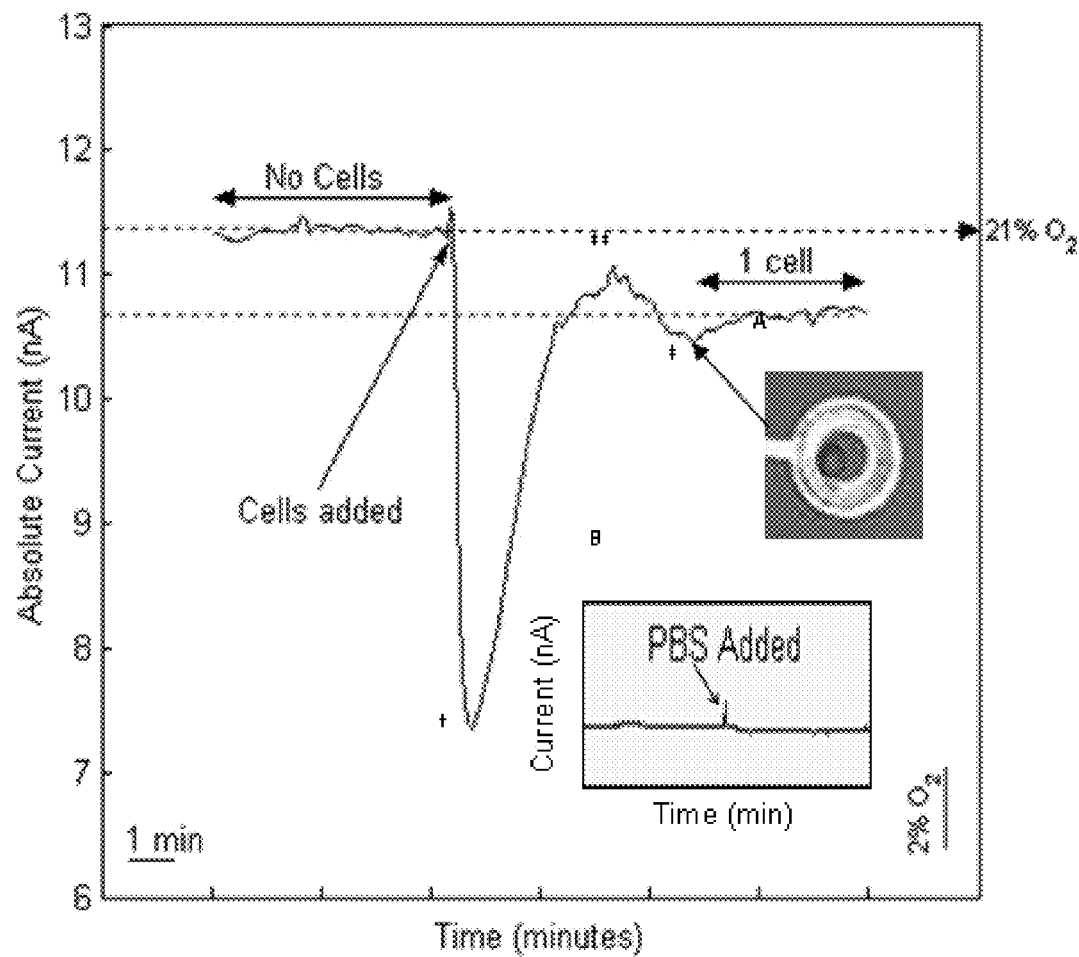
FIG. 24 is a graph showing detection of oxygen uptake by a single BAC1.2F5 macrophage cell. A lower value of stationary oxygen current was recorded after a cell was attached at the cell attachment site of a sensing unit (Inset A) when compared to the baseline current when no cell is present near the Pt microring. The small increase in current (*) is attributed to microflow created during addition of 100 µL of cell medium containing macrophage cells. The following rapid decrease in current (†) is thought to be the effect of severe hypoxia in the added cell medium. The upward current wave (**) was caused by convective flow created during hydrodynamic positioning of the cell. A subsequent small transient decrease (‡) was observed when the cell was positioned inside the ring which is likely caused by a hypoxic shell that surrounds the cell due to continuous oxygen uptake. Inset B shows a small peak caused by the addition of a 100 µL volume of air-equilibrated PBS in a control experiment. This peak is similar to the sharp peak that appears right after the addition of the bolus of cells (main panel). The respective scales for the axes in the inset are the same as those of the axes in the main panel.

A bolus of culture medium containing live macrophage cells was added near the target sensing unit and the cell(s) were then positioned inside the microring electrode as described above. As shown in FIG. 24, addition of the bolus of cells creates transient microflow at the ring electrode that is thought to cause the small upward peak in the measured current which quickly disappears (* in FIG. 24). The marked difference in the size of this peak and those seen upon addition of each buffer increment in the calibration experiment (as shown in FIG. 23) is because much less flow is generated by the gentle addition of cells unlike when deliberate stirring is used for mixing the entire solution volume as in calibration. This small peak is followed by a larger but transient decrease in current († in FIG. 24) caused by the addition of the medium containing the cells. We attribute this decrease to severe hypoxia in the cell culture medium during incubation, confirmed by independent measurements inside the culture dish with a conventional Clark-type oxygen electrode. This interpretation was further verified by control experiments performed with the developed MEMS platform. When air-equilibrated PBS was added in the same way as the bolus of cells the current did not change, apart from the small peak discussed above (* in FIG. 24, main panel and Inset B). However, addition of oxygen-depleted buffer caused a similar decrease following the small peak in the current (data not shown). This transient decrease was found to be similar to that seen when cells are added (t in FIG. 24). A combination of convection induced by the addition of the bolus (see above) and diffusive mixing leads to homogenization of local oxygen level with the rest of the buffer within one to two minutes; by the end of this hypoxic transient the baseline value is recovered in the case of addition of hypoxic buffer without cells.

When cell(s) are present inside the ring electrode, the current does not fully recover but stabilizes at a lower level. In the experiment shown in FIG. 24, a stable current of ~10.7 nA was recorded once a single cell was attached inside the microring. This current was ~0.6 nA lower than the baseline current observed before the addition of the bolus of cells. The new current value corresponded to ~19% oxygen concentration at the sensor as obtained from prior calibration specific to this sensor. As the cell is moving into the microring, a small decrease in current is observed (‡ in FIG. 24). We have seen similar decrease in current when a small floating cluster of cells passes across and above the sensor. We attribute this observation to the presence of a hypoxic region surrounding a living cell that can be termed as hypoxic shell, which moves along with the cells because of their continuous oxygen uptake. In another experiment, when 2 cells were positioned inside the microring electrode ~18% oxygen concentration was measured. Positioning of 5 cells resulted in a stationary oxygen concentration of ~15% (data not shown). An experiment in which 3 and 6 cells were subsequently positioned at the cell attachment site (FIG. 25) caused a proportional decrease in the stabilized electrode current. (The transient inverted peaks caused by the addition of the boluses seen in FIG. 24 are not shown in FIG. 25). Data from 11 experiments pooled together demonstrated that the decrease in the measured stationary oxygen concentration with respect to the number of cells positioned inside the ring sensor was linear up to six attached cells with $r^2$ value of 0.96. Moreover the result of Student's t-test indicated that the difference in oxygen concentration induced by addition of each individual cell inside the ring can be detected with better than 95% confidence. These results indicate that the developed MEMS device is capable of indicating oxygen uptake with a sensitivity sufficient to detect the addition of single cells to the already attached cell cluster.

Monitoring the Effect of Ouabain on Oxygen Uptake by BAC1.2F5 Macrophage Cells

To confirm that the observed variations in oxygen concentration indicated by the MEMS device reflect physiological processes of the cell(s), we performed another experiment where the metabolic rate of the cell(s) was pharmacologically modulated. Ouabain is known to block $Na^+/K^+$ ATPases present in the cell membrane and thus reduces metabolic activity. Thus, exposure to ouabain is expected to decrease oxygen uptake that should lead to an increase in the local oxygen concentration.

Figure 25:
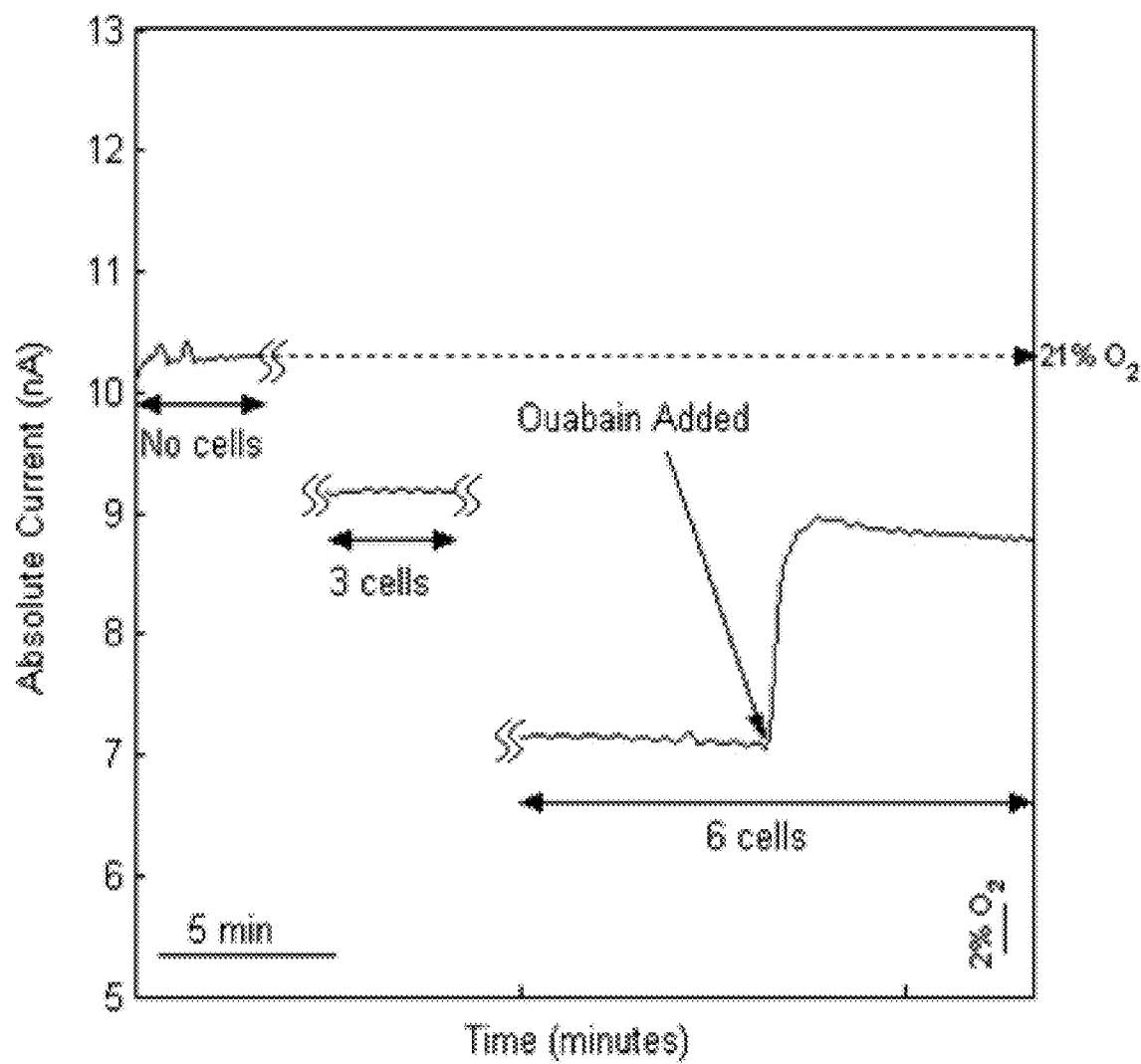
FIG. 25 is a graph showing measurement of oxygen uptake by a clusters of BAC1.2F5 macrophage cells in normal and pharmacologically modulated conditions. Proportional decrease in sensor current is recorded when 3 and 6 cells are attached inside the microring, respectively. Addition of a bolus containing ouabain near the cluster of 6 cells resulted in a rapid increase in electrode current that is sustained even after the dissipation of the added bolus.

When a cluster of 6 cells was positioned at the cell attachment site a current of ~7.1 nA corresponding to ~9% oxygen concentration was recorded (FIG. 25). A rapid increase in oxygen current was indicated at the microring electrode upon addition of ouabain. The current then stabilized at ~8.8 nA, corresponding to ~15% oxygen concentration, which was ~1.7 nA higher than that recorded before administration of ouabain. In a previous experiment when a bolus of hypoxic cell medium was added near the sensing unit the baseline current was recovered within one to two minutes (FIG. 24). This indicated that the chemical perturbation caused by a hypoxic bolus dissipates within the same time frame. This infers that the added ouabain also must have dissipated at a similar rate. However, the current increase caused by the addition of ouabain was sustained much beyond this time scale. A control experiment in which ouabain was added in the absence of cells showed no effect on current. Thus, the observed sustained increase in oxygen current is attributed to modulated metabolism that persisted even after the extracellular ouabain has dissipated. Another conclusion that can be drawn from this experiment is that the transient decrease in current that has been consistently observed after the addition of a bolus of cells must be caused by the hypoxic status of the cell culture. The data shown in FIG. 25 is representative of 3 experiments, where increase in stationary local oxygen concentration was seen immediately after the administration of ouabain.

Example 5

TABLE I.1

Sensitivities, regression coefficients and residual errors of Pre- and Post-calibration for all the electrodes

| | E1 | | E2 | | E3 | | E4 | | E5 | |
|---|---|---|---|---|---|---|---|---|---|---|
| | Pre | Post | Pre | Post | Pre | Post | Pre | Post | Pre | Post |
| Sensitivity (nA/mV/O$_2$ %) | 2.49 | 2.15 | 2.64 | 2.42 | 2.51 | 2.10 | 2.14 | 1.98 | 1.90 | 1.49 |
| Regression Coefficient | 0.993 | 0.994 | 0.993 | 0.996 | 0.994 | 0.996 | 0.995 | 0.997 | 0.991 | 0.995 |
| Residual Error (O$_2$ %) | 0.56 | 0.46 | 0.53 | 0.39 | 0.50 | 0.35 | 0.44 | 0.32 | 0.63 | 0.42 |

TABLE I.2

Oxygen concentrations measured for a representative experiment with 30% cell volume fraction half spheroid at all the electrodes

| Electrode | Distance from the center of the spheroid (μm) | Measured O$_2$ concentration (%) | | | Spheroid removed |
|---|---|---|---|---|---|
| | | QSS-1 | QSS-2 | NaN$_3$ | |
| E1 | 610 | 5.9 | 15.0 | 15.9 | 18.7 |
| E2 | 470 | 1.3 | 11.7 | 14.3 | 19.1 |
| E3 | 370 | 0.6 | 8.2 | 10.8 | 18.4 |
| E4 | 270 | 0.3 | 6.8 | 9.9 | 18.1 |
| E5 | 180 | (−0.3) | 6.2 | 9.6 | 18.2 |

Example 6

Figure 26:
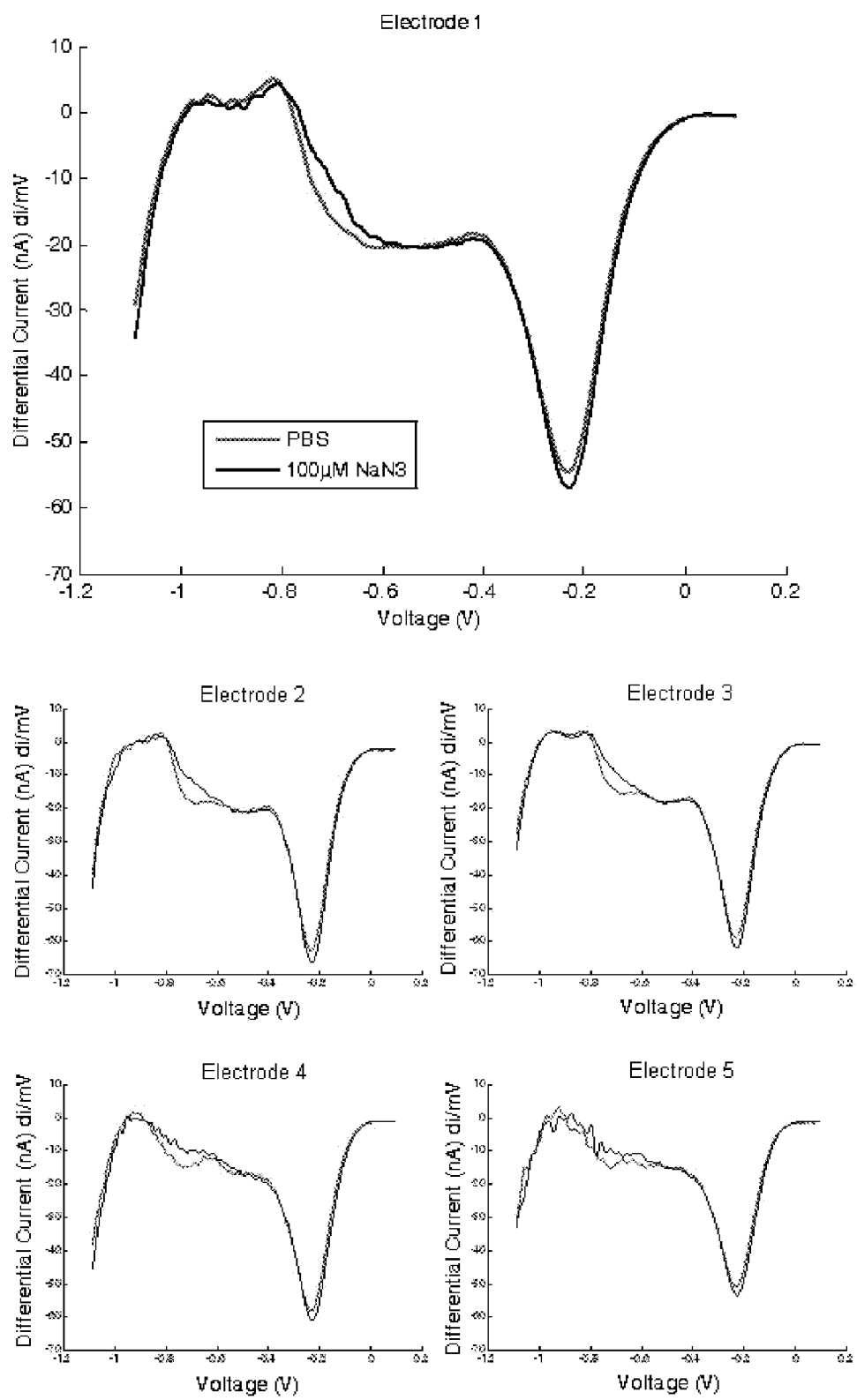
FIG. 26 is a series of graphs showing the effect of addition of $NaN_3$ on $O_2$ reduction peak. Differential current calculated before (red line) and after (black line) the addition of 100 M $NaN_3$ indicates that the effect of $NaN_3$ on the oxygen reduction peak differential current is insignificant. The $O_2$ reduction peak differential current after the addition of $NaN_3$ lies in the 95% confidence interval for all the electrodes.
Figure 27:
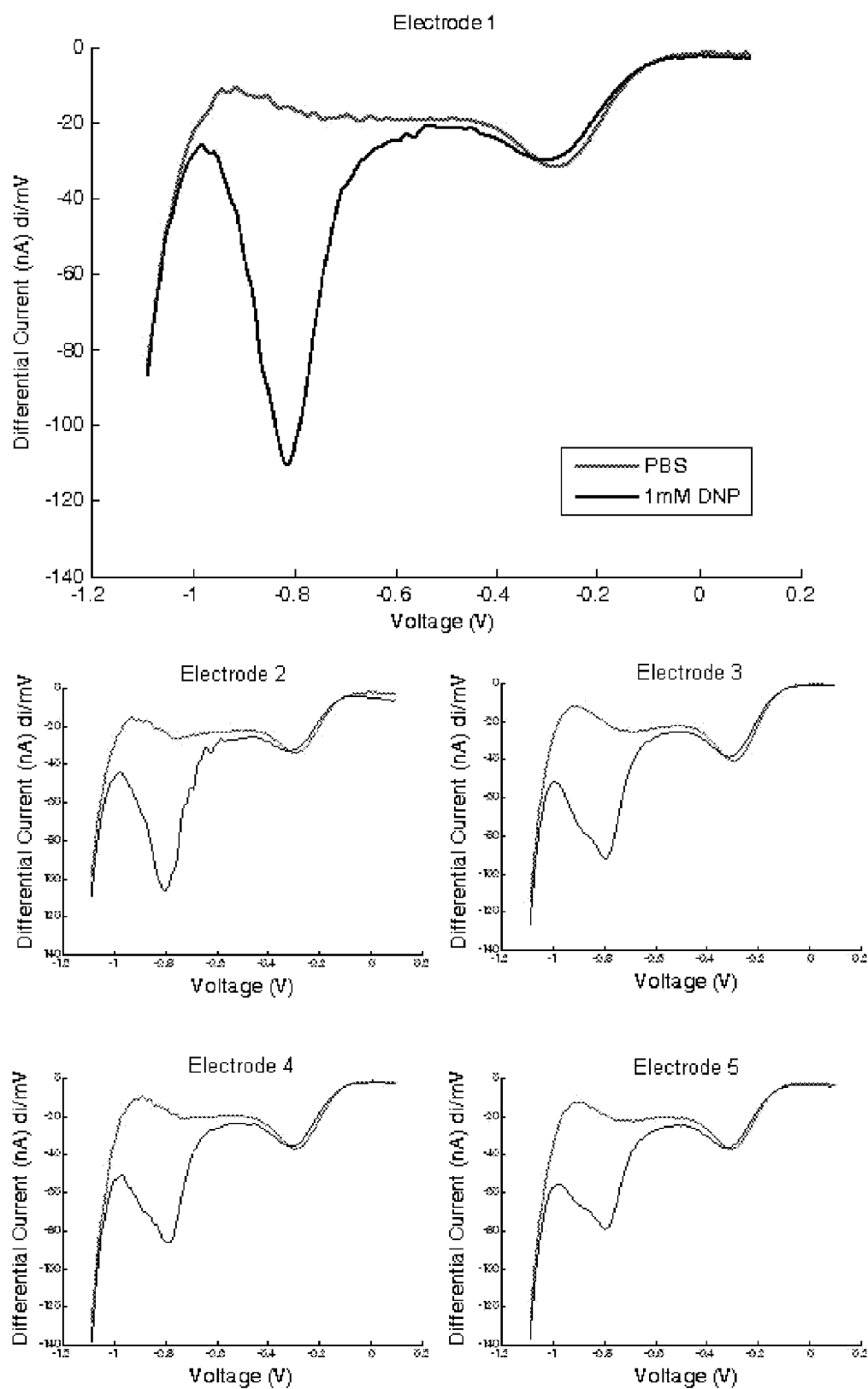
FIG. 27 is a series of graphs showing the effect of addition of DNP on $O_2$ reduction peak. Differential current calculated before (red line) and after (black line) the addition of 1 mM DNP indicates that the effect of DNP on the oxygen reduction peak differential current is insignificant. The $O_2$ reduction peak differential current after the addition of DNP lies in the 95% confidence interval for all the electrodes.
Figure 28:
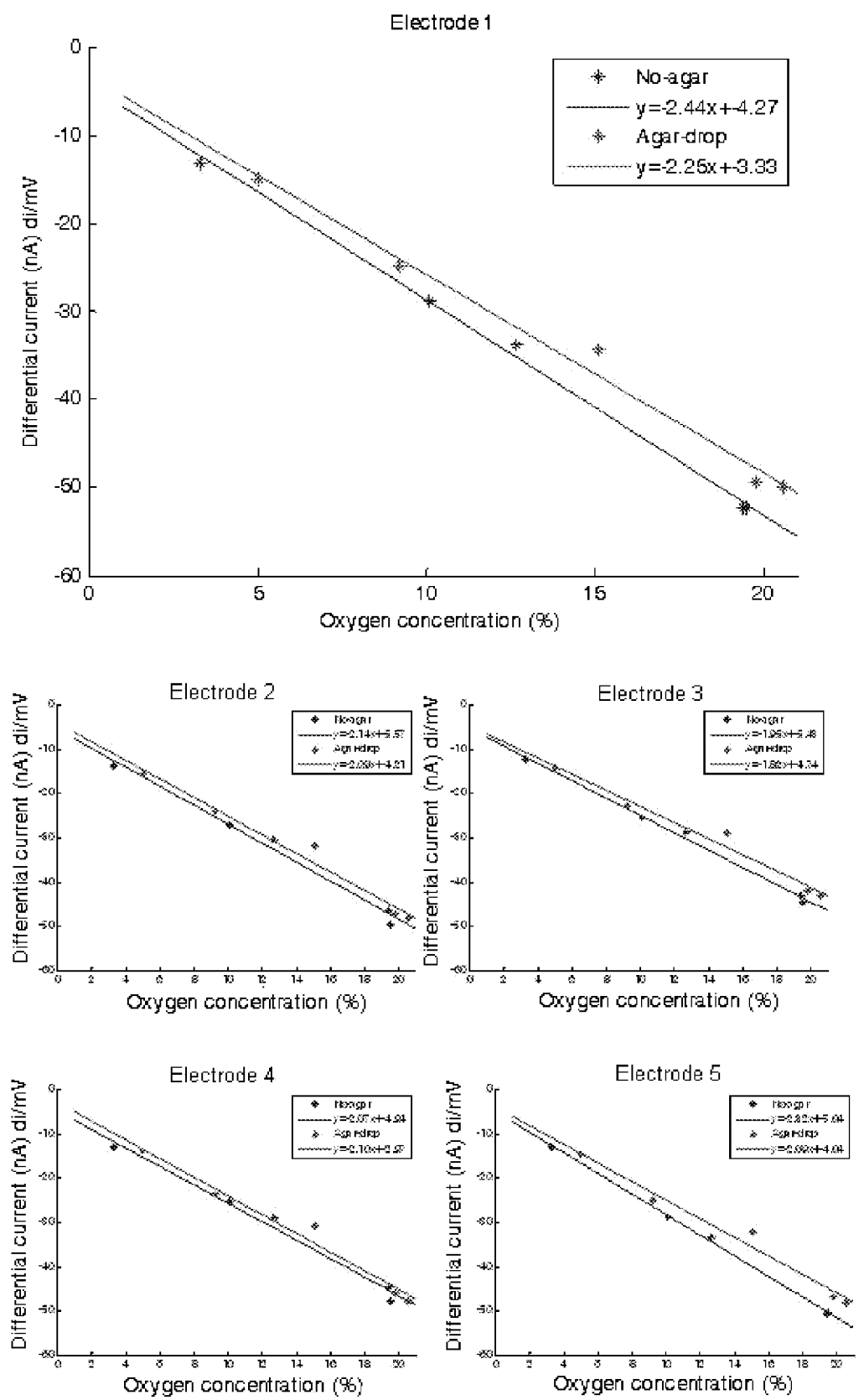
FIG. 28 is a series of graphs showing the effect of 1% agar drop sitting on top of the electrodes on $O_2$ reduction peak calibration. Calibration of oxygen reduction peak differential current obtained with (red asterisk) and without (blue asterisk) 1% agar drop (~1 mm diameter) sitting on top of the microelectrode array indicates that the change in oxygen reduction peak differential current because of agar drop is insignificant. The $O_2$ reduction peak differential currents with agar drop lie in the 95% confidence interval for all the electrodes.

Control experiments to check for interference of sodium azide (NaN$_3$) and 2,4 dinitrophenol (DNP) used for pharmacological modulation of cellular oxygen uptake with detection of oxygen at gold electrode surface (FIGS. 26-28).

Example 7

Figure 29:
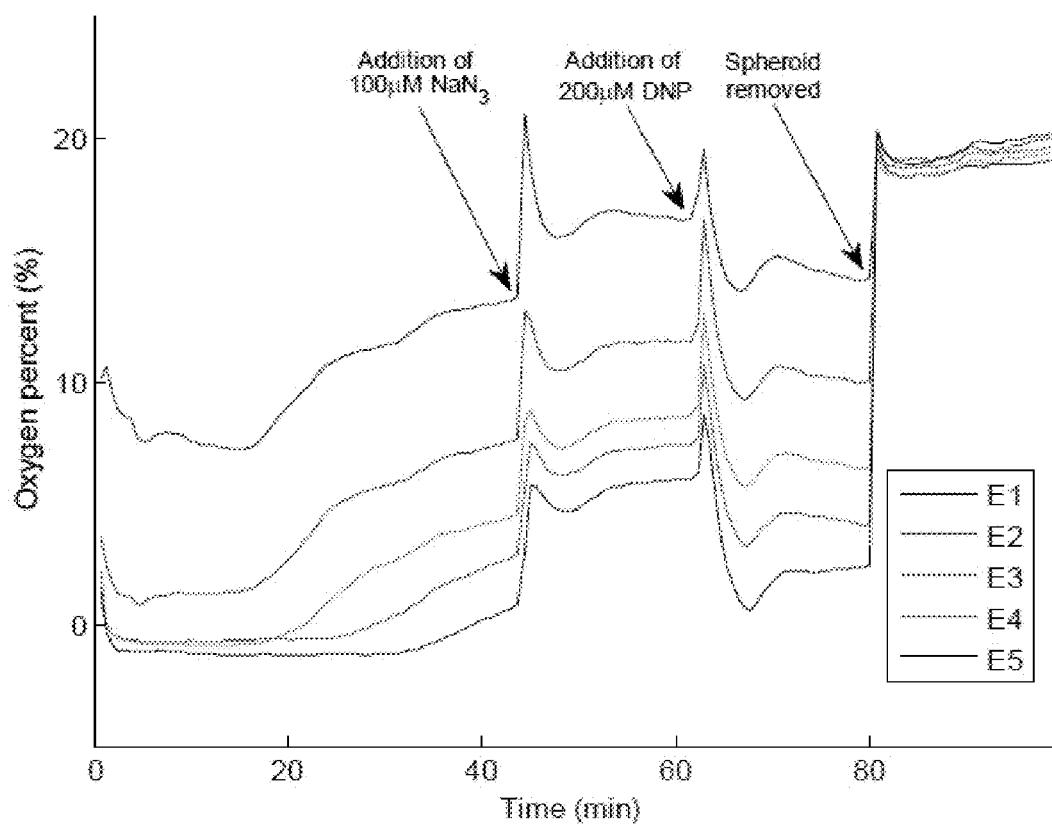
FIG. 29 is a graph showing oxygen concentration profiles measured under a 30% cell volume fraction spheroid. Oxygen concentration decreases towards the center of the spheroid (E1→E5). Negligible oxygen concentration is recorded 100 µm from the surface of the spheroid. This indicates a large zero concentration core inside the half spheroid. Measured oxygen concentration increases with 100 µm $NaN_3$ addition and decreases with 200 µm DNP addition.
Figure 30:
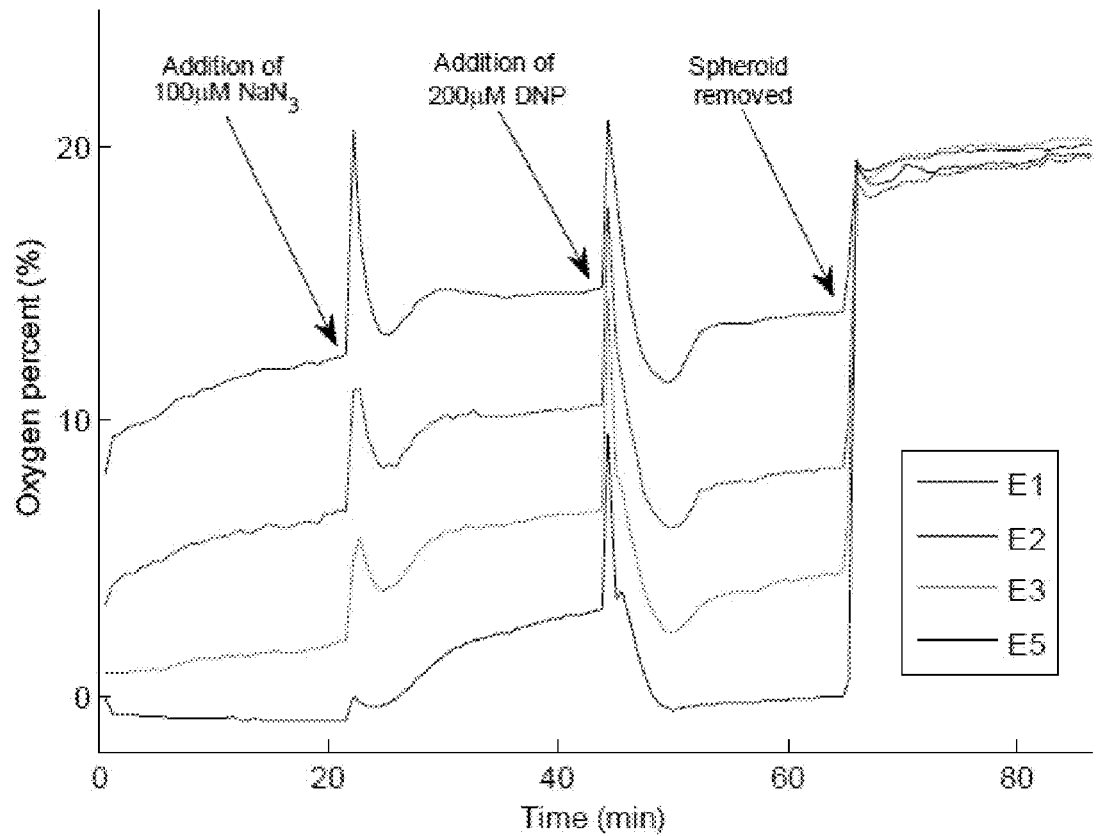
FIG. 30 is a graph showing oxygen concentration profiles measured under a 15% cell volume fraction spheroid. Oxygen concentration decreases towards the center of the spheroid (E1→E5). Negligible oxygen concentration is recorded only around ~350 μm from the surface of the spheroid. This indicates a smaller zero concentration core inside the half spheroid. Measured oxygen concentration increases with 100 μm $NaN_3$ addition and decreases with 200 μm DNP addition.
Figure 31:
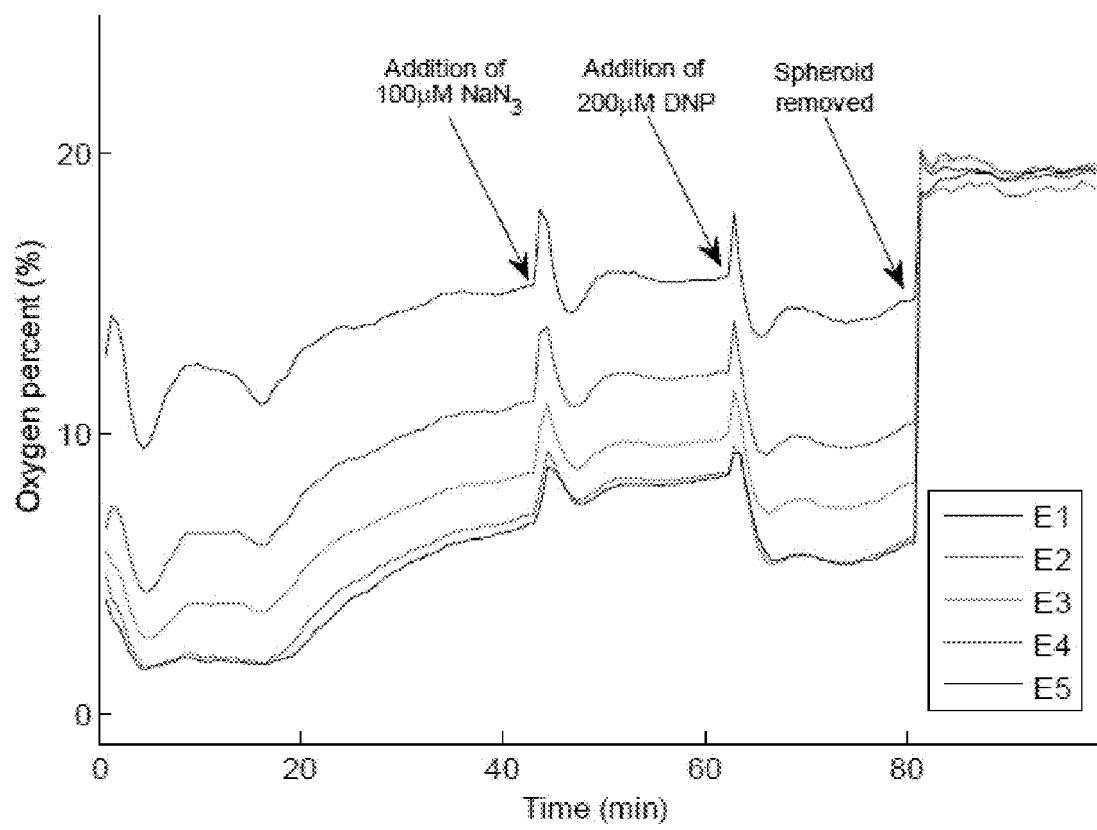
FIG. 31 is a graph showing oxygen concentration profiles measured under a 30% cell volume fraction spheroid. Oxygen concentration decreases towards the center of the spheroid (E1→E5). Non-zero oxygen concentration is recorded 400 μm from the surface of the spheroid. Moreover, a E4 and E5 measure the same oxygen concentration indicating a non-zero oxygen concentration core. Measured oxygen concentration increases with 100 μm $NaN_3$ addition and decreases with 200 μm DNP addition.

Oxygen concentration was measured under half spheroids with varying cell densities. 30%, 15% and 7.5% cell volume fraction half spheroids were made and positioned as explained above. Oxygen concentration measured under the highest density spheroid (30% cell volume fraction) were the lowest (FIG. 29) with zero oxygen concentration 100 m from the surface of the spheroid. Increasing oxygen concentrations were measured inside the spheroid with decreasing cell density (FIGS. 30-31).

Example 8

Figure 32:
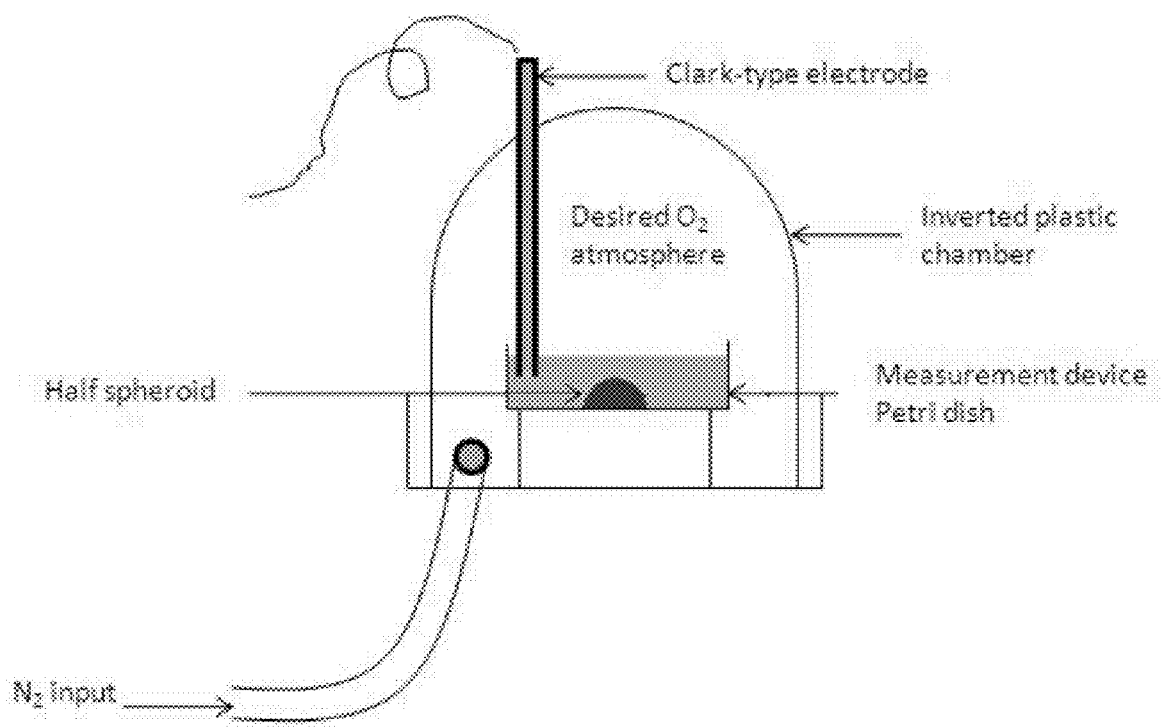
FIG. 32 is a schematic illustration showing on example of an oxygen chamber set-up to maintain desired $pO_2$ around a spheroid.
Figure 33:
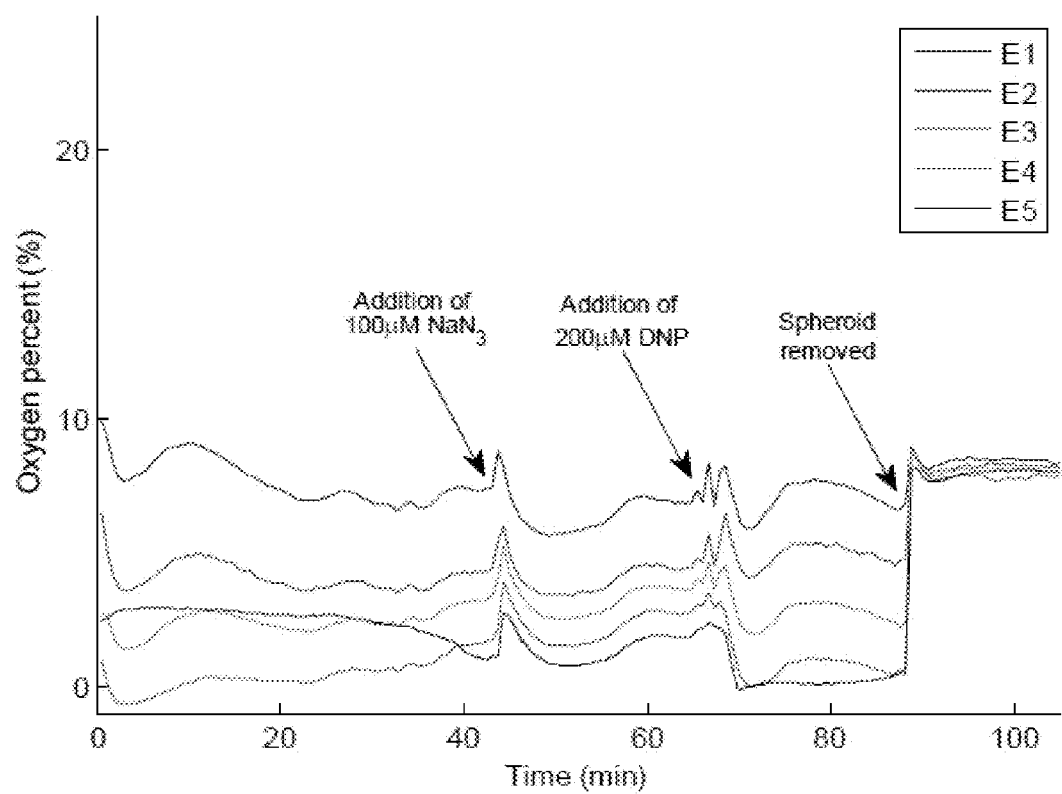
FIG. 33 is a graph showing oxygen concentration profiles measured under a 15% cell volume fraction spheroid with 10% ambient $pO_2$. Oxygen concentration decreases towards the center of the spheroid (E1→E4). Measured oxygen concentration increases with 100 μm $NaN_3$ addition and decreases with 200 μm DNP addition.
Figure 34:
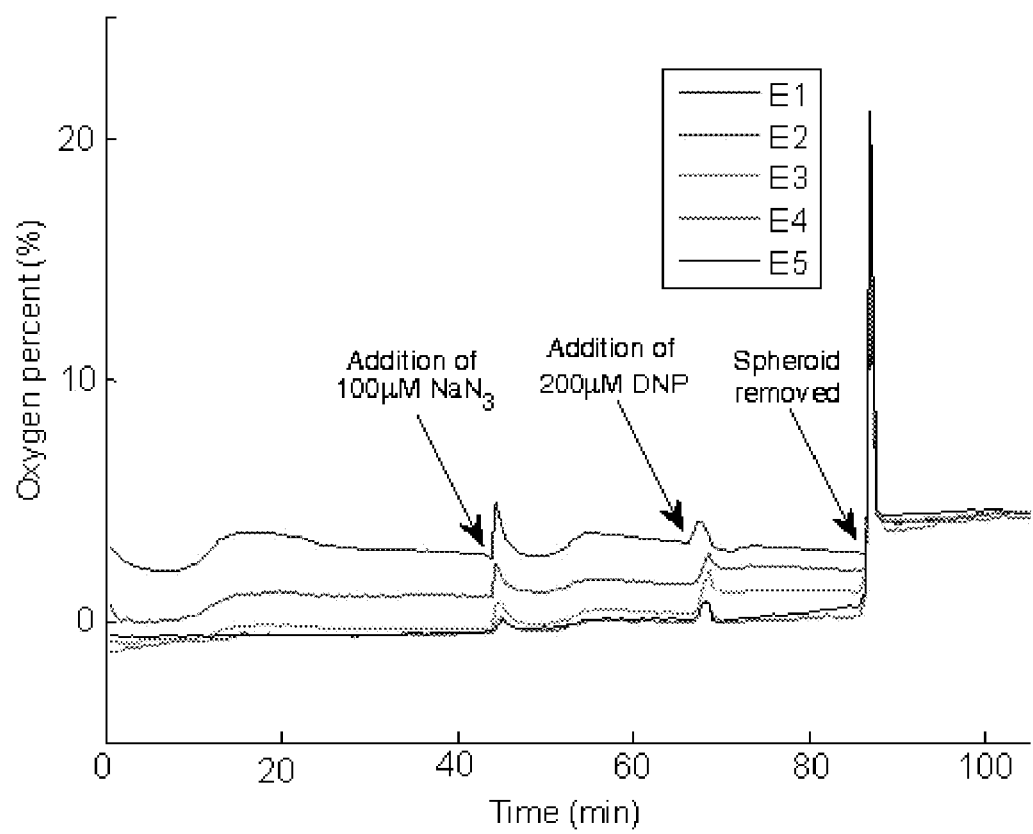
FIG. 34 is a graph showing oxygen concentration profiles measured under a 15% cell volume fraction spheroid with 5% ambient $pO_2$. Almost zero oxygen concentration was measured for the entire half spheroid starting from E2, which is positioned at the edge of the spheroid. Measured oxygen concentration increases with 100 μm $NaN_3$ addition and decreases with 200 μm DNP addition.

Oxygen concentration was measured under half spheroids with 15% cell volume fraction when bulk oxygen concentration around the spheroid was varied. Bulk oxygen concentrations were decreased to replicate in-vivo oxygen environment. A preliminary low oxygen chamber was made using an up-side down plastic glass in which 100% pure N$_2$ gas was constantly inserted via a hole (FIG. 32). Oxygen concentration in the PBS surrounding the spheroid was monitored continuously by a Clark-type oxygen electrode. The flow of N$_2$ was adjusted manually depending on the reading of the Clark-type electrode. FIGS. 33-34 show oxygen profiles under a half spheroid when the ambient oxygen concentration was maintained at 10% and 5% pO$_2$, respectively.

Example 9

Figure 36:
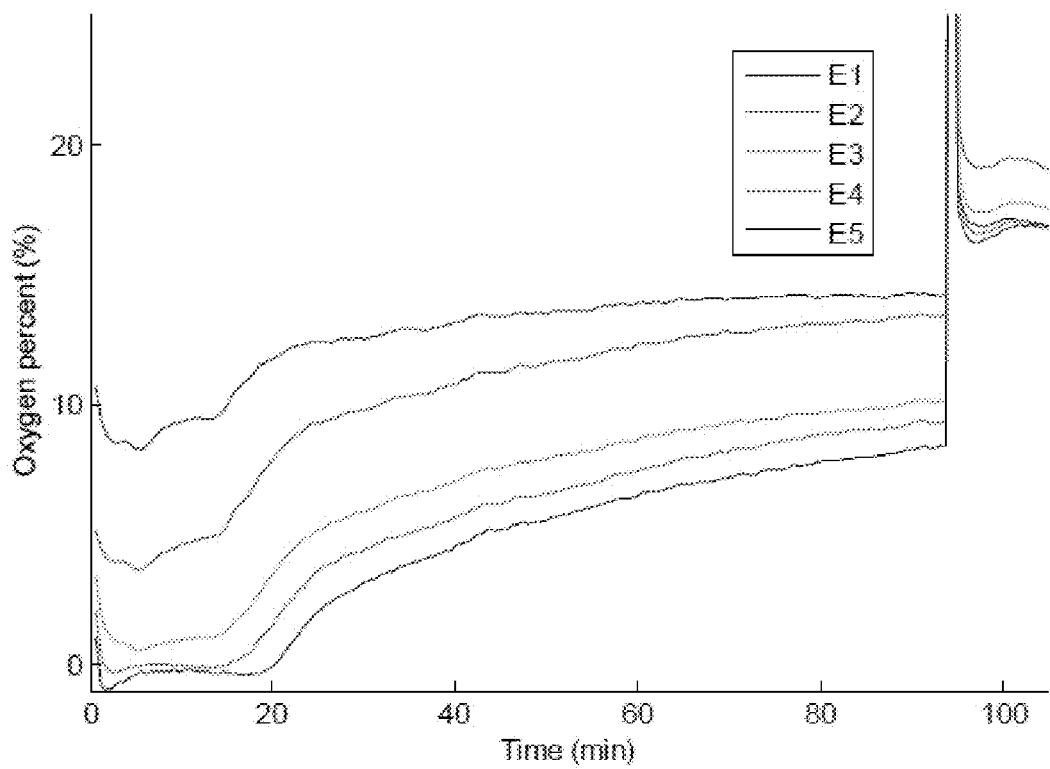
FIG. 36 is a graph showing a representative experiment of continuous monitoring of oxygen concentrations under a half spheroid. The rapid increase in oxygen concentration thought to be because of glucose deprivation is seen here.

All experiments done with half spheroids showed a rapid increase of oxygen concentrations around 20-30 minutes into the experiment which is thought to be the result of lack of glucose in the PBS surrounding the spheroid. To confirm this hypothesis 25 mM D-Glucose (same as medium concentration) was added in the PBS after the increase. Addition of glucose to the PBS resulted in decrease in the measured oxygen concentration almost instantaneously (FIG. 35). FIG. 36 shows a representative experiment where oxygen concentrations were measured under a half spheroid.

Example 10

Figure 37:
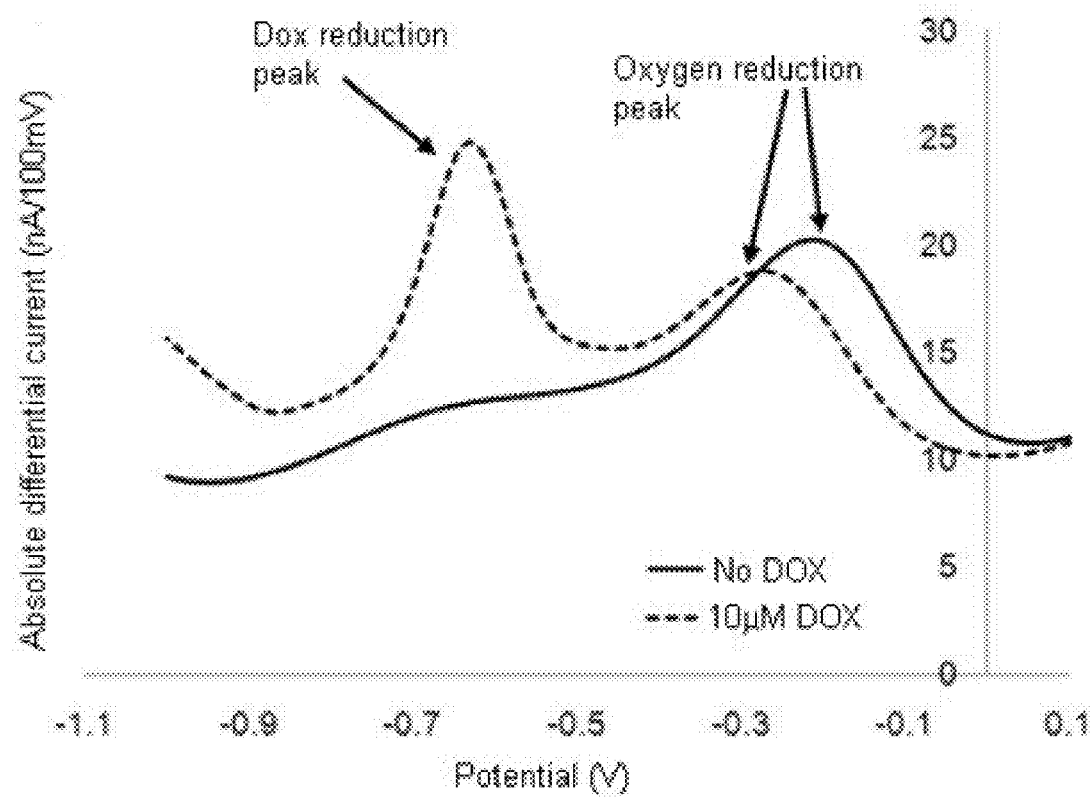
FIG. 37 is a graph showing simultaneous measurement of $O_2$ and DOX.
Figure 38:
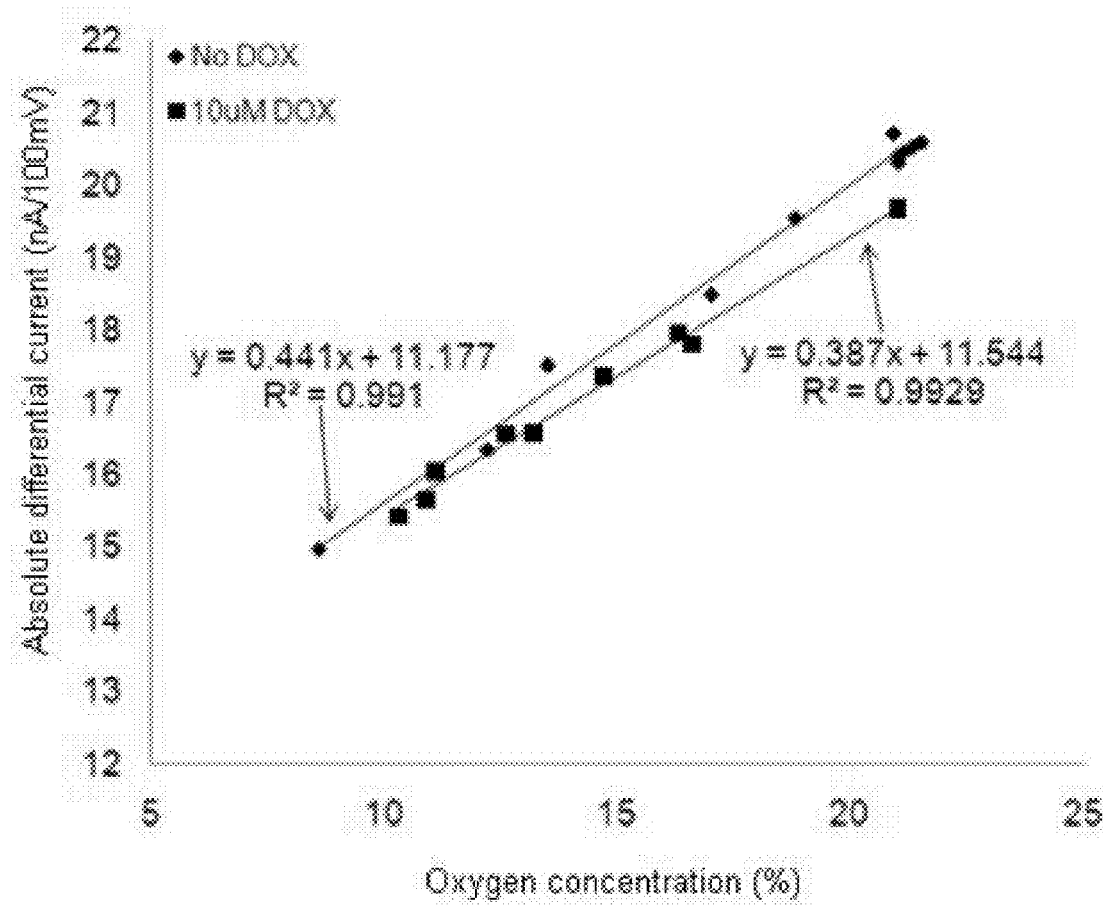
FIG. 38 is a graph showing oxygen calibration in PBS with and without 10 μm DOX.
Figure 39:
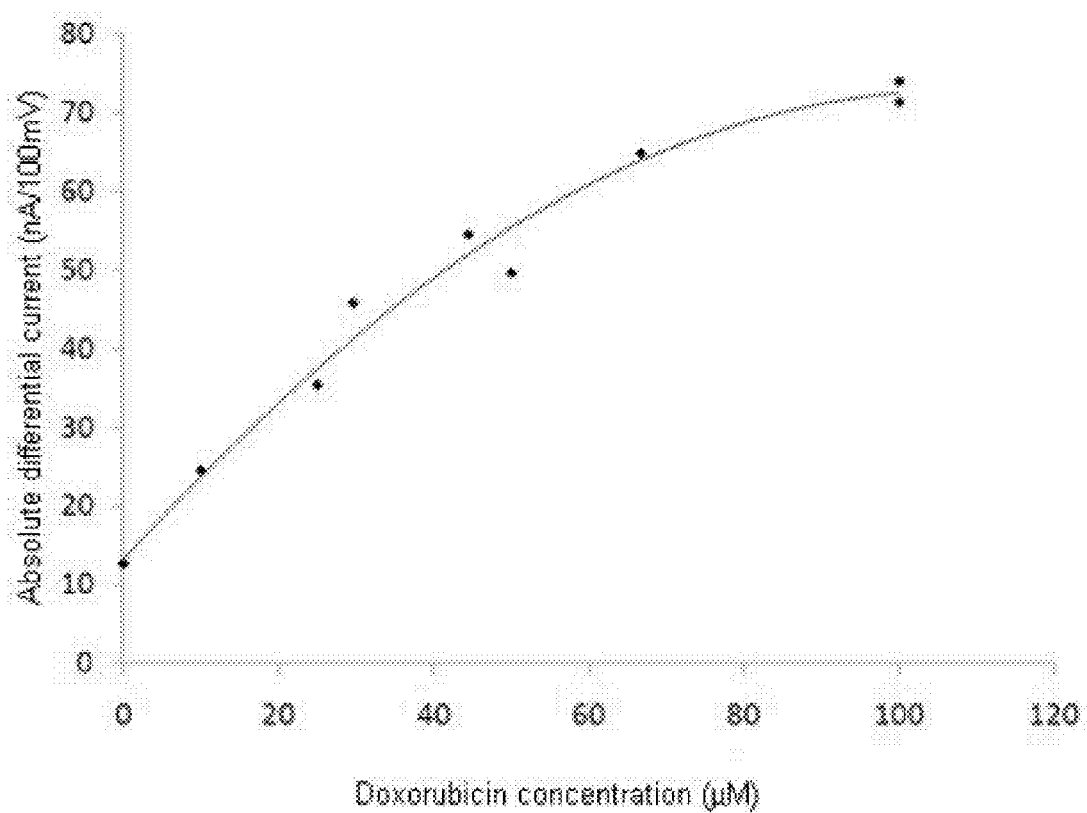
FIG. 39 is a graph showing DOX calibration in PBS equilibrated with ambient atmospheric $O_2$.

Oxygen and DOX concentrations were varied individually and oxygen and DOX reduction peaks were measured simultaneously in a single SWV scan. Potential was scanned from 0.1V to −1.1V with pulse amplitude of 50 mV and pulse increment of 10 mV. Pulses were applied at 30 Hz. This is preliminary evidence of detection O$_2$ and DOX using the same electrode which can be applied in the next generation multielectrode platform for investigating the correlation between drug penetration, drug efficacy and O$_2$ concentrations (FIGS. 37-39).

Example 11

Model for Oxygen Concentration Inside a Spheroid

The rate of change of radial oxygen concentration depends on the rate of diffusion of oxygen and rate of loss of oxygen by cellular consumption. Therefore, the overall problem of oxygen concentration can be defined by the following differential equation:

$$\frac{\partial C}{\partial t} = D\left(\frac{\partial^2 C}{\partial r^2} + \frac{2}{r}\frac{\partial C}{\partial r}\right) - q(r),$$

where:
C=oxygen concentration;
D=diffusion coefficient of oxygen;
t=time;

$r$ = radial distance from the center of the spheroid; and
$q(r)$ = rate of oxygen consumption.

$$= 0 \quad r > R$$

$$= K'C \quad 0 \leq r \leq R, \text{ for steady-state boundary value problem}$$

$K'$ = rate constant consumption.

Therefore, we can divide this problem into two compartments, medium and spheroid. Designating subscript m for medium and subscript s for spheroid, the steady state problem can be defined as:

$$\frac{\partial^2 C_m}{\partial r^2} + \frac{2}{r}\frac{\partial C_m}{\partial r} = 0$$

$$\frac{\partial^2 C_s}{\partial r^2} + \frac{2}{r}\frac{\partial C_s}{\partial r} = \frac{K'}{D_s}C_s$$

Substituting $U = C_r$ for both the medium and spheroid oxygen concentrations:

$$\frac{\partial^2 U_m}{\partial r^2} = 0$$

$$\frac{\partial^2 U_s}{\partial r^2} = \frac{K'}{D_s}U_1 = KU_s \Rightarrow \frac{\partial^2 U_s}{\partial r^2} - KU_s = 0$$

Steady-state solutions for the above homogeneous equations are:

$$U_m = B_0 r + A$$

$$U_s = B_1 e^{-\sqrt{K}r} + B_2 e^{\sqrt{K}r}$$

Replacing $C = U/r$:

$$C_m = B_0 + \frac{A}{r}$$

$$C_s = \frac{B_1 e^{-\sqrt{K}r} + B_2 e^{\sqrt{K}r}}{r}$$

Boundary Conditions

Concentration of oxygen in the bulk solution at infinite distance from the spheroid is constant and equal to the ambient partial pressure of oxygen, $r \to \infty$:

$$C = C_\infty \quad (6.1)$$

Oxygen flux across the central axis of the spheroid, $r=0$ is zero:

$$\frac{dC_s}{dr} = 0 \quad (6.2)$$

Continuous concentration and flux at the boundary of the spheroid $r=R$:

$$C_s = C_m \quad (6.3)$$

$$D_s \frac{dC_s}{dr} = D_m \frac{dC_m}{dr} \quad (6.4)$$

Particular Solution

From (6.1), at $r \to \infty$, $B_0 = C_\infty$:

$$\therefore C_m = C_\infty + \frac{A}{r} \quad (6.5)$$

Applying the (6.2) boundary condition:

$$B_1 = -B_2 = B \quad (6.6)$$

$$\therefore C_s = \frac{-B_1 e^{-\sqrt{K}r} + B_1 e^{\sqrt{K}r}}{r}$$

$$C_s = B\frac{\sinh(\sqrt{K}r)}{r}$$

From (6.3) boundary condition:

$$C_m = C_s \text{ at } r = R \quad (6.7)$$

$$C_\infty + \frac{A}{R} = \frac{2B}{R}\sinh(\sqrt{K}R)$$

$$A = 2B\sinh(\sqrt{K}R) - C_\infty R$$

Derivatives of oxygen concentration profiles in the medium and the spheroids are:

$$\frac{dC_m}{dr} = -\frac{A}{r^2}$$

$$\frac{dC_s}{dr} = \frac{2B\sqrt{K}}{r}\cosh(\sqrt{K}r) - \frac{2B}{r^2}\sinh(\sqrt{K}r)$$

From (6.4) boundary condition:

$$-D_m \frac{A}{R^2} = D_s\left(\frac{2B\sqrt{K}}{R}\cosh(\sqrt{K}R) - \frac{2B}{R^2}\sinh(\sqrt{K}R)\right)$$

$$-D_m A = 2BRD_s \sqrt{K}\cosh(\sqrt{K}R) - 2BD_s \sinh(\sqrt{K}R)$$

Substituting A from (6.7):

$$-D_m(2B\sinh(\sqrt{K}R) - C_\infty R) = \quad (6.8)$$

$$2BRD_s\sqrt{K}\cosh(\sqrt{K}R) - 2BD_s\sinh(\sqrt{K}R)$$

$$\therefore B = \frac{-D_m C_\infty R}{2\sinh(\sqrt{K}R)(D_s - D_m) - 2D_s\sqrt{K}R\cosh(\sqrt{K}R)}$$

Equations (6.5) and (6.7) equation reference goes here are the equations for oxygen concentration inside the medium and spheroid, respectively, with constant A and B given by equations (6.6) and (6.8), respectively.

From the above description of the application, those skilled in the art will perceive improvements, changes and modifications. Such improvements, changes, and modifications are within the skill of those in the art and are intended to be covered by the appended claims. All patents, patent applications, and publications cited herein are incorporated by reference in their entirety.

Having described the invention, the following is claimed:

1. A system for multiparametric analysis comprising:
   a substrate having a multilayer configuration comprising:
   a base layer;
   an intermediate layer disposed on at least a portion of the first base layer including at least one array comprising spiral electrodes, wherein the spiral electrodes comprise Fermat's geometry; and
   a spacer layer disposed on at least a portion of the base layer to mitigate fouling of the spiral electrodes;
   a three-dimensional (3D) cell aggregate having a microliter volume disposed on the spacer layer of the substrate, the 3D cell aggregate having a longitudinal surface at least a portion of which covers one or more of the spiral electrodes, and wherein the 3D cell aggregate is heterogeneous comprising at least two cell types, and
   wherein the spiral electrodes obtain information used to detect one or more biomarkers in the 3D cell aggregate.

2. The system of claim 1, wherein the information obtained by the spiral electrodes is one or more of oxygen tension, hydrogen ion concentration, and drug concentration within the 3D cell aggregate.

3. The system of claim 1, wherein the 3D cell aggregate is a partial spheroid.

4. The system of claim 1, wherein the substrate is prepared using a MEMS microfabrication technique.

5. The system of claim 1, wherein the information is obtained by the spiral electrodes when a test agent is contacted with the 3D cell aggregate.

6. The system of claim 5, wherein the information comprises a response of the 3D cell aggregate to the test agent.

7. The system of claim 1, wherein the cell types comprise a non-cancerous cell type and a cancerous cell type.

8. The system of claim 1, wherein the biomarkers comprise at least one cancer biomarker.

9. The system of claim 1, wherein the 3D cell aggregate represents an in vivo environment.

10. The system of claim 1, wherein the 3D cell aggregate comprises a portion of tissue.

11. The system of claim 1, wherein the array comprises a diametric array of spiral electrodes along a diameter of the 3D cell aggregate.

12. A system for multiparametric analysis consisting of:
    a substrate having a multilayer configuration consisting of:
    a base layer;
    an intermediate layer disposed on at least a portion of the first base layer including at least one array comprising spiral electrodes, wherein the spiral electrodes comprise Fermat's geometry; and
    a spacer layer disposed on at least a portion of the base layer to mitigate fouling of the spiral electrodes; and
    a three-dimensional (3D) cell aggregate having a microliter volume disposed on the spacer layer of the substrate, the 3D cell aggregate having a longitudinal surface at least a portion of which covers one or more of the spiral electrodes, and wherein the 3D cell aggregate is heterogeneous comprising at least two cell types.

13. The system of claim 1, wherein the information comprises currents detected by the spiral electrodes, wherein the currents are differentially measured.

* * * * *